(12) United States Patent
Yu

(10) Patent No.: US 9,896,714 B2
(45) Date of Patent: Feb. 20, 2018

(54) METHOD OF DETECTING PHYTASE ACTIVITY OR PROTEASE ACTIVITY

(75) Inventor: Shukun Yu, Malmo (SE)

(73) Assignee: DUPONT NUTRITION BIOSCIENCES APS (DK)

( * ) Notice: Subject to any disclaimer, the term of this patent is extended or adjusted under 35 U.S.C. 154(b) by 0 days.

(21) Appl. No.: 13/518,785

(22) PCT Filed: Dec. 17, 2010

(86) PCT No.: PCT/IB2010/055912
§ 371 (c)(1),
(2), (4) Date: Jun. 22, 2012

(87) PCT Pub. No.: WO2011/077342
PCT Pub. Date: Jun. 30, 2011

(65) Prior Publication Data
US 2012/0264153 A1  Oct. 18, 2012

Related U.S. Application Data

(60) Provisional application No. 61/298,670, filed on Jan. 27, 2010.

(30) Foreign Application Priority Data

Aug. 6, 2010 (EP) .................................. 10172171

(51) Int. Cl.
| | | |
|---|---|---|
| C12Q 1/37 | (2006.01) | |
| C12Q 1/42 | (2006.01) | |
| C12Q 1/68 | (2006.01) | |
| G01N 33/49 | (2006.01) | |
| G01N 33/569 | (2006.01) | |
| G01N 33/574 | (2006.01) | |

(52) U.S. Cl.
CPC .................. *C12Q 1/37* (2013.01); *C12Q 1/42* (2013.01); *C12Q 1/68* (2013.01); *G01N 33/491* (2013.01); *G01N 33/56966* (2013.01); *G01N 33/57484* (2013.01)

(58) Field of Classification Search
CPC ....................................................... C12Q 1/37
See application file for complete search history.

(56) References Cited

PUBLICATIONS

International Search Report for App. No. PCT/IB2012/055912, dated Nov. 5, 2011.
Kies Arie K et al: "Interaction between protein, phytate, and microbial phytase. In vitro studies.", Journal of Agricultural and Food Chemistry Mar. 8, 2006 LNKD-PUBMED:16506829, vol. 54, No. 5, Mar. 8, 2006 (Mar. 8, 2006), pp. 1753-1758, XP002608113, ISSN: 0021-8561 tables 2-4.
Howson S J et al: "Production of phytate-hydrolysing enzyme by some fungi", Enzyme and Microbial Technology, Stoneham, MA, US LNKD-DOI:10.1016/0141-0229(83)90012-1, vol. 5, No. 5, Sep. 1, 1983 (Sep. 1, 1983), pp. 377-382, XP023678073, ISSN: 0141-0229 [retrieved on Sep. 1, 1983] *abstract; figure 1.
Chen Jinn Chu: "Novel screening method for extracellular phytase-producing microorganisms", Biotechnology Techniques, vol. 12, No. 10, Oct. 1998 (Oct. 1998), pp. 759-761, XP002629603, ISSN: 0951-208X the whole document.
Vaintraub I A et al: "Effect of Phytate on the In-Vitro Activity of Digestive Proteinases", Journal of Agricultural and Food Chemistry, vol. 39, No. 5, 1991, pp. 859-861, XP002598821, ISSN: 0021-8561 chapter "Materials and Methods"; * abstract; figures 1-4; table 1.
Murthy N V K K et al: "Interaction of Phytate With Mustard *Brassica-juncea* 12S Protein", Journal of Agricultural and Food Chemistry, vol. 32, No. 3, 1984, pp. 493-498, XP002608114, ISSN: 0021-8561 figure 5.
Engelen Adrianus J et al: Determination of phytase activity in feed by a colorimetric enzymatic method: Collaborative interlaboratory study:, Journal of AOAC International, AOAC International, Arlington, VA, US, vol. 84, No. 3, May 1, 2001 (May 1, 2001), pp. 629-633, XP009100871, ISSN: 1060-3271 the whole document.
Serraino M R et al: "Removal of Phytic-Acid and Protein Phytic-Acid Interactions in Rapeseed", Journal of Agricultural and Food Chemistry, vol. 32, No. 1, 1984, pp. 38-40, XP002598820, ISSN: 0021-8561 * abstract; figures 1,2 chapter "Material and Methods".
Engelen, Adrianus J., et al., "Simple and Rapid Determination of Phytase Activity" Journal of AOAC International vol. 77, No. 3, 1994.

*Primary Examiner* — Suzanne M Noakes

(57) ABSTRACT

A method of detecting a phytase activity or a protease activity is described. The method comprises the steps of: (a) providing a composition comprising a phytate/protein complex in a liquid or a gel; wherein the phytate/protein complex provides a detectable property to the composition; (b) providing a sample that comprises or is suspected of comprising phytase activity and/or protease activity, wherein the phytase and/or protease activity is capable of causing a change in the detectable property of the composition; (c) contacting the composition with the sample; and (d) determining if there is a detectable change in detectable property of the composition.

12 Claims, 28 Drawing Sheets

METHOD OF DETECTING PHYTASE ACTIVITY OR PROTEASE ACTIVITY

CROSS-REFERENCE TO RELATED APPLICATIONS

This application claims priority to PCT Application No. PCT/IB2010/055912 entitled "Method," filed Dec. 17, 2010, which claims priority to Great Britain Application No. 1020257.0, filed Nov. 30, 2010, which claims priority to European Application No. 10172171.0; filed Aug. 6, 2010, which claims priority to U.S. Application No. 61/298,670, filed Jan. 27, 2010, which claims priority to Great Britain Application No. 0922485.8; filed Dec. 23, 2009 all of which are expressly incorporated by reference herein in their entirety.

FIELD OF THE PRESENT INVENTION

The present invention relates to a method. In particular, the present invention relates to a method of detecting enzymatic activity.

More in particular, in some respects, the present invention relates to a method of detecting phytase activity or protease activity using a disperse phase comprising a polyvalent component and an ionic component such as a protein or a fatty acid, wherein the disperse phase is held together by an intermolecular interaction, to the use of such a disperse phase in a method for detecting enzyme activity and to a kit for conducting such a method.

BACKGROUND OF THE PRESENT INVENTION

Several methods for detecting enzyme activity, also called enzyme activity assays, are known in the art.

Examples of known enzyme activity assays are assays for detecting phytase activity and for protease activity. However, known phytase activity assay methods are based on the release of inorganic phosphate by phytase from inositol phosphate. The amount of phosphate released from the inositol phosphate by the phytase can be assayed by a number of known methods (for example see Fiske (1925) and Lowry (1946)). Kits for performing phytase activity assays based on the release of inorganic phosphate from inositol phosphate are commercially available (for example phytic acid (phytate) total phosphorous assay available from Megazyme International Ireland Limited).

There are several disadvantages of the known phytase activity assay methods. One disadvantage is that they are end point assay methods, meaning that the amount of inorganic phosphate can only be measured after the enzymic reaction has been stopped. This makes it difficult to do kinetic studies of phytase activity.

Another disadvantage of these known assays is that the assay background is complicated by inorganic phosphate that exists naturally in biological samples or is added thereto. As the level of inorganic phosphate released by phytase is measured to assess phytase activity, this variable background level of inorganic phosphate can make the results variable and unreliable, particularly when used on biological samples.

A third disadvantage of some prior art methods is the toxic nature of the reagents used, such as molybdate and vanadium.

Phytase activity can also be measured based on assaying the release of inositol from inositol phosphate when it is degraded by phytase. Inositol is assayed using inositol dehydrogenase by known methods (for example see Prestwich (1991)).

The disadvantage of this method is that an additional enzyme called phosphatase is needed to hydrolyze inositol monophosphate to inositol, as commercial phytases have little or no activity on inositol monophosphate. Assaying inositol can also be problematic because many biological samples have high background levels of inositol, which is one of the major polyols in many biological systems.

Phytase activity may also be assayed using calcium phytate as a substrate at pH 5.5 or above. Calcium phytate has a certain turbidity and hydrolysis of this substrate by phytase causes the turbidity to decrease. The substrate can be added to an agarose gel so that the phytase can be assayed using plate diffusion assay. The disadvantage of this method is that the turbidity of calcium phytate is low, and it has no turbidity at lower pH. In addition, calcium phytate is not an ideal substrate for commercial histidine acid phytases. Another disadvantage of the plate assay is that acid producing microbes will produce false results as the acid produced will dissolve the calcium phytate thereby forming clear halos (see Howson and Davis 1983).

A semi-quantitative antibody-based phytase assay is described in WO2007001895. This method uses antibodies that can bind to phytase to assay phytases. But a drawback of this method is that it can not reliably differentiate between active, partially-heated inactivated and heat-inactivated phytase, for example phytase that has been heat-inactivated during feed processing. The other disadvantages of this technology are that it is expensive to develop, it is time consuming, the results are unreliable, and can lead to false positive results. False positive results indicate either that there is phytase present when there is not, or that the phytase present is not active. This can lead to less phytase being added than is needed to give the required amount of phytase activity. If not enough phytase activity is present in the feed animals fed on the feed may not have enough available phosphate.

Feed or feed ingredients or feed mixtures (premix) may be tested to identify whether they contain phytase and how much phytase they contain. If there is not enough phytase in the feed or feed ingredient additional phytase can be added. False negative results in tests for phytase can lead to too much phytase being added to the feed, which is costly.

There are many known methods for the assay of protease activity. Many of them are based on synthetic peptides or peptide analogues often labelled with chromophores or fluorophores. The advantage of these methods is their high sensitivity and their capability to monitor protease activity kinetically.

A disadvantage of these methods is that information obtained with synthetic peptides can not be related to that obtained with natural proteins with a high degree of certainty as natural proteins often have complicated conformations which change with their environment.

Other methods use natural proteins as a substrate to detect protease activity. The disadvantage of using natural proteins as a substrate for proteases in the prior art methods is that monitoring of protein hydrolysis is usually done by indirect methods. This means that these methods are end point assays which measure the products of the reaction only after it has been stopped. These methods therefore do not lend themselves to doing kinetic studies on natural proteins.

An example of a protease activity assay that is done using a natural protein is a pepsin activity assay that can be performed using haemoglobin as a substrate. Pepsin activity can be related to the release of trichloroacetic acid (TCA) soluble aromatic amino acids and peptides. The method has to be an end point assay because the enzyme reaction has to be stopped using TCA before its products can be assayed.

The same is true for protease assays using casein, which is often cross-linked with chromophores. The reaction has to be stopped by raising the pH in order to separate soluble chromophores from insoluble substrate.

The present invention seeks to provide a useful assay method. In particular the present invention seeks to provide an assay method that is particularly useful in testing feed or feed ingredients or feed mixtures (premix) to identify whether they contain phytase and/or protease and, in some instances, the level thereof.

SUMMARY ASPECTS OF THE PRESENT INVENTION

Aspects of the present invention are presented in the claims and in the following commentary.

In one aspect, the present invention relates to a method of detecting a phytase activity or a protease activity comprising the steps of:
(a) providing a composition comprising a phytate/protein complex in a liquid or a gel;
wherein the phytate/protein complex provides a detectable property to the composition;
(b) providing a sample that comprises or is suspected of comprising phytase activity and/or protease activity, wherein the phytase and/or protease activity is capable of causing a change in the detectable property of the composition;
(c) contacting the composition with the sample;
(d) determining if there is a detectable change in detectable property of the composition.

In another aspect, the present invention relates to a method for detecting enzymatic activity comprising the steps of:
(a) providing a medium comprising a continuous and a disperse phase,
wherein the disperse phase comprises:
  i) a first component which is a polyvalent component, and
  ii) a second component which is an ionic component,
wherein the polyvalent component and the ionic component are held together by one or more intermolecular interactions to form the disperse phase,
wherein the disperse phase provides a detectable property to the medium;
(b) providing a sample that comprises or is suspected of comprising the enzymatic activity,
wherein the enzymatic activity is capable of affecting the disperse phase to cause a detectable change in the detectable property of the medium;
(c) contacting the medium with the sample;
(d) determining if there is a change in the detectable property of the medium.

In another aspect the present invention relates to a method for detecting an enzymatic activity which is a phytase activity or protease activity comprising the steps of:
(a) providing a medium comprising a continuous and a disperse phase,
wherein the disperse phase comprises:
  i) a protein, and
  ii) phytic acid,
wherein the protein has at least one positively charged group, or wherein the medium is below the pI of the protein and the protein and the phytic acid are held together by one or more intermolecular interactions to form the disperse phase,
wherein the disperse phase provides turbidity, viscosity or fluorescence to the medium;
(b) providing a sample that comprises or is suspected of comprising the enzymatic activity,
wherein the enzymatic activity is capable of affecting the disperse phase to cause a detectable change in the turbidity, viscosity or the fluorescence of the medium;
(c) contacting the medium with the sample;
(d) determining if there is a detectable change in the turbidity, absorbance, viscosity or the fluorescence of the medium.

In another aspect the present invention relates to a quantitative, semi-quantitative or qualitative assay method for detecting enzyme activity comprising the method according to the previous aspects.

In another aspect the present invention relates to a kit for detecting phytase or protease activity using the method according to the previous aspects.

In another aspect the present invention relates to a use of a method according to the previous aspect or a kit according to the previous aspect for testing enzyme activity in a biological sample—such as an enzyme preparation, a fermentation broth, a food, a feed, a food ingredient, a food ingredient mixture, a feed ingredient, a processed food product or a processed feed product or in an extract of any one thereof.

Methods, kits and uses as substantially described with reference to the figures and examples are also encompassed by the present invention.

BRIEF DESCRIPTION OF THE FIGURES

Reference is made herein to the following Figures.

The Figures are now described in more detail.

Figure 1A:
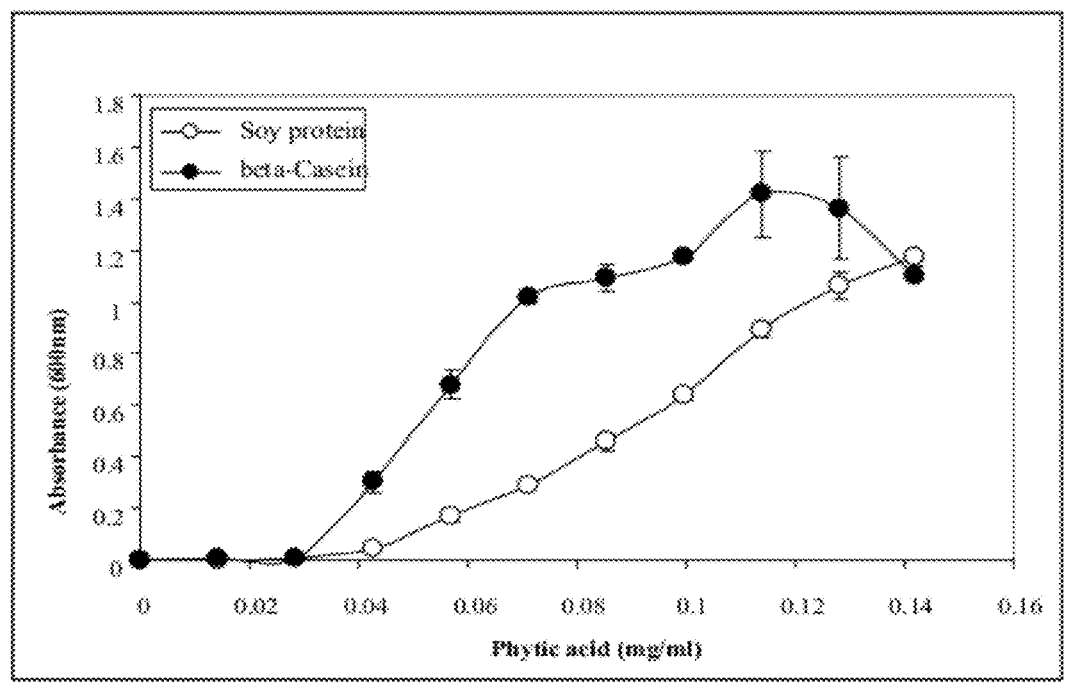
FIG. 1a which is a graph.

FIG. 1a shows the formation of complexes of soy protein and bovine β-casein as a function of phytic acid concentration at pH 3.0 in glycine-HCl. The degree of complex formation is measured by an increase in turbidity of the solution measured by absorbance of light at 600 nm wavelength. As can be seen from FIG. 1a, the amount of absorbance at 600 nm wavelength at a given phytic acid concentration depends on the type of protein used. Beta-Casein provides higher absorbance than soy protein in the range of phytic acid concentrations from 0.04 to about 0.14 mg/ml. The optimum ratio of protein to phytic acid can be tested for each type of protein. Glycine-HCl is the preferred buffer for these conditions.

Figure 1B:
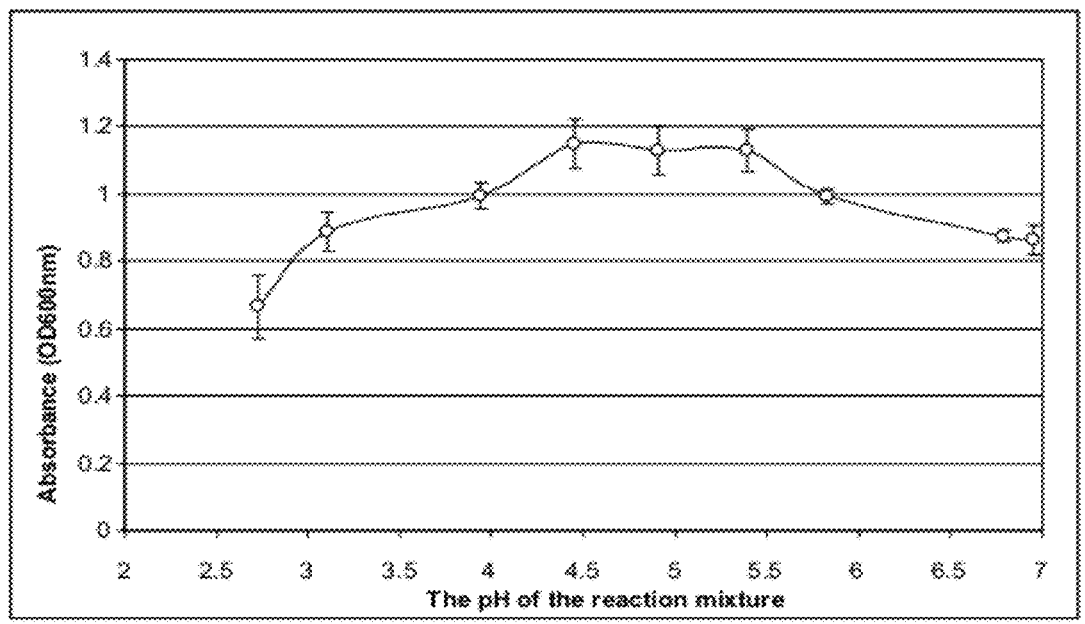
FIG. 1b which is a graph.

FIG. 1b shows the effect of pH on the absorbance of phytic acid-lysozyme complex from pH 2.73 to pH 6.95 in buffers of 40 mM glycine-HCl, acetate, Mes-NaOH at 0.3 mM myo-inositol hexakisphosphate (IP6) and 2.5 mg/ml lysozyme. As can be seen from FIG. 1b the absorbance at 600 nm (also called OD600) changes according to the pH. The optimum pH for each combination of protein and phytic acid can be determined.

Figure 2:
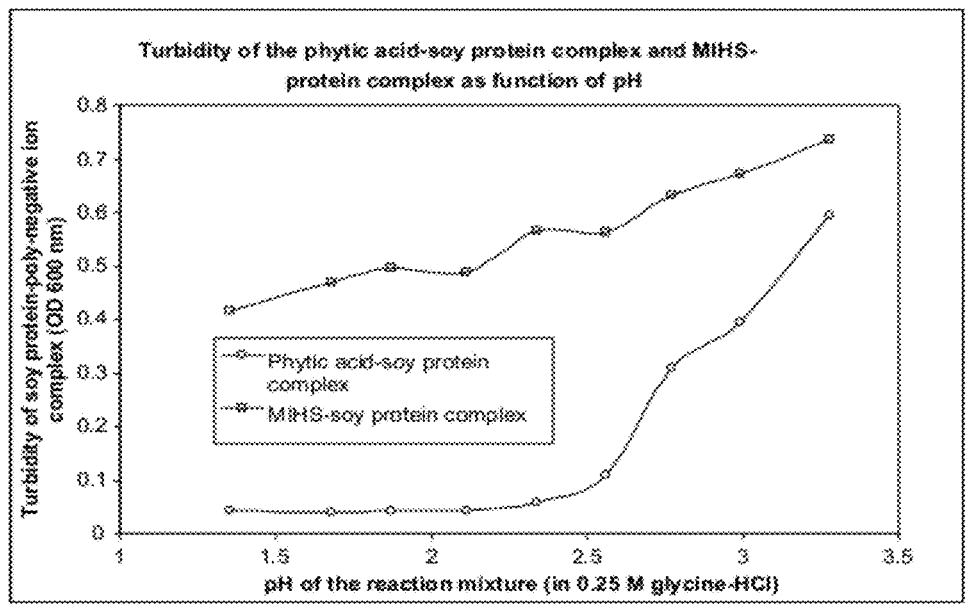
FIG. 2 which is a graph.

FIG. 2 shows the turbidity of solutions (corresponding to the medium) containing either a phytic acid-soy protein complex (corresponding to the disperse phase) or MIHS-soy protein complex as a function of the pH of the solution. As can be seen in FIG. 2, the turbidity produced by the protein complex varies with pH. The optimum pH for each combination of protein and phytic acid can be determined.

Figure 3:
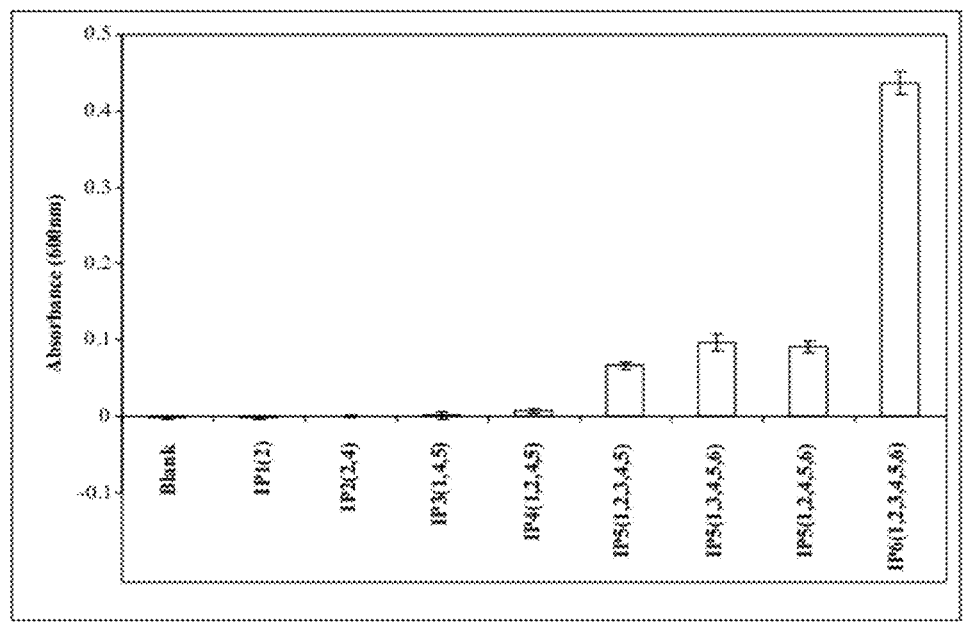
FIG. 3 which is a graph.

FIG. 3 shows the turbidity of solutions comprising different inositol phosphate esters myo-inositol monophosphate (IP1(2)), myo-inositol bisphosphate (IP2(2,4)), myo-inositol trisphosphate (IP3(1,4,5)), myo-inositol tetrakisphosphate (IP4(1,2,4,5)), myo-inositol pentakisphosphate (IP5(1,2,3,4,5)), myo-inositol hexakisphosphate (IP6 (1,2,3,4,5,6)) and IP5 positional isomers myo-inositol pentakisphosphate (IP5(1,3,4,5,6)) and myo-inositol pentakisphosphate (IP5(1,2,4,5,6)) forming complexes with soy protein. Complex formation causes increased turbidity in the solution, which is measured by an increase in absorbance of light at 600 nm by the solution. In particular, FIG. 3 shows surprisingly the dramatic decrease of turbidity when IP6 was converted to IP5, which forms the basis for the development of the current phytase assay method. In the literature it is usually assumed that the chelating capability decreases proportionally when IP6 is converted to IP5, IP4, IP3 and IP2 (Blaabjerg, K; Carlson, D.; Hansen-Møller, J.; Tauson, A.-H.; Poulsen, H. D. 2007).

Figure 4:
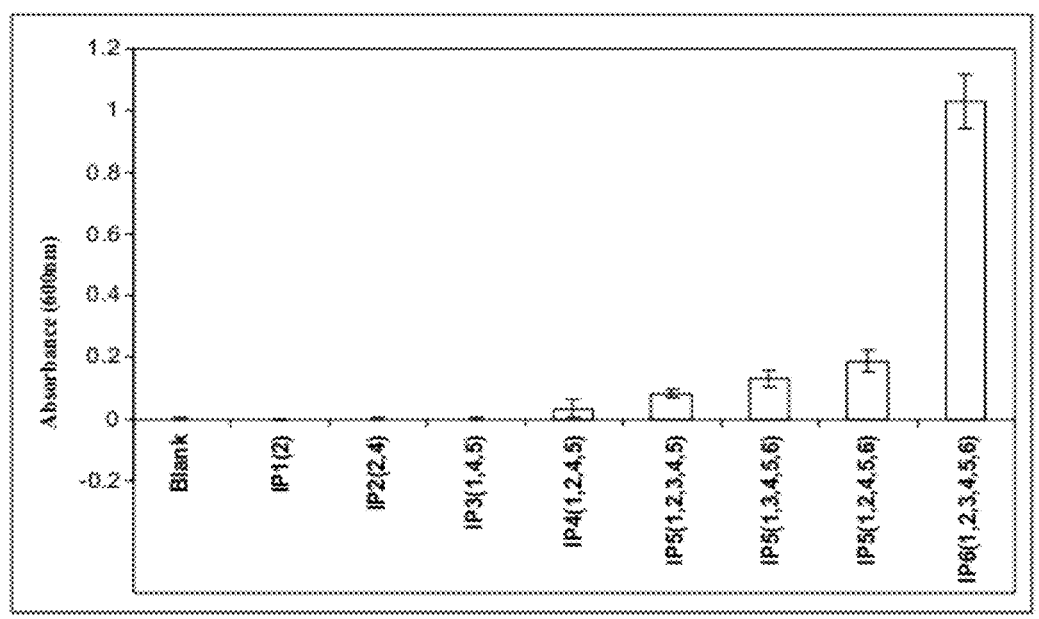
FIG. 4 which is a graph.

FIG. 4 shows the turbidity of solutions comprising different inositol phosphate esters (IP1-IP6) and IP5 positional isomers forming complexes with β-casein. Complex formation causes increased turbidity in the solution, which is measured by an increase in absorbance of light at 600 nm by the solution. In particular, FIG. 4 shows the dramatic decrease of turbidity when IP6 was converted to IP5.

Figure 5:
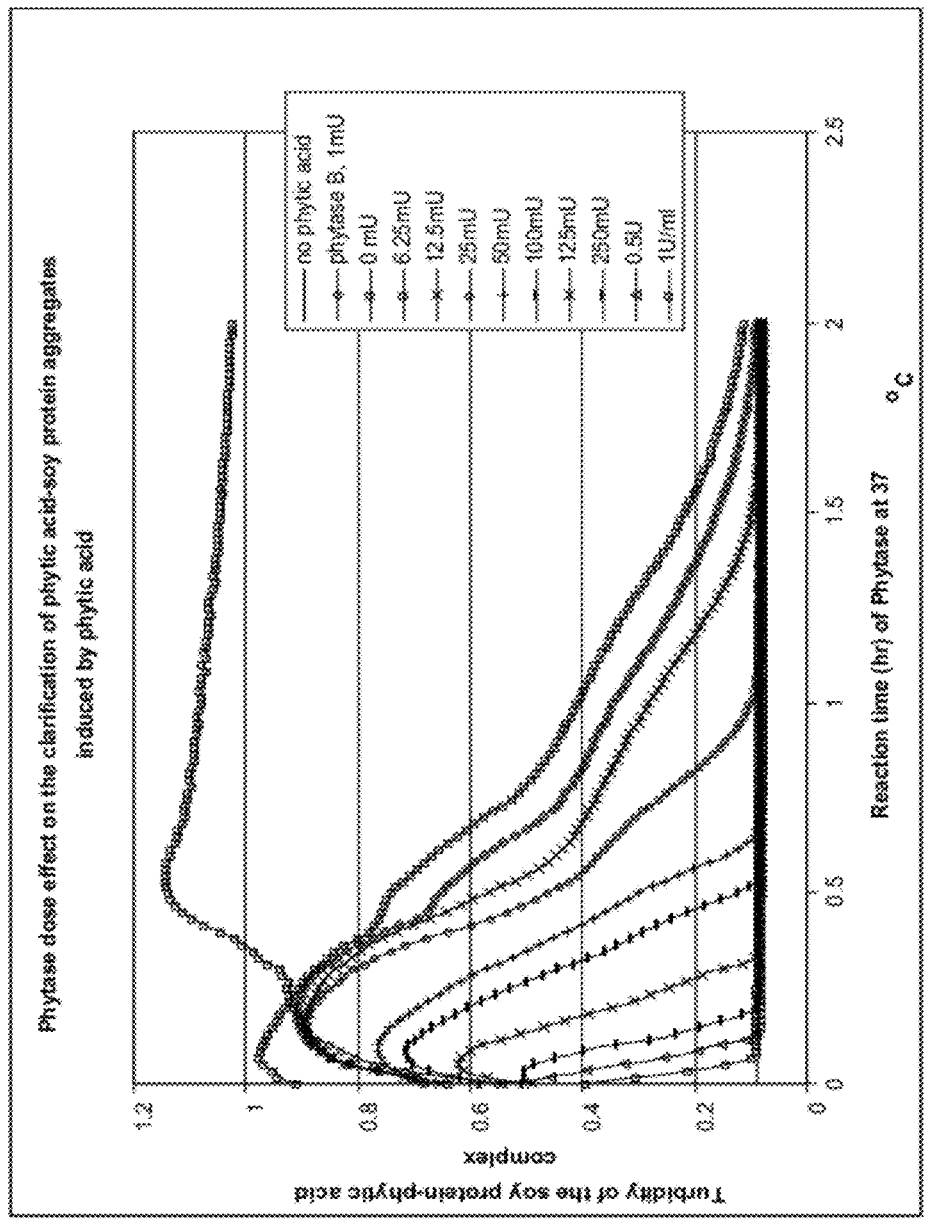
FIG. 5 which is a graph.

FIG. 5 shows the effect of different phytase dose levels (0-1 U/ml) in the reduction of the solution turbidity caused by soy protein-phytic acid complexes over time. As can be seen from FIG. 5, with no phytase present there is a very slow rate of decrease in turbidity (top line). With increasing phytase concentrations the turbidity of the solution decreases more rapidly.

Figure 6:
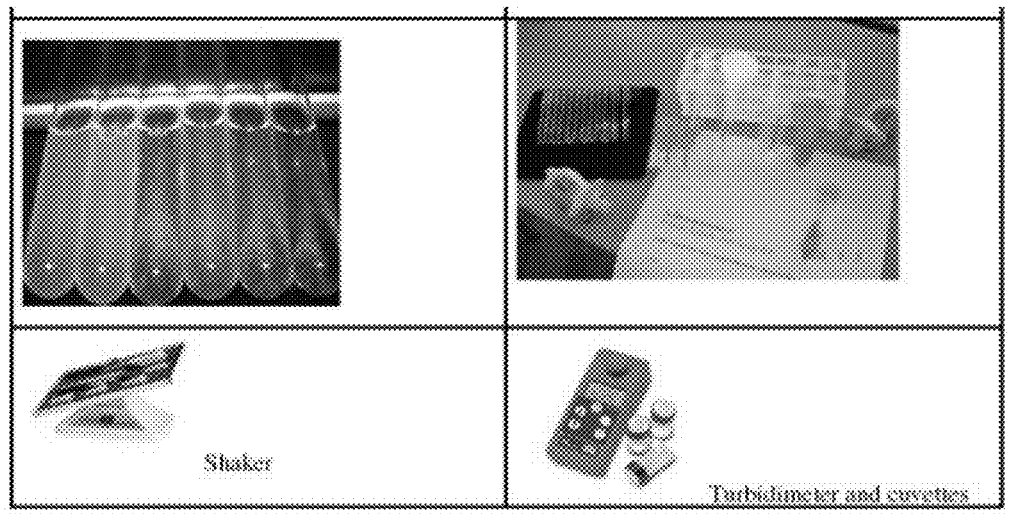
FIG. 6 which shows a series of photographs.

FIG. 6: Top left panel shows, tubes containing overnight incubation of filtered feed extract with phytic acid-soy protein complex. Tubes contain phytase (Phyzyme XP®), from left to right, 0 (control), 186, 442, 1129, 2301 and 210,368 FTU/kg (FTU=phytase units). Top right panel shows a phytase or protease activity test kit. Bottom left panel shows a shaker that can be used in the phytase or protease activity assay. Bottom right panel shows a turbidimeter and cuvettes that can be used in the phytase or protease activity assay.

Figure 7:
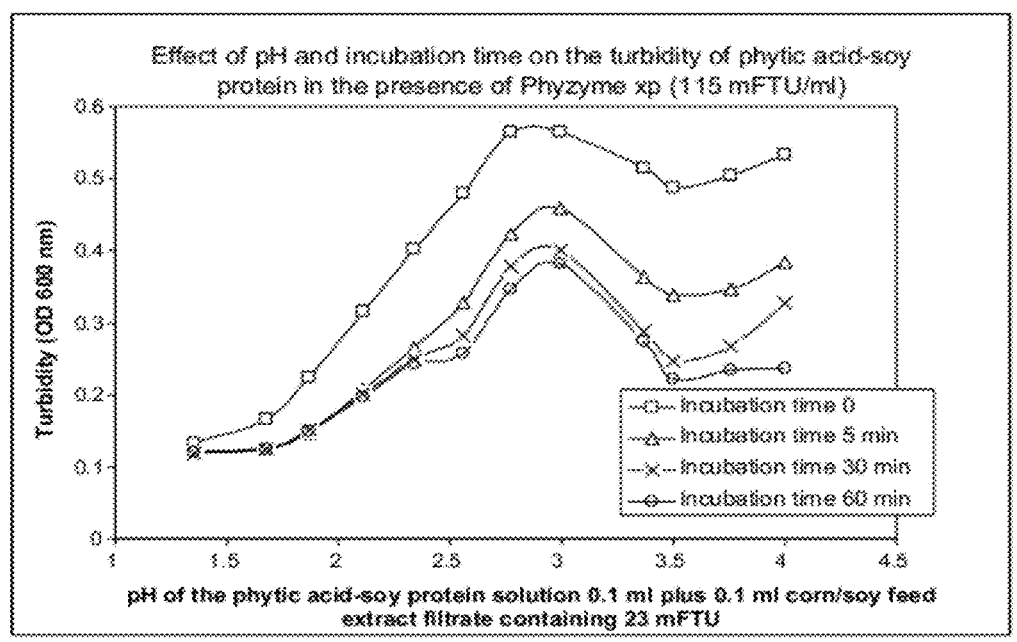
FIG. 7 which is a graph.

FIG. 7 shows the effect of pH and incubation time on the turbidity of solutions comprising phytic acid-soy protein complex in the presence of the phytase (Phyzyme XP®). As can be seen from FIG. 7, the longer the incubation time with phytase the lower the turbidity at all pH values tested.

Figure 8A:
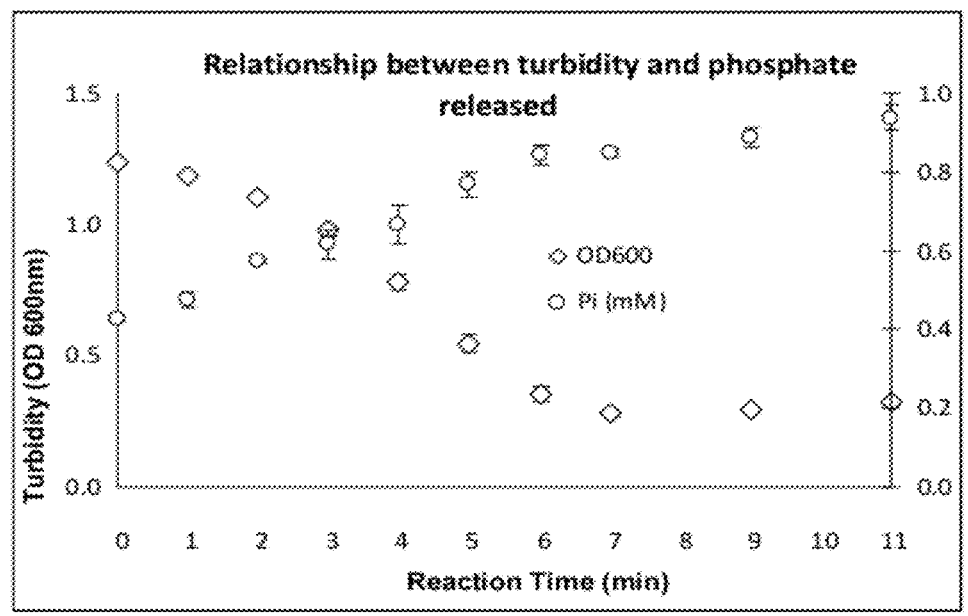
FIG. 8a which is a graph.

FIG. 8a shows the turbidity decrease of lysozyme-phytic acid complex caused by the presence of 0.1 FTU of phytase as a function of reaction time. The reaction was monitored by the decrease in absorbance at 600 nm and by measuring the inorganic phosphate released simultaneously. It can be seen from FIG. 8a that the decrease in turbidity is co-temporal with the increase in free inorganic phosphate released by the phytase. Therefore, turbidity is a good indicator of phytase activity.

Figure 8B:
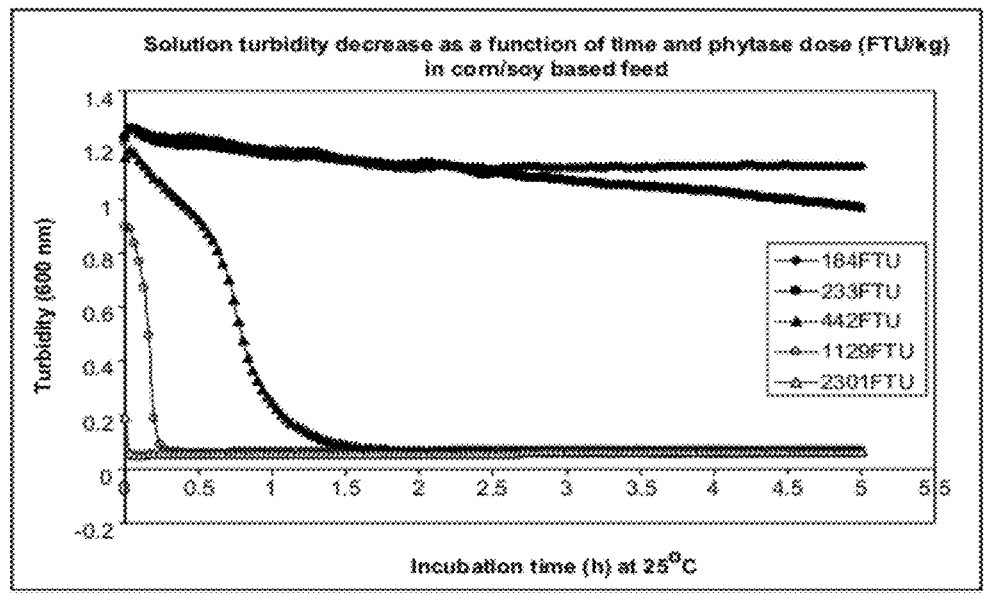
FIG. 8b which is a graph.

FIG. 8b shows the solution turbidity of soy protein-phytic acid complex decrease as a function of the time and phytase dose (FTU/kg) in corn/soy based feed as monitored by the decrease of absorbance at 600 nm.

Figures 9, 10:
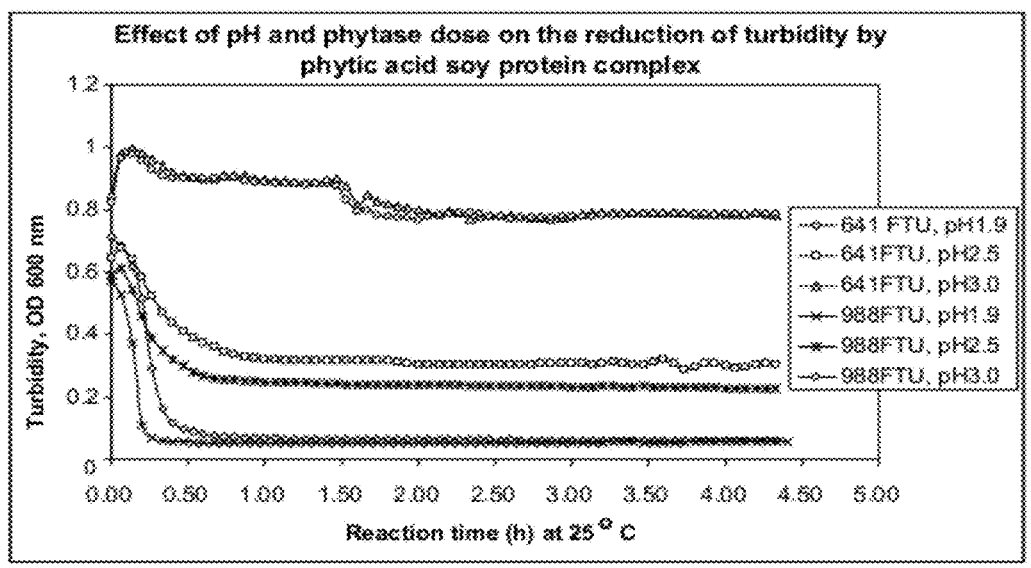
FIG. 9 which is a table and a photograph.
FIG. 10 which is a graph.

FIG. 9 shows the results (shown in the top panel) of phytase assays on feed samples done in a microplate (shown in the bottom panel). In particular FIG. 9 shows absorbance data in relation to the phytase units present in the feed. The feed samples were randomly selected from feed products made in Costa Rica (CR), China (CN), France (F) and Australia (AU). The phytase units are given after the country codes. As can be seen from FIG. 9, the turbidity measured in this assay varies between different feed samples.

FIG. 10 shows the effect of pH and phytase dose in reducing the turbidity of solutions containing phytic acid-soy protein complex. The reaction mixture contained 0.1 ml of 0.2M glycine-HCl with a pH of 1.9, 2.5 and 3.0 respectively and 0.1 ml feed water extract filtrate. The final sodium phytate concentration was 0.1 mM.

Figure 11A:
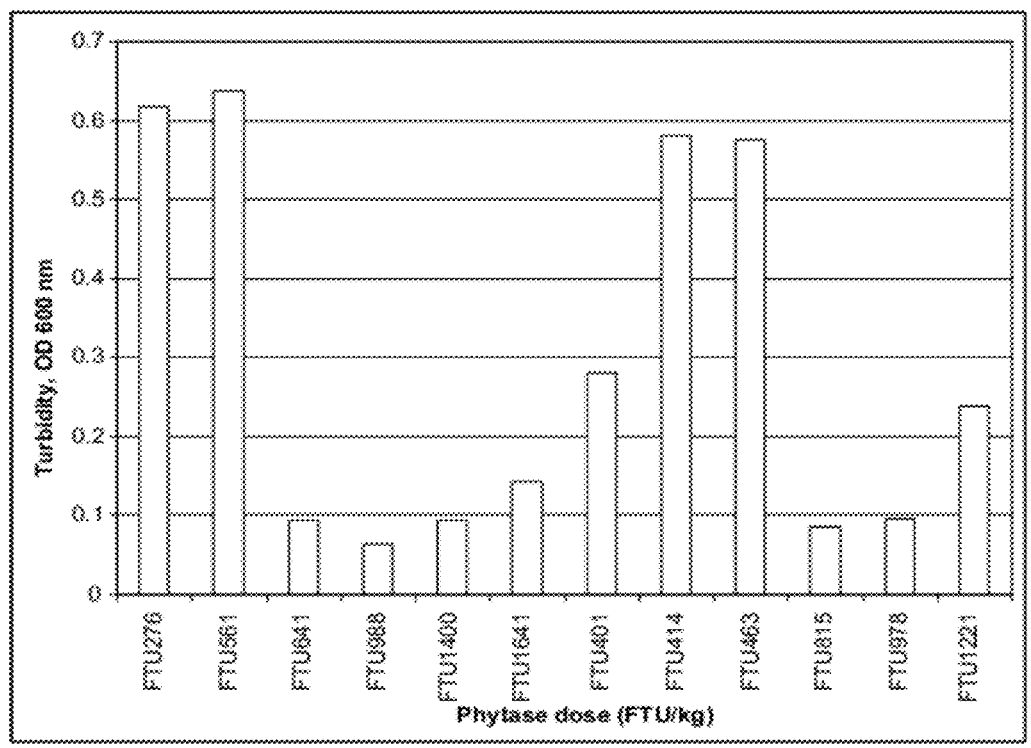
FIG. 11a which is a graph.
Figure 11B:
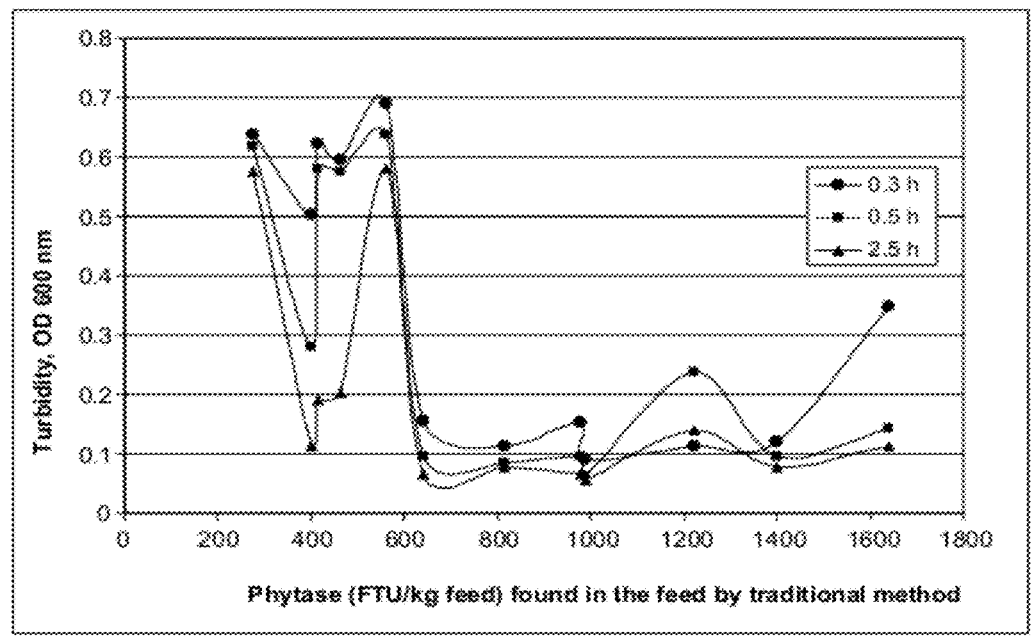
FIG. 11b which is a graph
FIG. 11c which is a graph.

FIG. 11a and FIG. 11b show the turbidity change in relation to the phytase dose and reaction time for 12 Canadian feed samples. As can be seen from FIG. 11a and FIG. 11b the phytase activity measured by the present method may differ from the phytase measured by prior art methods. This may be due to the presence of phytase inhibitors or to the type of feed matrix in the feed samples being tested. Controls may be used to account for differences in the reaction caused by phytase inhibitors in the sample or the type of feed matrix.

Figure 11C:
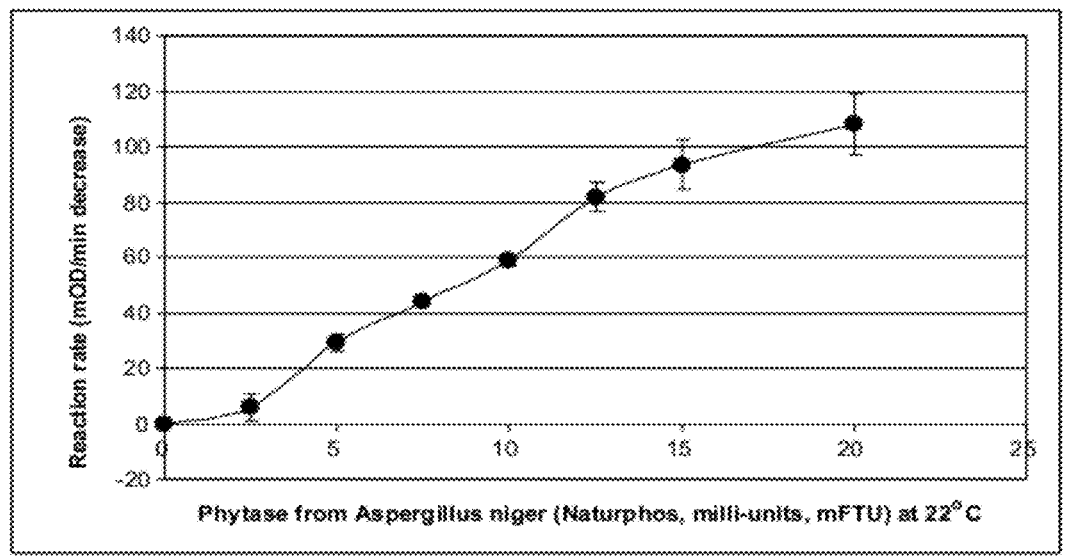

FIG. 11c shows the use of lysozyme and phytic acid complex as substrate in 35 mM sodium acetate (pH 5.49) for the assay of the *Aspergillus niger* phytase variant (Natuphos). The reaction mixture contained 35 μl of 50 mM buffer, lysozyme (2.5 mg/ml), sodium phytate (IP6) (0.3 mM) and the phytase in various amounts. The reaction was performed at 22° C. in a 96 well microplate and was followed by monitoring the absorbance decrease at 600 nm. As can be seen from FIG. 11c the rate of decrease in absorbance at 600 nm increased linearly with the number of phytase units present. Parameters of the assay may be adjusted to ensure that the reaction rate is conveniently measurable in a kit for measuring feed samples.

Figure 12A:
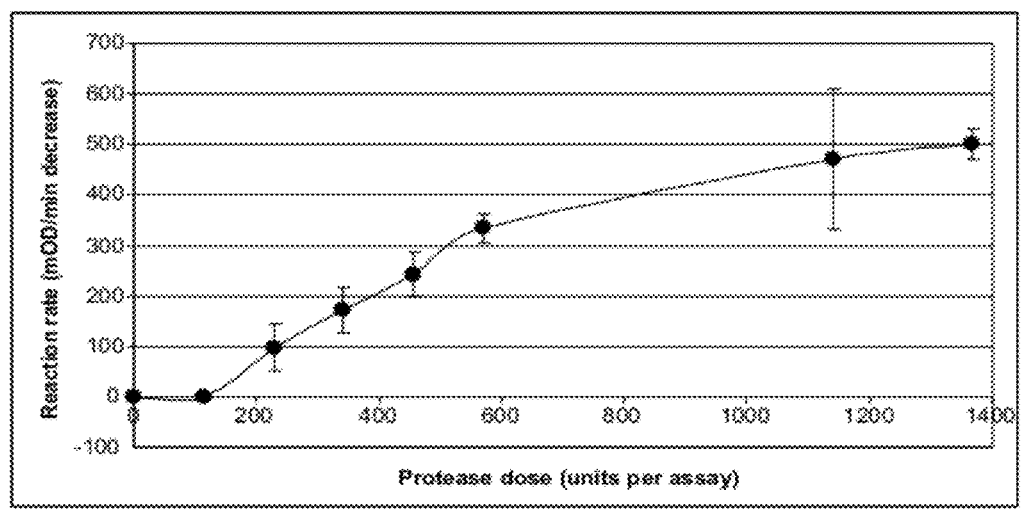
FIG. 12a which is a graph.

FIG. 12a shows the use of the protein (lysozyme)-phytic acid as substrate at pH 8.7 in 35 mM Tris-HCl for the assay of the alkaline protease P-3000 (a subtilisin variant). The reaction mixture contained 50 mM 35 µl buffer, lysozyme (2.5 mg/ml), sodium phytate (IP6) (0.3 mM) and the protease in various amounts. The reaction was performed at 22° C. in a 96 well microplate and was followed by monitoring the absorbance decrease at 600 nm. As can be seen from FIG. 12a the rate of decrease in absorbance at 600 nm increased almost linearly with the number of protease units present. Parameters of the assay may be adjusted to ensure that the reaction rate is conveniently measurable in a kit for measuring feed samples.

Figure 12B:
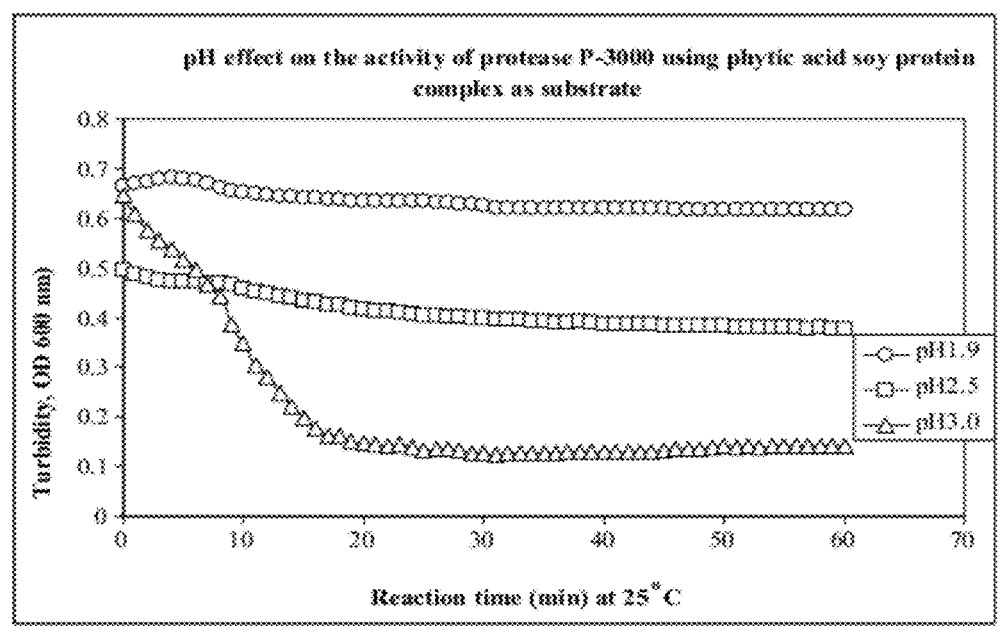
FIG. 12b which is a graph.

FIG. 12b shows the effect of pH on the activity of protease P-3000 using phytic acid soy protein complex as a substrate as indicated by changes in solution turbidity. It can be seen from FIG. 12b that this protease is more active at pH 3.0 than at pH 1.9 or pH 2.5. The pH used in the assay can be chosen according to what range of pH the enzyme is active at as well as to ensure that proteins that form part of the complex have the appropriate charge to form a complex.

Figure 13:
FIG. 13 which is a photograph.

FIG. 13 shows an example of a petri-dish based phytase and/or protease activity assay kit that can be complemented with a mini-incubator and ruler (not shown).

Figure 14:
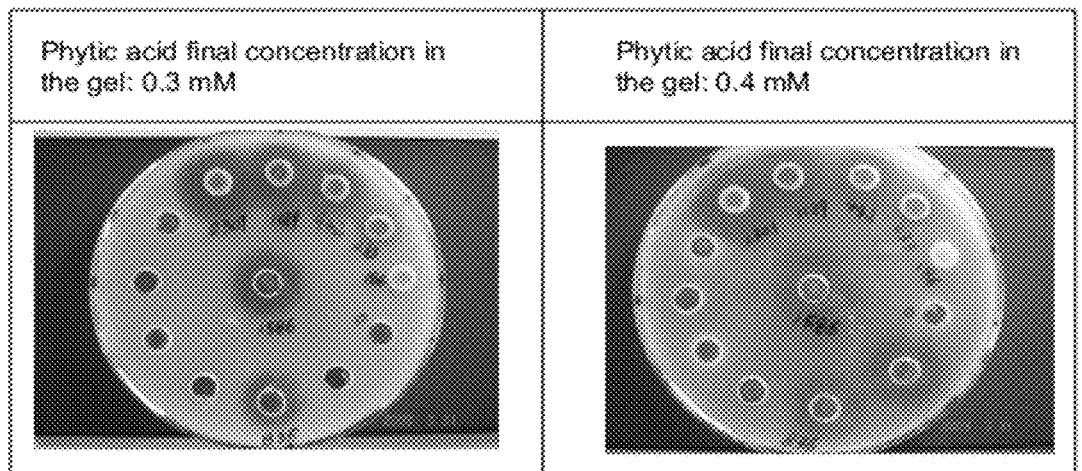
FIG. 14 which is two photographs.

FIG. 14 shows the results of petri-dish assays for phytase activity where the phytic acid concentration in the gel is 0.3 mM (left hand panel) and 0.4 mM (right hand panel). Wells marked with 0, 186, 233, 442, 1129 and 2301 contained corn/soy based feed extract with the phytase amount indicated (FTU/kg). Wells marked with 836 and 1586 contained wheat based feed extract having 836 and 1586 FTU/kg, respectively. As can be seen from FIG. 14 the final phytic acid concentration in the gel can be adjusted to give the best contrast between the turbidity of the gel and the clear halos that indicate phytase activity.

Figure 15:
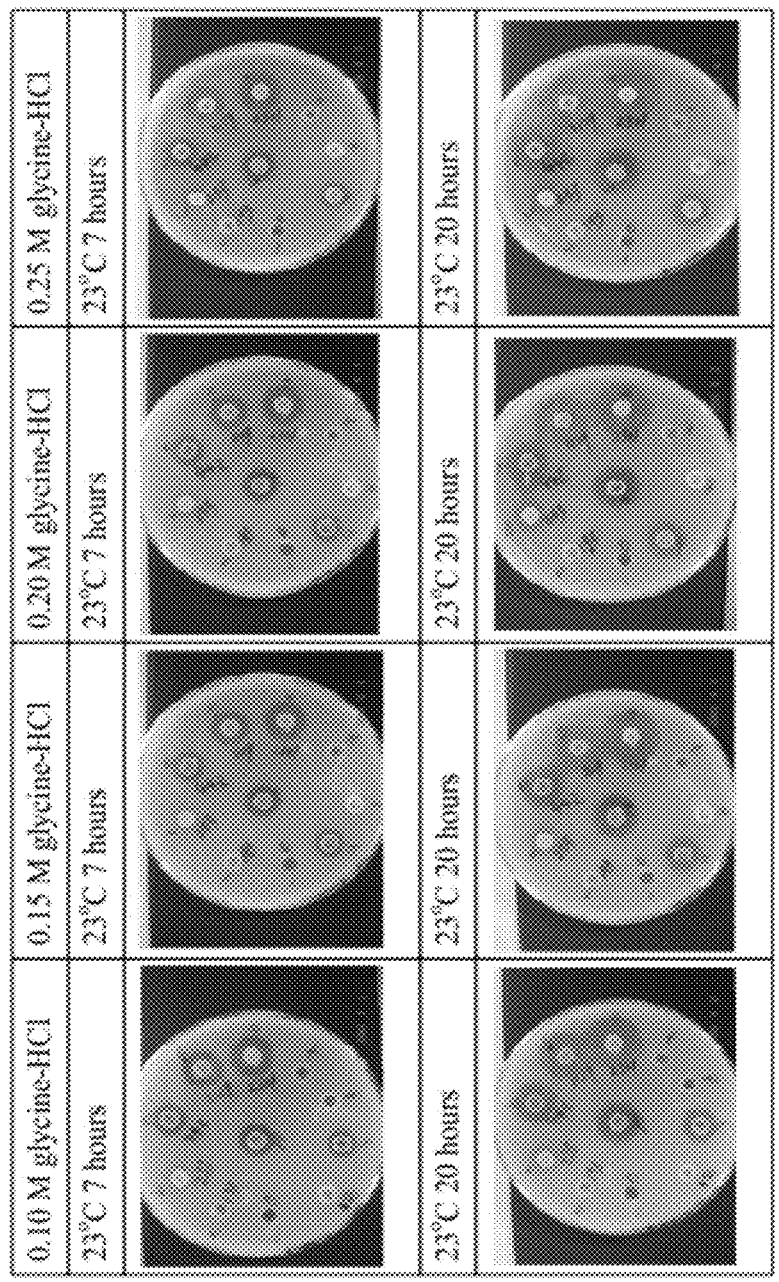
FIG. 15 which is a series of photographs.

FIG. 15 shows petri-dish assays for phytase activity with different concentrations of buffer (glycine-HCl, pH3.0). From left to right: 0.1 M, 0.15 M, 0.20 M, 0.25 M glycine-HCl. Wells marked with 0, 193, 233, 442, 1129 and 2301 contained corn/soy based feed extract with the phytase amount indicated (FTU/kg).

Figure 16:
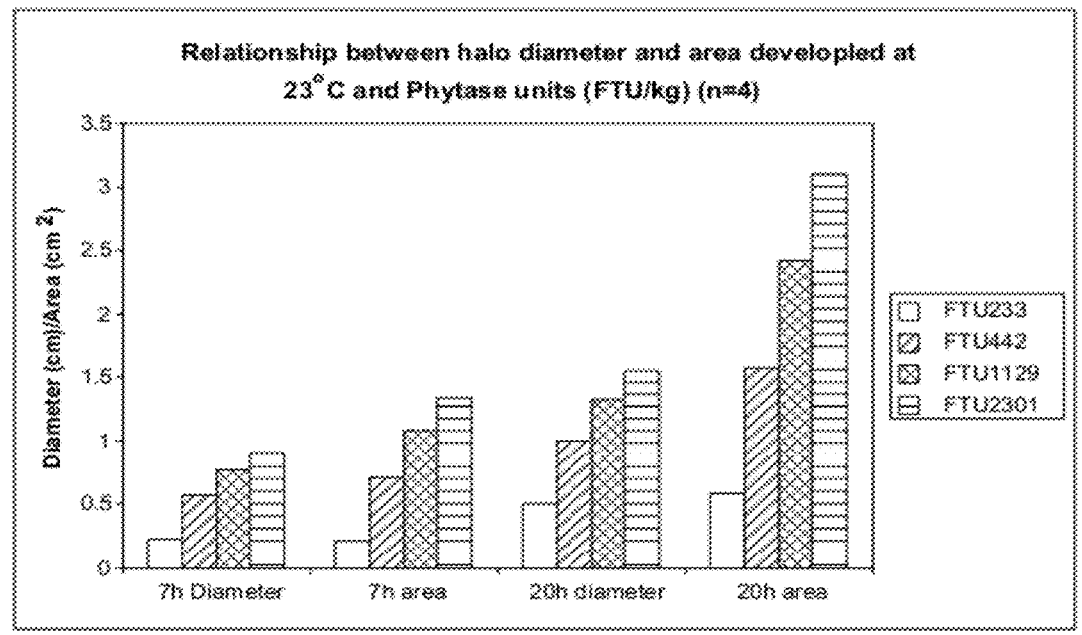
FIG. 16 which is a graph.

FIG. 16 shows the relationship between the halo diameter or halo area developed at 23° C. and the number of phytase units (FTU/kg) contained in the feed extract. For each group of 4 bars the bars correspond to 223, 442, 1129, 2301 FTU/kg (from left to right). As can be seen from FIG. 16 there is a positive correlation between halo diameter or area and phytase concentration.

Figure 17:
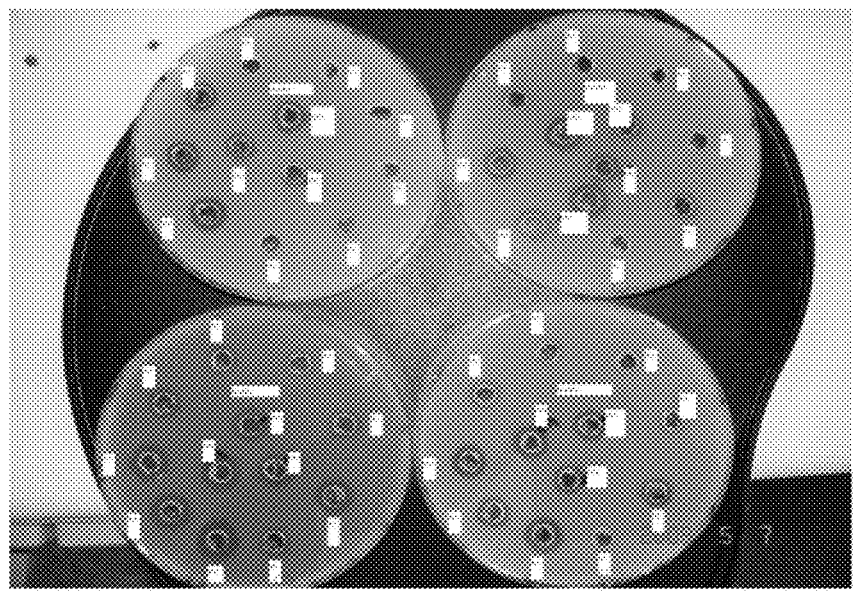
FIG. 17 which is a photograph.

FIG. 17 shows the effect of phytic acid concentration (0.1-0.4 mM) and feed water dilution factor on the halo size of agarose gel containing 0.1 M glycine-HCl pH 3.0 and soy protein 2 mg/ml.

Figure 18:
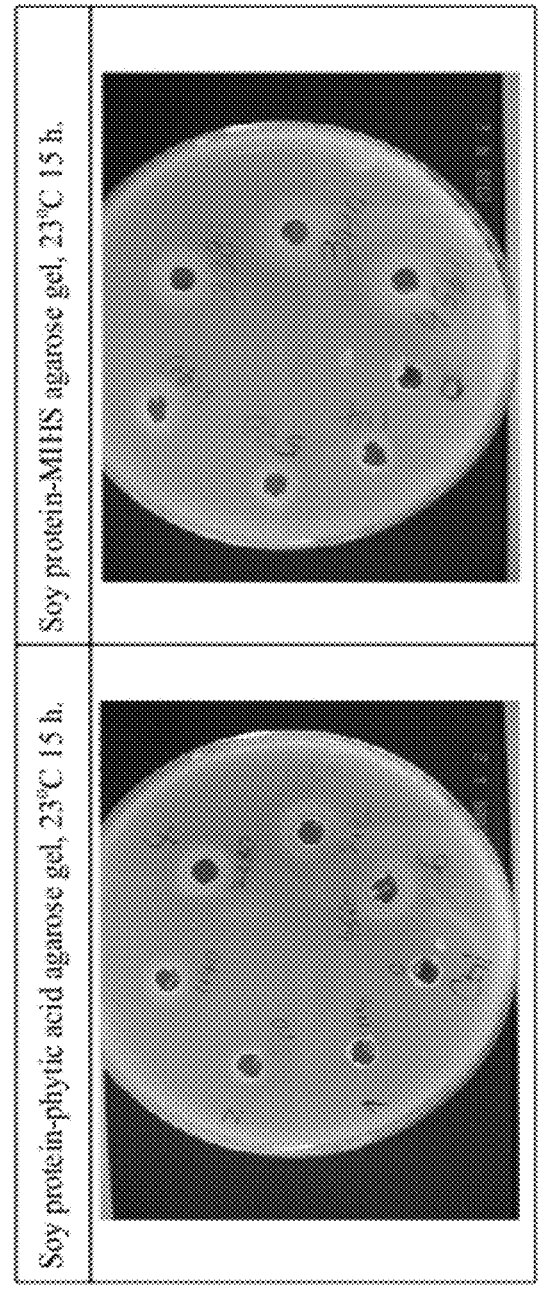
FIG. 18 which is two photographs.

FIG. 18 shows examples of protease assays done by the petri-dish method. The wells contained 0 (control), 114, 570, 1140, 2280, 3420 and 4560 Dan units (or GSU, Genencor Subtilisin Unit).

Figure 19:
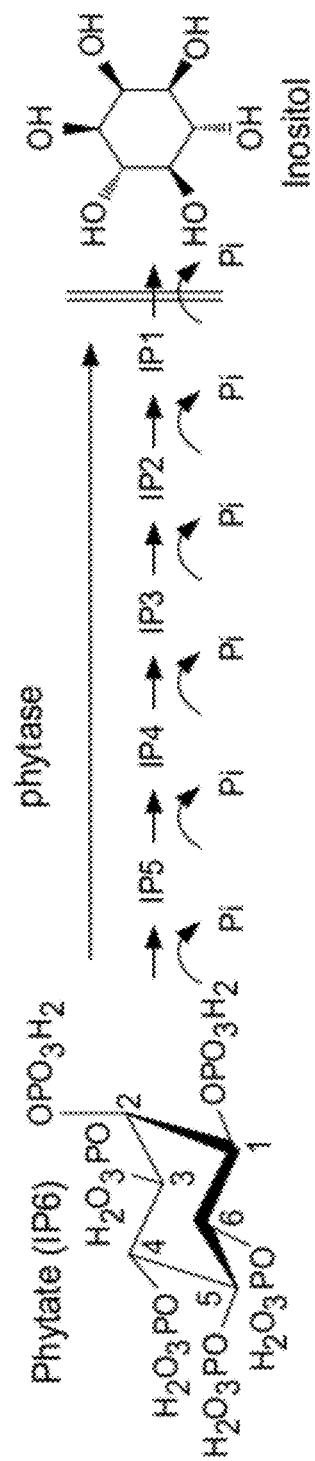
FIG. 19 which is a representation.

FIG. 19 shows a schematic stepwise hydrolysis of phosphate groups from myo-inositol hexakisphosphate (IP6) to myo-inositol pentakisphosphate (IP5), myo-inositol tetrakisphosphate (IP4), myo-inositol trisphosphate (IP3), myo-inositol bisphosphate (IP2) and myo-inositol monophosphate (IP1) with the concomitant liberation of inorganic phosphate at each step. The first step from IP6 to IP5 gives the largest change in turbidity and correlates with the concentration of phytase. However, hydrolysis of the remaining phosphate groups, in particular IP5 to IP4 can also be used to measure phytase activity.

Figure 20A:
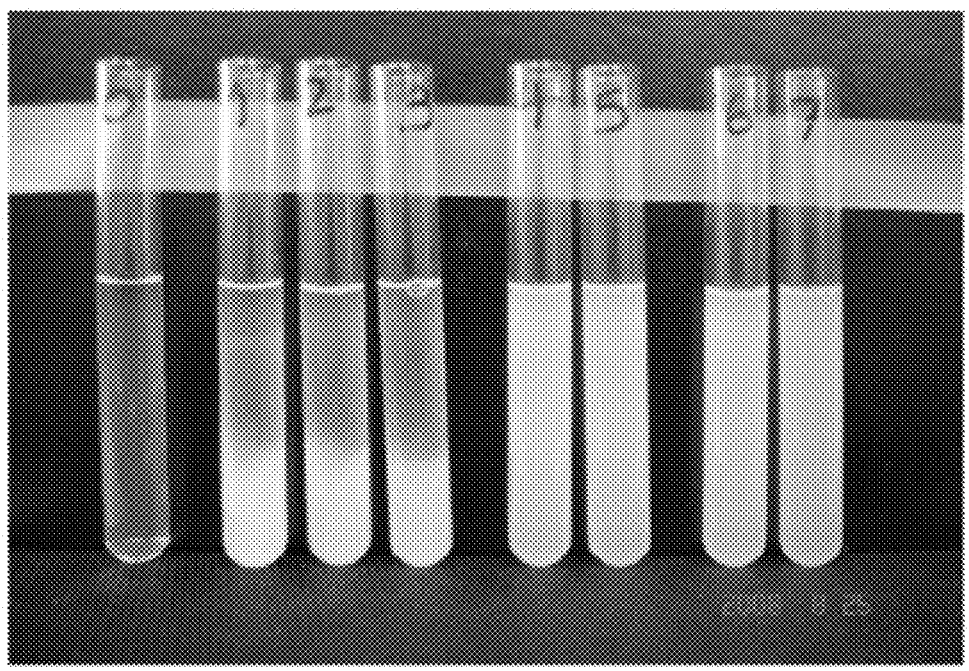
FIG. 20a which is a photograph.

FIG. 20a shows the effect of phytic acid on the aggregation of soy proteins producing turbidity of the solutions and the clearing of the turbid solutions with phytase B from the soil bacterium *Buttiauxella* sp. Tube 0, soy protein only (clear solution). Tubes 1-7, soy protein at 0.15 mg/ml phytic acid (the soy solutions in all tubes are turbid). In tube 1-3 the aggregate starts to precipitate.

Figure 20B:
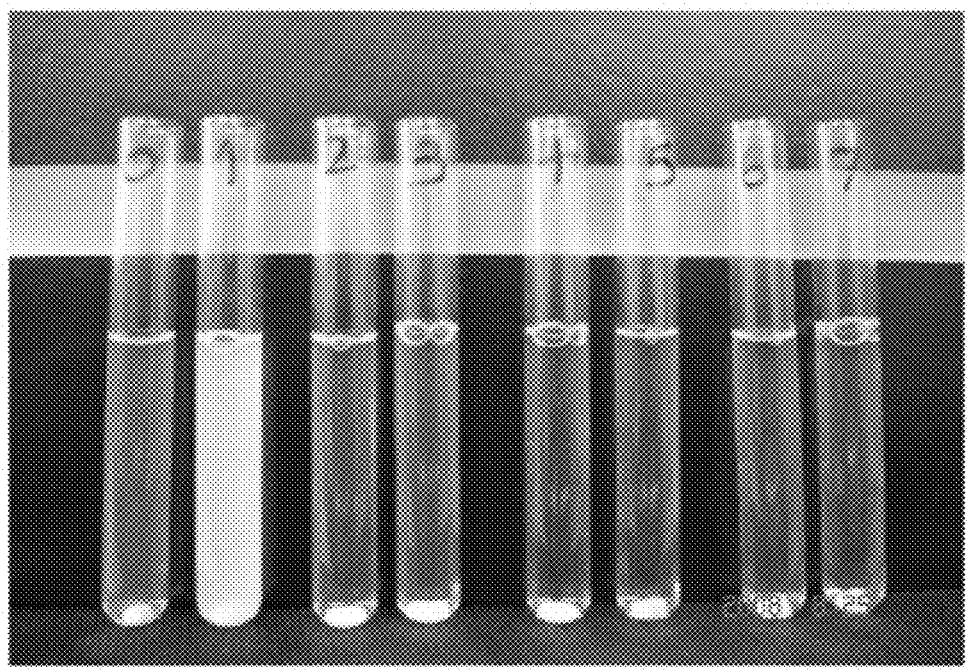
FIG. 20b which is a photograph.

FIG. 20b: Tube 0, soy protein only (clear solution). Tube 1-7, soy protein at 0.15 mg/ml phytic acid/with the addition of phytase B: 0, 5, 10, 50, 100, 200 and 300 FTU/ml. The solution became clear 1 min after the addition of the phytase. As can be seen from FIGS. 20a and 20b, decreases in turbidity can be seen by eye. Turbidity also corresponds to the Absorbance at 600 nm.

Figure 21:
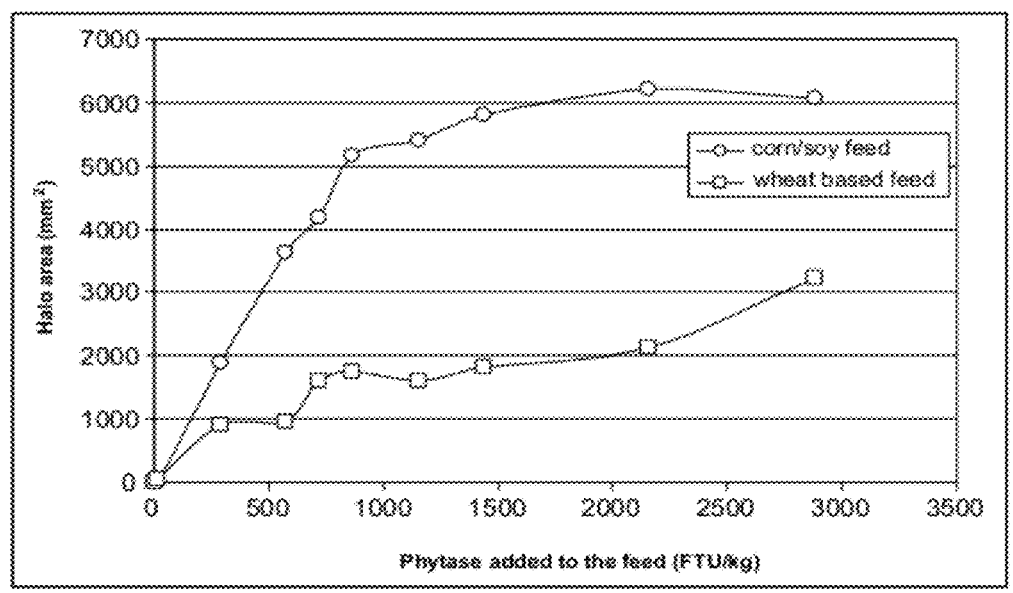
FIG. 21 which is a graph.

FIG. 21 shows the relationship between the size of the halo area and the number of phytase units added to corn/soy or wheat based feed. As can be seen from FIG. 21, the size of the halo produced in a gel-based or Petri-dish assay depends on the type of feed that the sample comes from as well as the number of phytase units and reaction conditions. The results of the assay can be compared to standards or controls to take account of this difference. This is particularly useful in quantitative or semi-quantitative assays. Assays of wheat based feeds can be incubated for a longer time if necessary as the halo develops more slowly. The optimum incubation time may be determined for this test on different types of feed.

Figure 22:
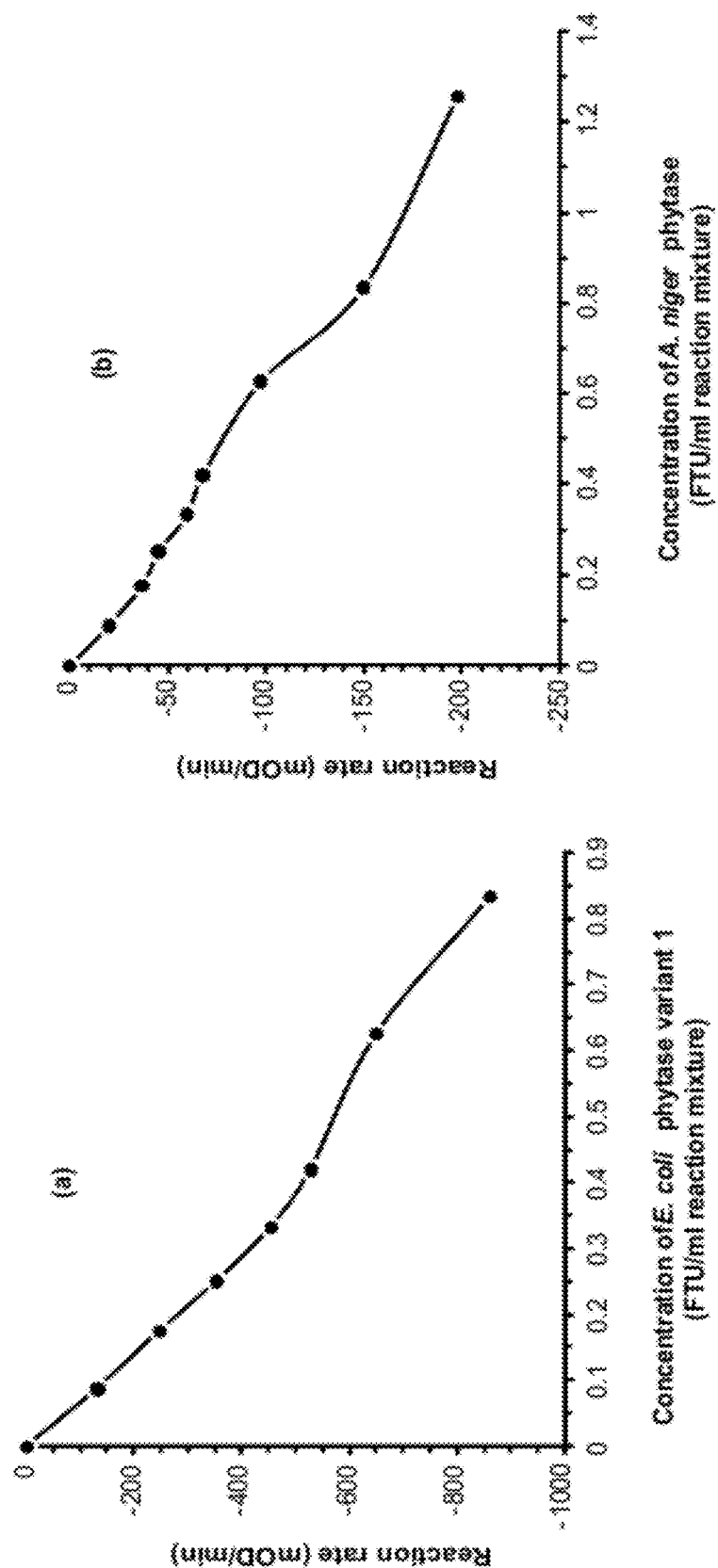
FIG. 22a which is a graph.
FIG. 22b which is a graph.

FIG. 22 shows the effect of phytase concentration on the phytase-catalyzed reaction using phytic acid (IP$_6$)-lysozyme complex as substrate.

Figure 23:
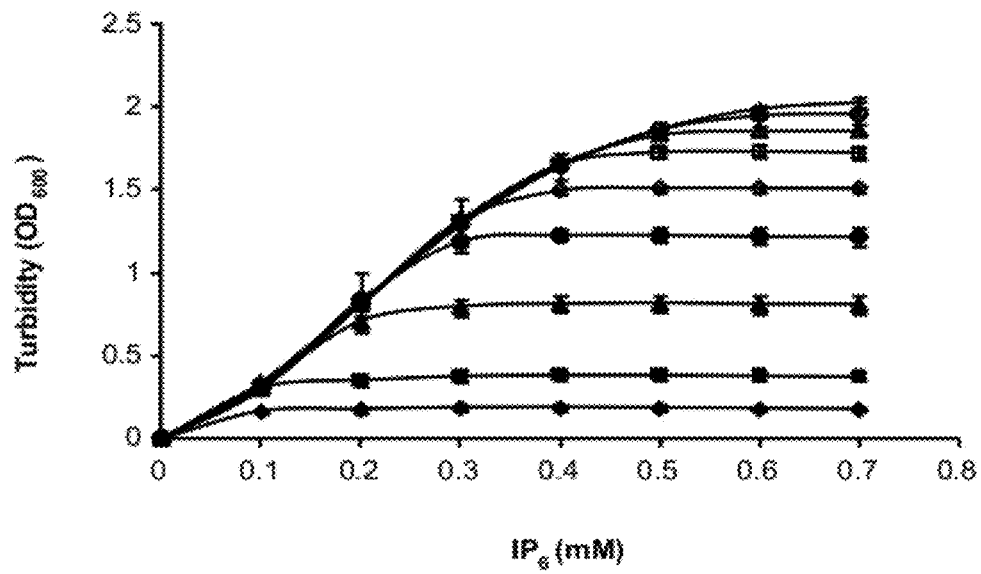
FIG. 23 which is a graph.
Figure 23:
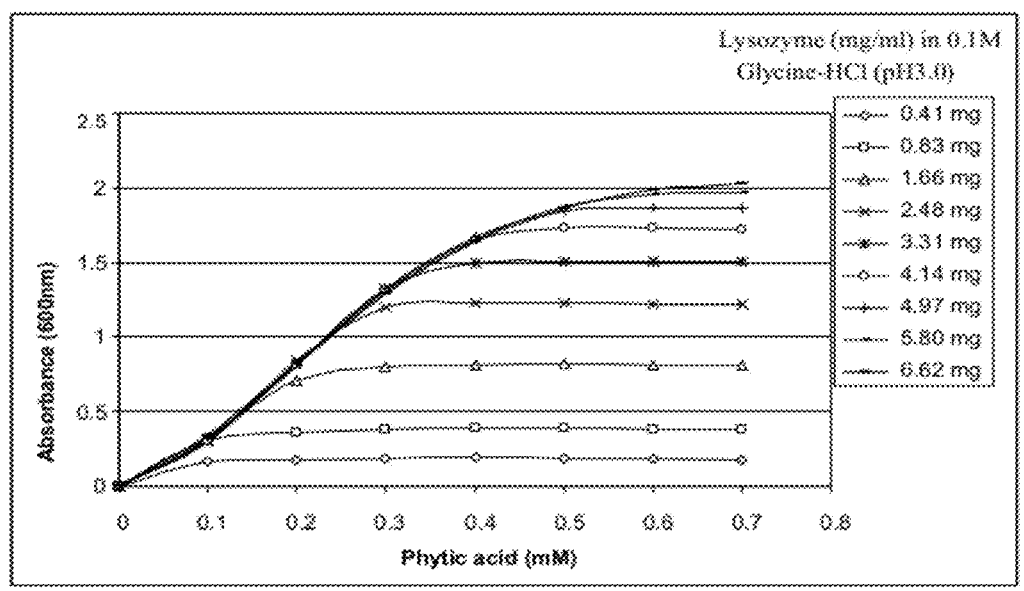

FIG. 23: Effect of IP$_6$ and lysozyme concentration on the turbidity of IP$_6$-lysozyme complex solution. The complex was prepared in 50 mM sodium acetate buffer pH 4 containing 0-0.7 mM IP$_6$ and lysozyme at different concentrations: 30 µM (◆), 58 µM (■), 116 µM (▲), 174 µM (●), 231 µM (◇), 289 µM (□), 347 µM (Δ), 405 µM (○), and 463 µM (+) in a total volume of 120 µl. Experimental details are described in the Materials and Methods section.

Figure 24:
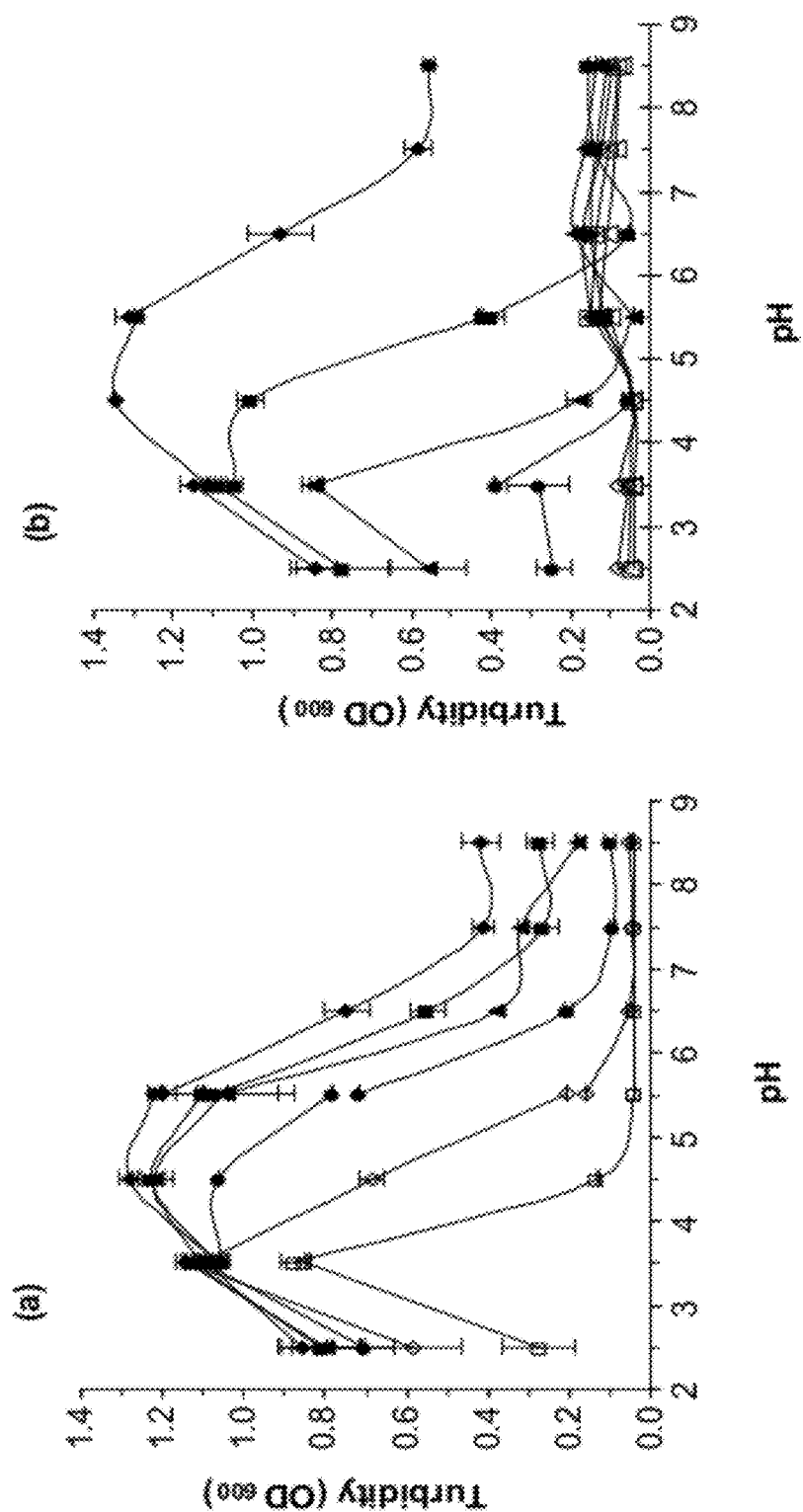
FIG. 24 which is a graph.

FIG. 24: Effect of pH and concentration of (a) NaCl and (b) CaCl$_2$, respectively, on the turbidity of IP$_6$-lysozyme complex (in a ratio of 0.3 mM:0.23 mM) in 50 mM glycine-HCl buffer (pH 2.5-3.5), 50 mM sodium acetate buffer (pH 3.5-5.5), and 50 mM Tris-maleate buffer (pH 5.5-8.5) containing 0.3 mM IP$_6$, 0.23 mM (2.5 mg/ml) lysozyme and (a) NaCl at different concentrations: 0 mM (◆), 5 mM (■), 10 mM (▲), 15 mM (●), 30 mM (◆), and 45 mM (□), or (b) CaCl$_2$ at different concentrations: 0 mM (◆), 1 mM (■), 3 mM (▲), 5 mM (●), 7 mM (◇), 10 mM (□) and 15 mM (Δ) in a total volume of 120 µl. Experimental details are described in the Materials and Methods section.

Figure 25:
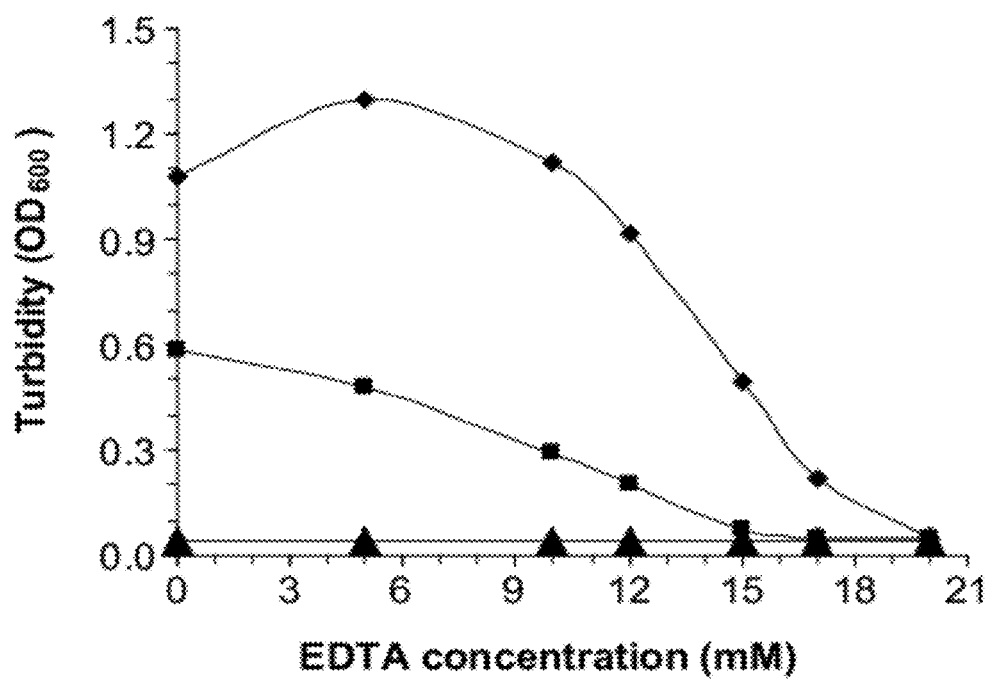
FIG. 25 which is a graph.

FIG. 25: Effect of EDTA and CaCl$_2$ concentrations on the turbidity of IP$_6$-lysozyme complex (0.3 mM:0.23 mM) in 50 mM glycine-HCl pH 3.5 containing 0.3 mM IP$_6$, 0.23 mM lysozyme and CaCl$_2$ at different concentrations: 0 mM (◆), 5 mM (■), and 10 mM (▲) in a total volume of 120 µl.

Figure 26:
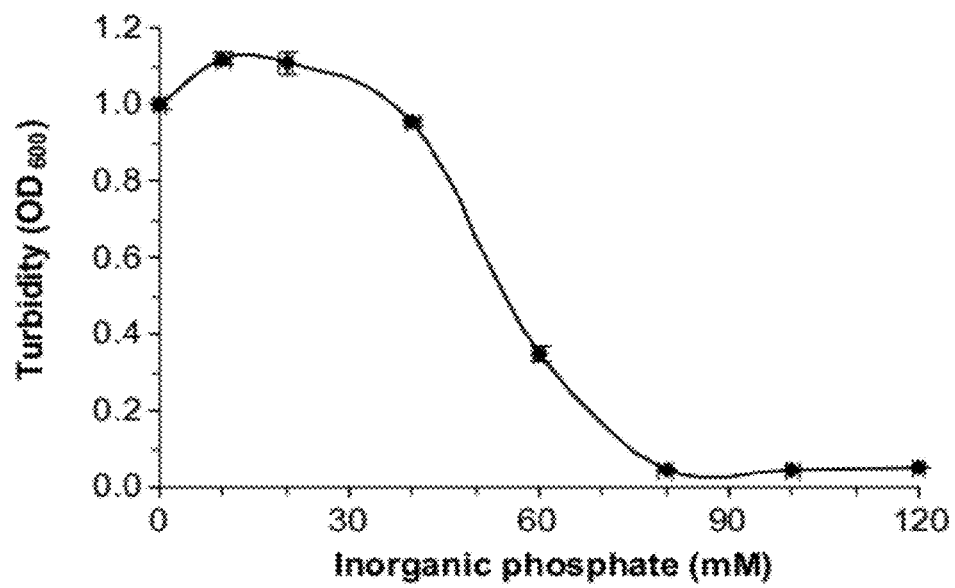
FIG. 26 which is a graph.

FIG. 26: Effect of phosphate concentration on the turbidity of IP$_6$-lysozyme complex (0.3 mM:0.23 mM) in 50 mM glycine-HCl pH 3.5 containing 0.3 mM IP$_6$, 0.23 mM lysozyme and different concentrations of KH$_2$PO$_4$ in a total volume of 120 µl.

Figure 27:
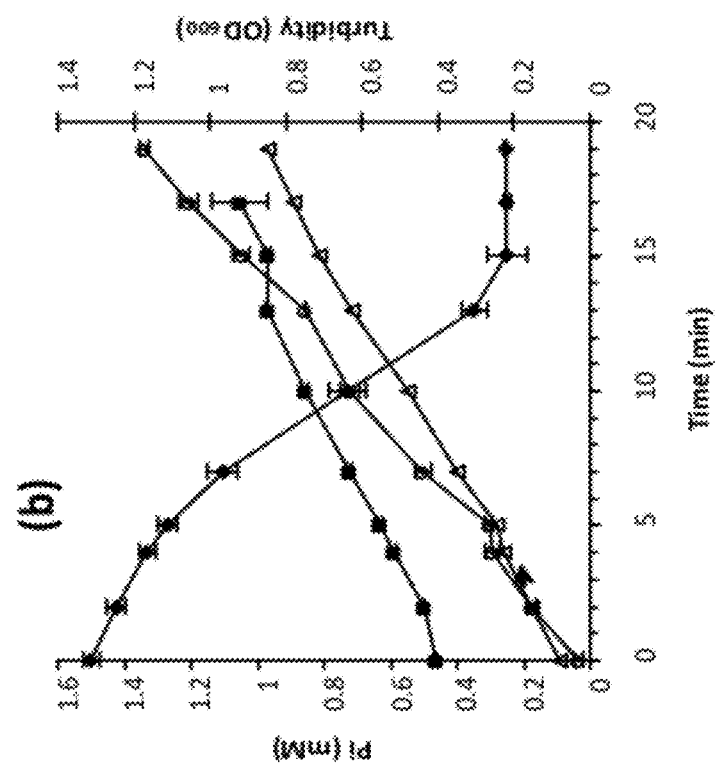
FIG. 27a which is a graph.
FIG. 27b which is a graph.
Figure 27:
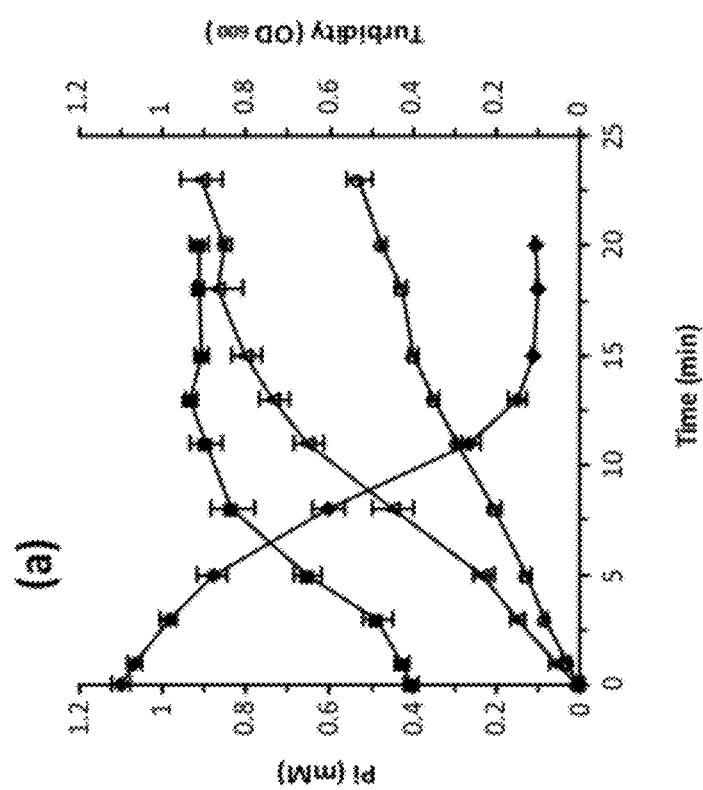

FIG. 27: Activity of (a) *E. coli* phytase variant 1 (0.1 FTU/ml) and (b) *A. niger* phytase (0.5 FTU/ml) with IP$_6$-lysozyme substrate based on turbidity reduction (◆) and P$_i$ released (■); with IP$_6$ based on P$_i$ released (Δ); and with IP$_6$-lysine complex based on P$_i$ released (o). The three substrates were prepared in 50 mM glycine-HCl (pH 3.5) containing 0.3 mM IP$_6$ (for IP$_6$ substrate) and either lysozyme 0.23 mM (for IP$_6$-lysozyme substrate) or lysine 23 mM (for IP$_6$-lysine substrate) in a total volume of 120 µl. Reactions were performed at 37° C. for 25 min with continuous mixing. Turbidity of the reactions was determined every 30 sec. For Pi determination, the reactions were stopped by adding 30 µl of 2.5 M HCl, centrifuged and the supernatants were analyzed for P$_i$ on Konelab.

Figure 28:
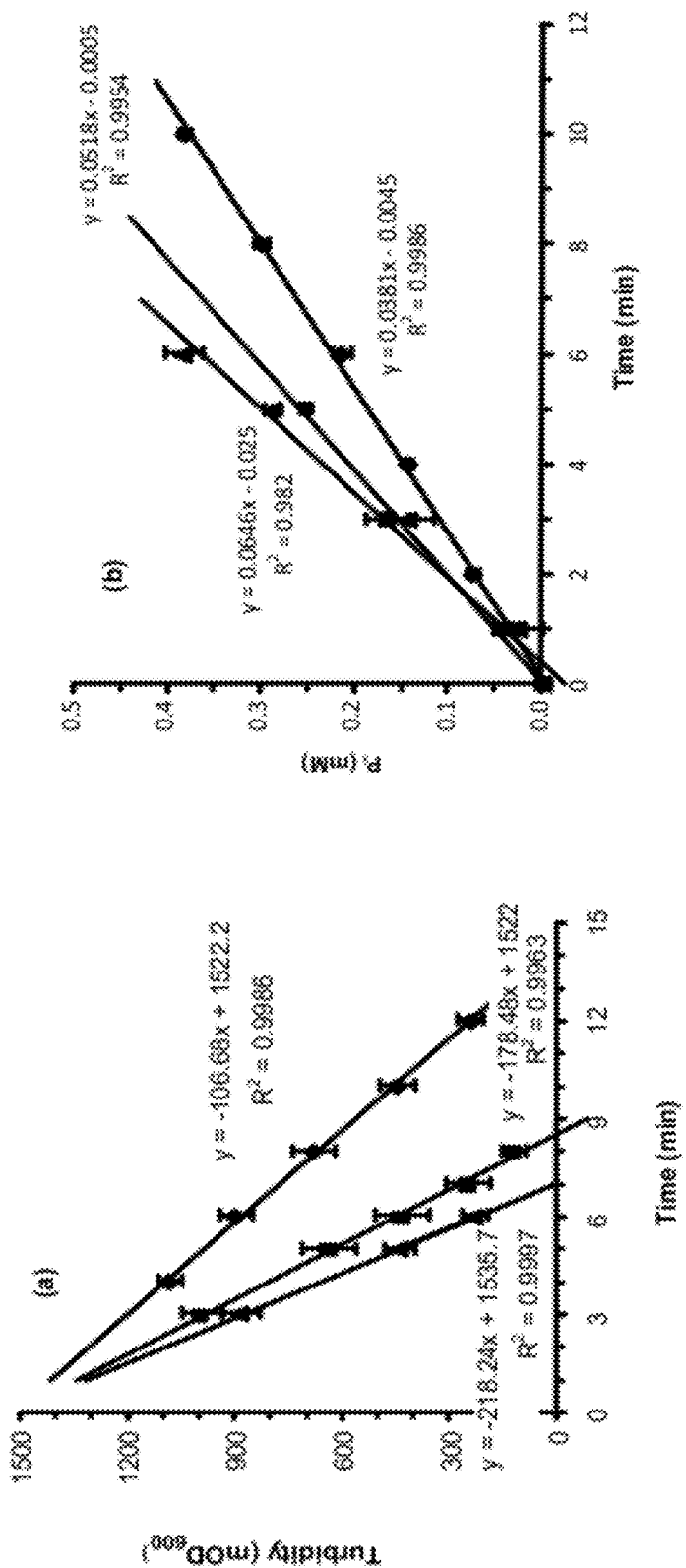
FIG. 28a-f is a series of graphs.
Figure 28:
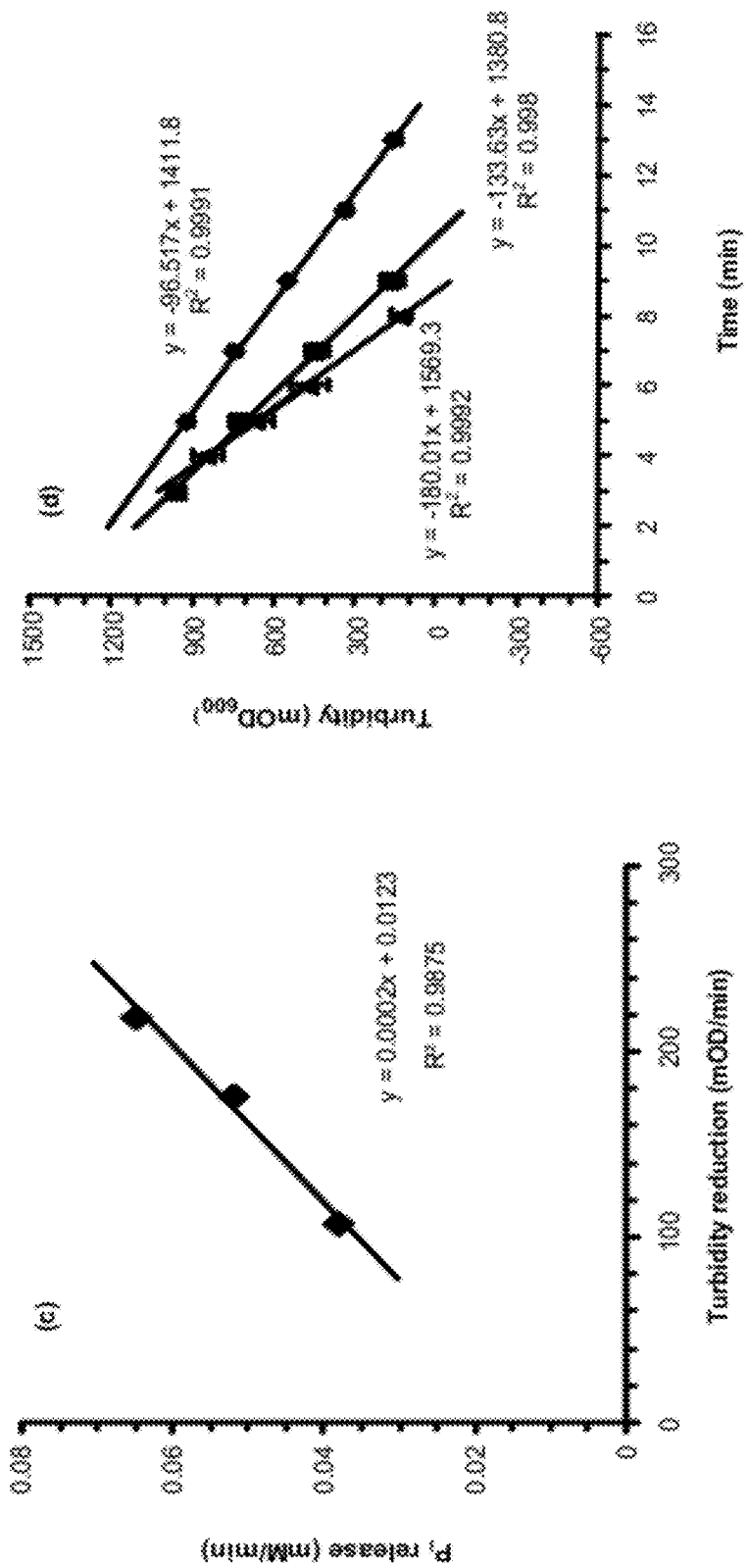
Figure 28:
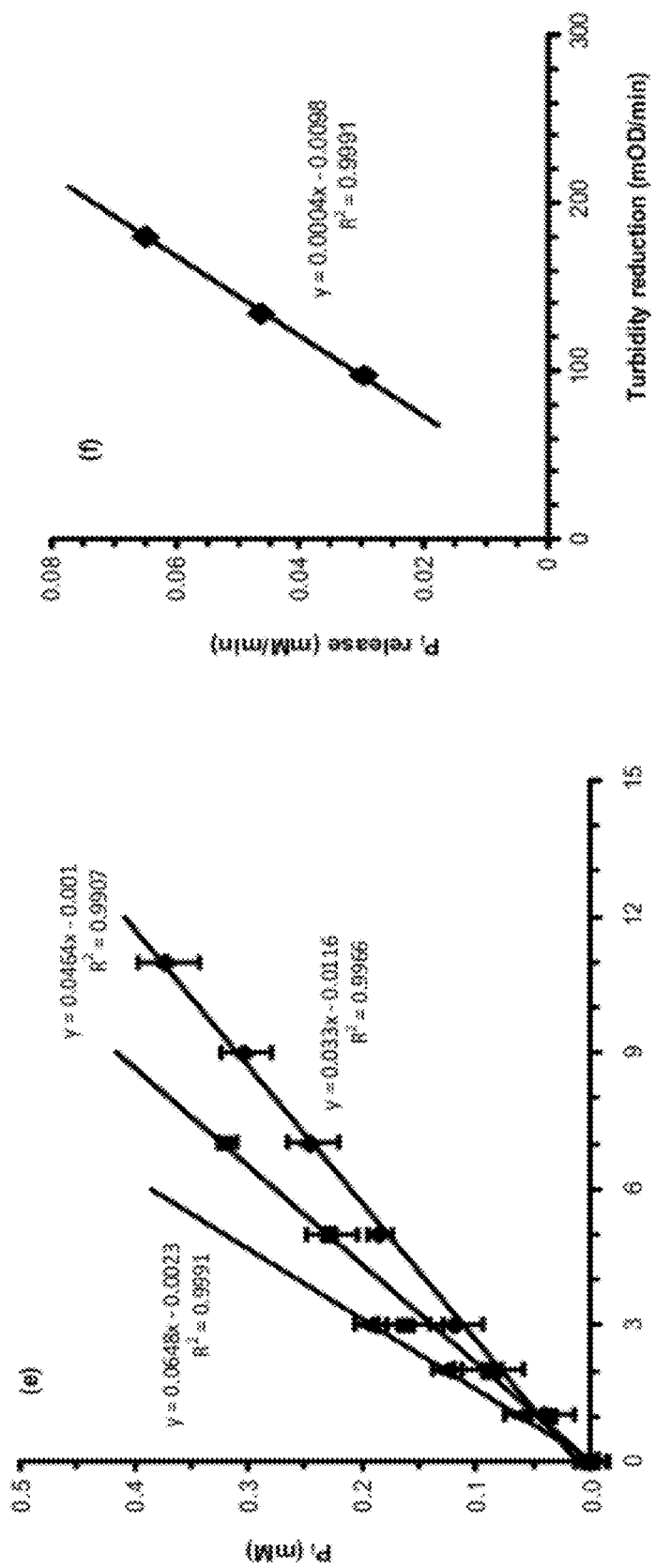

FIG. 28: Relationship between turbidity reduction and phosphate release during reaction with different concentrations of phytases: (a, b, c) *E. coli* phytase variant 1, 0.1 FTU/ml (♦), 0.2 FTU/ml (■), and 0.3 FTU/ml (▲), and (d, e, f) *A. niger* phytase, 0.1 FTU/ml (♦), 0.15 FTU/ml (■), and 0.2 FTU/ml (▲), in 50 mM acetate buffer (pH 5.5 at 37° C.) with a total reaction volume of 120 µl. Turbidity measurements are shown in FIG. 28*a*, FIG. 28*d*; P$_i$ released in FIG. 28*b* and FIG. 28*e*; and relationship between turbidity reduction (mOD/min) and P$_i$ release (mM/min) in FIG. 28*c* and FIG. 28*f*.

Figure 29:
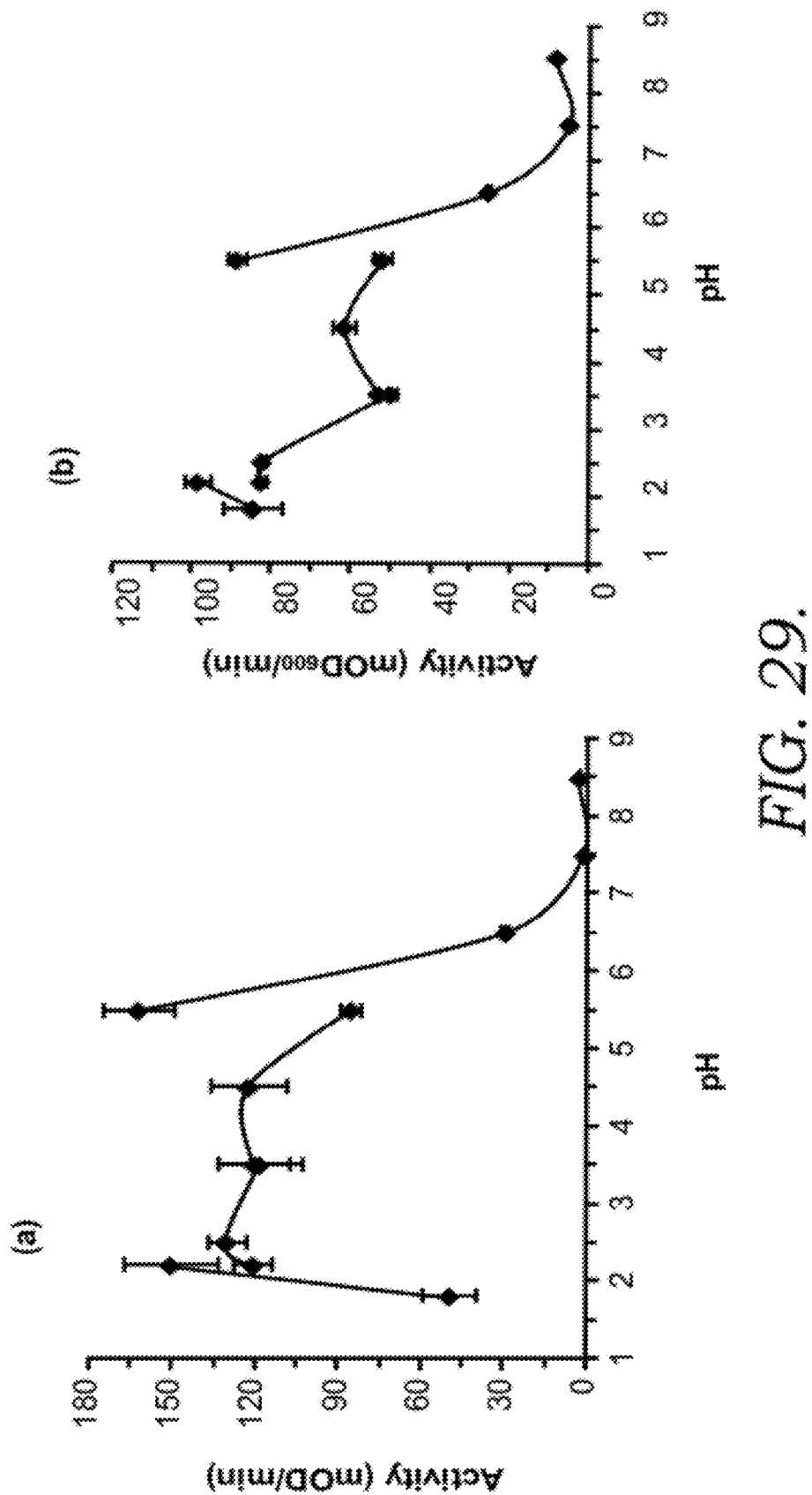
FIG. 29a-e is a series of graphs.
Figure 29:
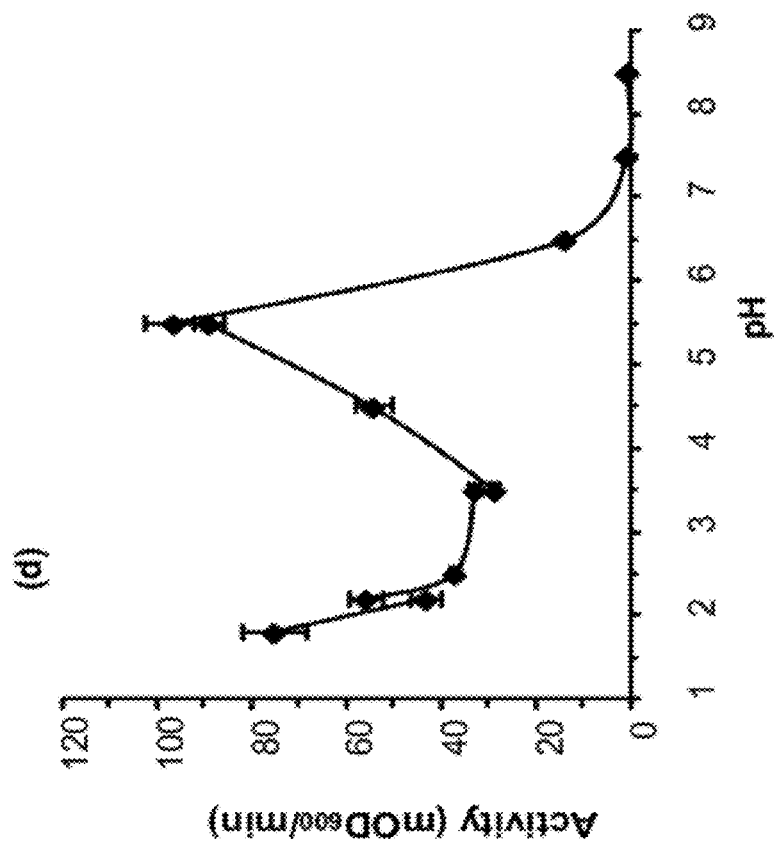
Figure 29:
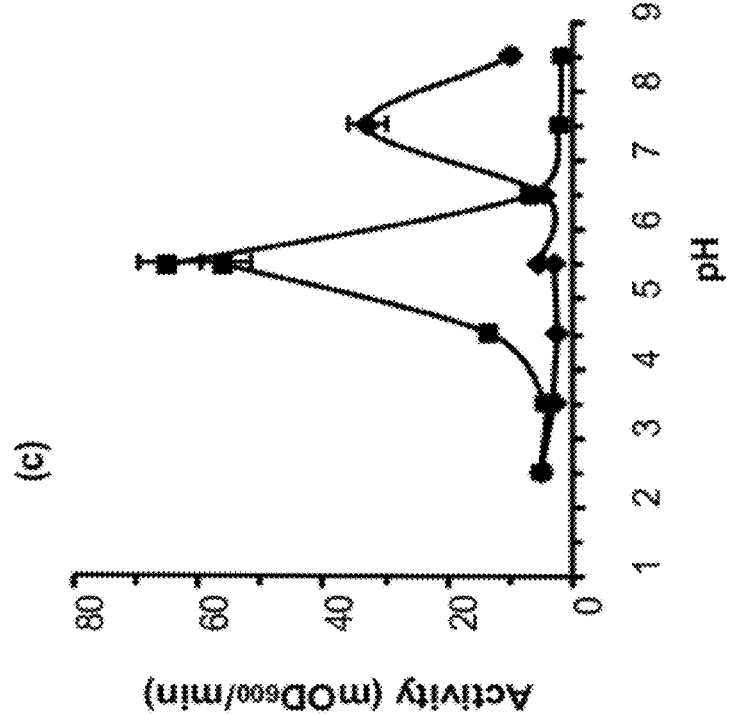
Figure 29:
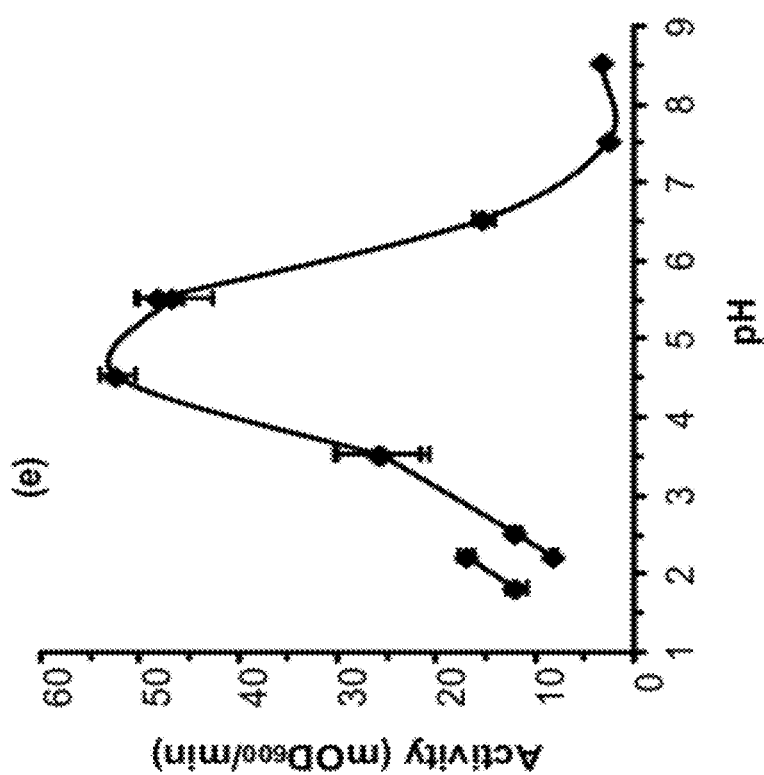

FIG. 29: pH profiles of (a) *E. coli* phytase variant 1, (b) *E. coli* phytase variant 2, (c) *Bacillus* phytase, (d) *A. niger* phytase, and (e) *Peniophora lycii* phytase on IP$_6$-lysozyme substrate complex. Reactions were carried out in 50 mM potassium-HCl (pH 1.5-2.5), 50 mM glycine-HCl (pH 2.5-3.5), 50 mM sodium acetate (pH 3.5-5.5) and 50 mM Tris-maleate (pH 5.5-8.5), respectively, containing 0.3 mM IP$_6$ and 0.23 mM lysozyme in a total volume of 120 µl at 37° C. The enzyme dose for each reaction was 0.1 FTU/ml based on P$_i$ released from IP$_6$ in conventional phytase activity assay. In FIG. 7*c*, enzymatic reactions were performed without CaCl$_2$ (♦) and with 1 mM CaCl$_2$ (■).

DETAILED ASPECTS OF THE PRESENT INVENTION

In one broad aspect, the present invention relates to a method of detecting a phytase activity or a protease activity comprising the steps of:
(a) providing a composition comprising a phytate/protein complex in a liquid or a gel;
wherein the phytate/protein complex provides a detectable property to the composition;
(b) providing a sample that comprises or is suspected of comprising phytase activity and/or protease activity, wherein the phytase and/or protease activity is capable of causing a change in the detectable property of the composition;
(c) contacting the composition with the sample;
(d) determining if there is a detectable change in detectable property of the composition.

In another broad aspect, the present invention provides a method for detecting an enzymatic activity comprising the steps of:
(a) providing a medium comprising a continuous and a disperse phase,
wherein the disperse phase comprises:
 i) a first component which is a polyvalent component, and
 ii) a second component which is an ionic component,
wherein the polyvalent component and the ionic component are held together by one or more intermolecular interactions to form the disperse phase,
wherein the disperse phase provides a detectable property to the medium;
(b) providing a sample that comprises or is suspected of comprising the enzymatic activity,
wherein the enzymatic activity is capable of affecting the disperse phase to cause a detectable change in the detectable property of the medium;
(c) contacting the medium with the sample;
(d) determining if there is a change in the detectable property of the medium.

The present invention provides a useful assay method for determining whether a feed comprises a particular enzymatic activity, preferably phytase. By knowing whether a feed has no or low levels of phytase it is possible to then add phytase to a feed. This is advantageous as the phytase breaks down normally non-nutritional phytate to nutritional phosphate entities.

Detecting enzyme activity means obtaining an indication of the presence or absence of enzyme activity or of the amount of activity of an enzyme.

The method for detecting enzyme activity may be a quantitative, semi-quantitative or qualitative method. In one embodiment the assay may provide an indication of the presence or absence of enzyme activity. In another embodiment the method may provide an indication of the amount of enzyme activity in a sample.

Enzyme activity means the ability to catalyse a particular reaction. The amount of substrate consumed or product produced from the reaction may be observed or measured.

The amount of inhibition of enzyme activity may be measured by comparing the amount of activity expected from a known amount of enzyme in a sample with the amount of enzyme activity measured.

Phytic acid (myo-inositol hexakisphosphate, IP$_6$) is an important constituent in, for example, cereals, legumes and oilseed crops. The salt form, phytate, is the major storage form of phosphorous in these plants. Phytases are useful as additives to animal feeds where they improve the availability of organic phosphorus to the animal and decrease phosphate pollution of the environment (Wodzinski R. J., (1996)). Animals do not naturally produce enzymes for breaking down phytate to obtain phosphate for bone building and growth. The activity of plant phytases vary with plant species and variety and many plant phytases do not have optimum activity at the pH found in animal digestive systems. Phytases may be heat-inactivated during the feed pelleting process or phytase activity may decrease during storage. It is therefore advantageous to be able to test for the presence, absence or amount of phytase activity in feed, food or feed ingredient samples.

In one embodiment of the present invention the enzyme activity may be a phosphohydrolase or a phosphomonoesterase, preferably a phytase activity.

As used herein, the term phytase activity refers to the ability of an enzyme or a sample to catalyse the steps in the decomposition of phytate (myo-inositolhexakisphosphate) to give inorganic phosphate (e.g. orthophosphate). The steps are shown in FIG. 19.

The term phytase means a protein or polypeptide which is capable of catalysing the hydrolysis of esters of phosphoric acid, including phytate and releasing inorganic phosphate, myo-inositol hexakisphosphate+H$_2$O<=>1D-myo-inositol 1,2,3,5,6-pentakisphosphate+phosphate (E.C.3.1.3.26). Some phytases in addition to phytate, are capable of hydrolysing at least some of the inositol-phosphates of intermediate degrees of phosphorylation which results in the stepwise formation of myo-inositol pentakis-, tetrakis-, tris-, bis- and monophosphates, as well as the liberation of inorganic phosphate. Some of these enzymes are, histidine acid phosphatase (HAP), pH 2.5 acid phosphatase, beta-propeller phytase (BPP) and purple acid phosphatase phytase (PAP), for example, 3-phytase (E.C.3.1.3.8), 4-phytase (also referred to as 6-phytase, E.C.3.1.3.26), or 5-phytase (E.C.3.1.3.72), also neutral phytases and alkaline phytases (mainly from Bacilli) as classified in accordance with the Nomenclature Committee of the International Union of Biochemistry and Molecular Biology (IUBMB).

In one embodiment preferably the polyvalent component of the disperse phase is myo-inositol hexakisphosphate and the phytase activity hydrolyses myo-inositol hexakisphosphate to myo-inositol pentakisphosphate. The hydrolysis of myo-inositol hexakisphosphate to myo-inositol pentakisphosphate provides a change in the detectable property of the medium, for example a detectable change in turbidity.

In another embodiment the polyvalent component of the disperse phase may be myo-inositol pentakisphosphate and the hydrolysis activity hydrolyses myo-inositol pentakisphosphate to myo-inositol tetrakisphosphate.

In another embodiment the polyvalent component of the disperse phase may be an inositol-phosphate of intermediate degree such as myo-inositol pentakis-, tetrakis-, tris-, bis- or monophosphate and the hydrolysis activity removes one phosphate which results in the step-wise formation of myo-inositol tetrakis-, tris-, bis- and monophosphate or inositol.

In another embodiment a combination of enzymes may be added to a sample or to a feed, food, feed ingredient, feed ingredient mixture (premix) or food ingredient to catalyse the hydrolysis of myo-inositol monophosphate (IP1) to Inositol.

Phytase activity may be measured in Phytase Units (FTU). One FTU is defined as the activity of phytase that generates 1 micromole of inorganic phosphorus per minute from 5.1 mM of sodium phytate at pH 5.5 and 37° C.

In some circumstances, the number of phytase units measured in a sample may not correlate with the amount of phytase enzyme because phytase inhibitors may be present. Therefore, preferably suitable controls comprising a known amount of phytase may be used to check for the presence and amount of phytase inhibitors in the sample.

In another embodiment the enzymatic activity of the present invention may be protease activity. As used herein protease activity is the ability to catalyse the hydrolysis of peptide bonds in proteins or peptides to release shorter peptide chains or amino acids. Suitably the protease is an endoprotease from microbes, plants or other living organisms.

Suitably the protease is capable of hydrolysing lysozyme, β-casein and/or soy protein.

In one embodiment the method may be used for detecting the presence, absence or amount of enzymatic activity, suitably protease or phytase activity in a sample. The sample may be an aqueous enzyme solution or a complex sample such as a sample of a feed, food, feed premix, feed ingredient or food ingredient or an extract of a feed, food, feed ingredient or food ingredient. Suitably the feed ingredient or feed premix may comprise or consist of a micro organism. Suitably the feed may be a cereal based, e.g., corn/soy based feed or a wheat based feed. Suitably an extract of a feed, food, feed premix, feed ingredient or food ingredient may be an aqueous extract.

The protein in the disperse phase of the present invention may be any protein provided that it is capable of forming an intermolecular interaction with the polyvalent component to form a disperse phase. Where the method, use or kit is a method, use or kit for detecting protease activity the protein must also be capable of being hydrolysed by the protease of interest to destroy the disperse phase.

Suitably the protein may be a naturally occurring protein or a synthetic protein with pI values preferably above pH 4.6, such as soy protein, rapeseed protein, mustard protein, bovine β-casein, N,N-dimethylated casein (C9801), bovine beta-lactoglobulin, bovine serum albumin, lysozyme, or porcine haemoglobin. The protein may be modified with a chromophore for example, a chromophore or a fluorophore.

As used herein the term ionic component means any charged component, preferably a multiple charged ion. The ionic component of the present invention may be any ionic component provided that it is capable of forming an intermolecular interaction with the polyvalent component of the present invention to form a disperse phase. In one embodiment the ionic component may be a protein or a fatty acid or a fatty acid with calcium ions.

Where the method, use or kit is a method, use or kit for detecting enzyme-catalysed hydrolysis of the ionic component the ionic component must be capable of being hydrolysed by the enzyme of interest to destroy the disperse phase by intramolecular hydrolysis within the ionic component rather than by disruption of the intramolecular interaction. The disperse phase is destroyed when it no-longer provides a detectable property to the medium or there is a change in the detectable property that the disperse phase provides to the medium.

Where the enzyme of interest is a phytase the polyvalent component may suitably be phytic acid (myo-inositol hexakisphosptate, IP6), myo-inositol pentakisphosphate IP5, or polyphosphate.

Where the enzyme of interest is a protease the polyvalent component may suitably be phytic acid (myo-inositol hexakisphosptate, IP6), MIHS (myo-inositol hexasulphate), myo-inositol pentakisphosphate, or polyphosphate.

The disperse phase of the present invention comprises at least one protein or peptide and at least one polyvalent component. In one embodiment the disperse phase may be a complex or an aggregate. In one embodiment the disperse phase may be a semisolid or a solid.

In one embodiment the disperse phase is an aggregate or a complex, such as an aggregate of protein and phytate or a protein-phytate complex.

In one embodiment the disperse phase is provided dispersed in a continuous phase to form a medium comprising a disperse phase and a continuous phase. The continuous phase may be a liquid or a gel, suitably an aqueous liquid or an aqueous gel, suitably an agar gel or an agarose gel or a polyacrylamide gel or a gel formed with another gel forming polymer. The presence of the disperse phase in the continuous phase provides a detectable property to the medium such as turbidity, viscosity, absorbance of light or scattering of light. This detectable property can be measured with reference to a sample of the continuous phase that does not comprise the disperse phase. The amount of turbidity, viscosity, absorbance of light or scattering of light by the medium is proportional to the amount of disperse phase in the medium.

Destroying or degrading one or both of the partners in the disperse phase, i.e. the first component which is a polyvalent component, for example IP6 (=$IP_6$) or the second component which is an ionic component, for example a protein, by hydrolysis of the IP6, for example by phytase, or hydrolysis of the protein by protease will lead to destruction of the disperse phase. Destruction of the disperse phase leads to a decrease in turbidity, viscosity or absorbance of the medium which is directly proportional to the activity of the enzyme.

In some embodiments the enzymatic activity is phytase activity and the polyvalent component is preferably IP6.

Complexes of protein with IP6 provide higher absorbance at 600 nm than complexes of other phosphate esters and IP5 positional isomers. Therefore the change in absorbance at 600 nm is greater with hydrolysis of 1 inorganic phosphate group from IP6 than from other phosphate esters and IP5 positional isomers.

Components of the disperse phase of the present invention may be held together by intermolecular interactions such as charge-charge interactions (electrostatic interactions) or hydrogen bonding.

In one embodiment the protein is at a pH below its isoelectric point (pI) and is positively charged. Preferably, in this instance, the polyvalent component is negatively charged, for example IP6, and these two components form a charge-charge interaction between the positively charged protein and the negatively charged IP6. The charge-charge interaction leads to the formation of the disperse phase.

In one embodiment the medium or the protein is at between pH 1.8 and pH 7.5, preferably between pH 1.8 and pH 5.5.

In another embodiment the polyvalent component is phytic acid or a component of a phytate salt. In a further embodiment the enzyme is a phytase.

In another embodiment the protein is at a pH which is above its pI and is negatively charged. Preferably, in this instance, the polyvalent component is positively charged, for example polylysine, chitin, chitosan or an oligomer of chitin or chitosan. These two components form a complex by charge-charge interaction between the negatively charged protein and the positively charged polyvalent component.

In another embodiment the protein is above its pI and is negatively charged and the polyvalent component is also negatively charged. These two negatively charged components form a disperse phase with each other by charge-charge interaction with positively charged monovalent or divalent or trivalent cations.

As used herein a monovalent cation is any positively charged ion having only one positive charge, for example, $Na^+$ or $K^+$, a divalent cation is any positively charged ion having two positive charges, for example, $Ca^{2+}$, $Mg^{2+}$, $Zn^{2+}$. $Fe^{3+}$, a trivalent cation is any positively charged ion having three positive charges, for example, $Fe^{3+}$.

The amount of disperse phase in a solution or gel is proportional to the turbidity, absorbance or light scattering of the solution or gel or the viscosity of a solution. An indication of the amount of disperse phase in the solution or gel can therefore be obtained by measuring the turbidity, absorbance or light scattering of the solution or gel or the viscosity of a solution by any suitable technique known in the art.

The amount of disperse phase in the solution or gel after addition of the enzyme or sample depends on the amount of enzyme activity. The presence, absence or amount of enzyme activity can be determined by the difference in turbidity, absorbance or light scattering of the solution or gel or the viscosity of a solution before and after addition of the enzyme or sample or with and without addition of the enzyme or sample.

In one embodiment turbidity can be observed by eye or using a turbidimeter. Turbidity of solutions can be seen by eye in cuvettes or tubes as shown in FIG. 6, top left hand panel or can be measured using a turbidimeter. Turbidity of gels can also be seen by eye—for example as proven in FIGS. 13, 14 and 17. Turbidity of solutions in microplates can be seen by eye or measured using a microplate reader suitable for high through-put screening.

In another embodiment the amount of disperse phase in solution is measured by the absorbance of light of the solution, suitably the absorbance of light can be measured at any wavelength between 200 and 800 nm, preferably between 350 and 700 nm more preferably at between 400 and 600 nm and most preferably at 600 nm. Absorbance of many samples can be analysed and/or compared on a microplate by using an ELISA reader or microplate reader.

In one embodiment the signal provided by destruction or degradation of the disperse phase can be amplified by using a protein that is labelled covalently or non-covalently with a fluorescence probe, which changes its fluorescence intensity with the change of viscosity of the solution or when the protein forms part of a complex, aggregate or dispersed phase. The protein may also be labelled with a chromophore, suitably a fluorophore.

In one aspect the present invention relates to a method for detecting phytase activity comprising the steps of: (a) providing a medium comprising a continuous and a disperse phase, wherein the disperse phase comprises: i) phytic acid, or its derivatives, and ii) an ionic component, for example a protein, wherein the ionic component has at least one positively charged group, or wherein the medium is below the pI of the protein and ionic component, for example the protein, and the phytic acid are held together by one or more intermolecular interactions to form the disperse phase, wherein the disperse phase provides turbidity, viscosity or fluorescence to the medium; (b) providing a sample that comprises or is suspected of comprising phytase activity, wherein the phytase activity is capable of affecting the disperse phase to cause a detectable change in the turbidity, viscosity or the fluorescence of the medium; (c) contacting the medium with the sample; (d) determining if there is a detectable change in the turbidity, absorbance, viscosity or the fluorescence of the medium.

In one embodiment, the phytic acid is IP6 and the phytase activity hydrolyses the IP6 to IP5. In this embodiment the hydrolysis of IP6 to IP5 degrades the disperse phase. In one embodiment the disperse phase provides turbidity to the medium and hydrolysis of IP6 to IP5 causes a detectable decrease in turbidity of the medium. Advantageously phytase activity may be detected from they hydrolysis of IP6 to IP5, which causes a detectable decrease in turbidity of the medium. Because a detectable decrease in turbidity of the medium is observable from the hydrolysis of IP6 to IP5 the change in turbidity happens in a short time (10-60 minutes). The method of the present invention may provide a rapid kinetic assay method for phytase activity. In another embodiment the phytase activity hydrolyses IP5 to IP4 or IP6 to IP5 then IP4. The hydrolysis of IP5 to IP4 or IP6 to IP5 then IP4 causes a detectable decrease in turbidity of the medium.

In one embodiment the method, use or kit of the present invention may be carried out in the absence of antibodies.

In one embodiment the method, use or kit of the present invention may be carried out in solution on a microtitre plate. Advantages of this embodiment are that small amounts of sample may be used, the plate may be read simply and accurately using a microplate reader. This embodiment may be used for quantitative, semi-quantitative or qualitative assays, advantageously quantitative assays may be done with controls on the same microtitre plate.

In another embodiment the method, use or kit of the present invention may be carried out in a gel in a suitable container, for example a petri-dish. In this embodiment the method may be quantitative, semi-quantitative or qualitative, advantageously qualitative assays may be done with areas of the gel that have not been exposed to the enzyme or sample acting as controls. In this embodiment the gel comprises a disperse and a continuous phases. The gel may be turbid. A number of holes or wells may be made in the gel to which samples and controls may be added. Clear patches or halos in the gel appear around the wells containing enzyme activity, preferably phytase or protease activity, the halos develop (expand) with time (halo diameter or size increases kinetically with time).

Advantageously, where the disperse phase consists essentially of phytate-protein complexes the disperse phase may be degraded either by a protease or a phytase. The same medium comprising a protein-phytate complex (disperse phase) in a liquid or gel (continuous phase) may be used either for a protease or a phytase assay. This avoids the need for two separate assays or assay substrates, one for phytase assays and one for protease assays. Advantageously a kit may be produced comprising a medium that is turbid because it comprises protein-phytate complexes and this can be used to perform an assay for either protease activity or phytase activity.

In one embodiment, the ratio of the phytic acid to the protein in the complex (disperse phase, for example a phytate-protein complex or aggregate) is in the range of from 1-100:1-100.

For some embodiments, the ratio of the phytic acid to the protein in the complex (disperse phase, for example a phytate-protein complex or aggregate) is in the range of from 1-100:1-90, 1-100:1-80, 1-100:1-70, 1-100:1-60, 1-100:1-50, 1-100:1-40, 1-100:1-30, 1-100:1-20, 1-100:1-10, 1-100:1-5, 1-100:1. For such embodiments, examples of a preferred ratio of the phytic acid to the protein in the complex are in the range of from 1-100:1, 1-70:1, 1-60:1, 1-50:1, 1-40:1, 1-30:1, 1-20:1, 1-10:1, 1-5:1, 1:1. For such embodiments, a preferred ratio of the phytic acid to the protein in the complex is about 70:1, 60:1, 50:1, 40:1, 30:1, 20:1, 10:1, 5:1 or 1:1. For such embodiments, a preferred ratio of the phytic acid to the protein in the complex is about 60:1.

In some preferred embodiments, the ratio of the phytic acid to the protein in the complex (disperse phase, for example a phytate-protein complex or aggregate) is in the range of from 1-90:1-100, 1-80:1-100, 1-70:1-100, 1-60:1-100, 1-50:1-100, 1-40:1-100, 1-30:1-100, 1-20:1-100, 1-10:1-100, 1-5:1-100, 1:1-100. For such embodiments, examples of a preferred ratio of the phytic acid to the protein in the complex are in the range of from 1:1-100, 1:1-70, 1:1-60, 1:1-50, 1:1-40, 1:1-30, 1:1-20, 1:1-10, 1:1-5, 1:1. For such embodiments, a preferred ratio of the phytic acid to the protein in the complex is about 1:70, 1:60, 1:50, 1:40, 1:30, 1:20, 1:10, 1:5 or 1:1.

Examples of a preferred ratio of the phytic acid to the protein in the complex (disperse phase, for example a phytate-protein complex or aggregate) are in the range of from 1:6-1:100, preferably 1:20-1:70, more preferably 1:45-1:55, more preferably 1:50. In another embodiment the ratio of the phytic acid to the protein in the aggregate or complex is 1:6-1:100, preferably 1:10-1:70, more preferably 1:15-1:30, more preferably 1:15.

In one embodiment the phytic acid concentration is 0.1-0.3 mM. This is lower than the concentration used in other assays that measure release of inorganic phosphate. It is also at least 10 times lower then the phytate found in many cereals, which often comprise 0.2% phytic acid. Advantageously lower phytic acid concentration makes the reaction time shorter and leads to the reaction being first order. Stoichiometric ratios can be more easily and accurately calculated from a known first order reaction. One can adjust the reaction rates by adjusting the IP6 concentration. Thus in the case of higher phytase or protease dose, one may add higher concentration of IP6 so that the reaction rates slow down for the convenience of measuring or observation.

Advantageously, an assay for protease activity or phytase activity may be carried out according to the present invention by contacting the sample suspected of comprising protease activity or phytase activity with the medium comprising the disperse phase, suitably a protein-phytate complex. The sample and the medium can be mixed if the medium is a liquid or some of the sample can be applied to the surface of the medium if the medium is a gel. Clearing of the turbidity of the liquid medium or a clear zone or halo may be seen on a gel medium.

Advantageously no further reagents, other than the medium and the sample are required to assay for protease activity or phytase activity. This avoids the need for toxic reagents or reagents that are damaging to the environment. Because toxic reagents are not needed in the assay of the present invention it can be done under conditions that are close to in vivo physiological conditions. This makes the assay suitable for use in phytase protein engineering, in feed mills and industrial analysis laboratories to estimate the phytase activity before use in feed and food applications. The method of the present invention also provides a one-step assay for protease activity where the sample is mixed with the medium and the result is observed. No further reaction steps are required to assay for phytase or protease activity. For example, there is no requirement to assay phytic acid released from the complex. The assay of the present invention is adaptable for use in a microplate.

Advantageously, because of one or more of the attributes of the assay method of the present invention, for example, short reaction time, small number of reagents and one-step reaction, the present invention is suitable for high throughput screening for protease and/or phytase activity.

In an embodiment where the medium is a gel, for example agarose gel in a petri-dish, phytase or protease will make a clear halo on an opaque agarose plate containing the phytic acid-protein complex. The increase in size of the halo with time and phytase or protease dose can be observed by eye or measured by using a camera assisted image analysis robot. A colour reagent may optionally be added to the plate to make the clear zone easier to see. If a colour reagent is added then the method is an end-point method as the colour reagent will usually stop the phytase or protease reaction.

The method of the present invention is preferably carried out in a pH range between 2.5 and 8.5. In one embodiment the pH range is pH 3 to 3.5. This pH range is advantageous because, in this pH range, the phytase is active while the substrate is most stable and the assay is less affected by high concentrations of interfering substances, such as various salts. In one embodiment the pH of the medium may be adjusted to the optimum pH for activity of the phytase or protease that is being tested.

In another aspect, the present invention is a kit for detecting protease or phytase activity using the method according to any of the previous aspects.

In one embodiment the kit may comprise a continuous phase in the form of a gel and a disperse phase. In this embodiment the kit may further comprise a suitable container, for example a Petri-dish, to hold the gel. The gel may be supplied with wells or holes where samples to be tested can be added. The kit may comprise one or more controls or standards. These may be supplied in liquid form, in dried or preserved form or pre-added to the gel.

In another embodiment the kit may comprise a disperse phase in the form of a liquid, and a continuous phase. The kit may further comprise a number of reaction tubes or a microplate. In another embodiment the kit may comprise a dried or preserved disperse phase for example freeze dried or deposited on the inside of a reaction tube. In this embodiment the kit may also comprise the continuous phase in liquid form or a dried or preserved component, for example a powder that can form the continuous phase when water is added. The continuous phase may be deposited on the inside of a reaction tube. The kit may also comprise one or more controls or standards. The controls or standards may be in liquid, dried or preserved form.

The kits of the present invention may further comprise colour charts or turbidity standards for comparison to the samples.

Preferably the method, use or kit of the present invention is an in vitro method use or kit.

Definitions

Enzymatic activity is defined as the ability of an enzyme to catalyse a reaction. This relates to the amount of active enzyme in a sample. Any enzyme that is in the sample but is inactive is not measured by a measure of enzymatic activity. This has the advantage that only active enzyme is taken onto account and inactive enzyme, for example denatured or mis-folded enzymes and those bound to inhibitors are not included in the measure of enzyme activity. In one embodiment the enzyme activity may be a hydrolysis activity.

The medium is the substrate in which the reaction takes place. The medium may be made up of a mixture of substances and may comprise two substances in different phases, for example a gel and a solid or a liquid and a solid.

In one embodiment the continuous phase may be a liquid, for example, water or a buffer. In another embodiment this may be a gel, for example an agarose gel or a polyacrylamide gel or any gel formed by a polymeric substance.

The disperse phase may be particles of a solid or a gel dispersed in the continuous phase. The particles may be discrete from each other. Each particle of the disperse phase may be made of two or more components held together by an intermolecular interaction. The disperse phase may be a complex comprising two or more components.

An interaction between two or more particles or molecules may be, for example, an electrostatic or hydrophobic interaction. In one embodiment the medium comprises a disperse phase wherein each particle of the disperse phase is made up of at least one protein molecule and at least one molecule of phytate or its degradation products. The phytate may be a myo-inositol phosphate ester, for example, myo-inositol hexakisphosphate (IP6) and its degradation products myo-inositol pentakis-, tetrakis-, tris-, bis-, and monophosphate (IP5, IP4, IP3, IP2 and IP1). The protein and the phytate and its degradation products may be held together by an electrostatic interaction where the protein(s) has positively charged group(s), preferably the medium is at a pH below the isoelectric point (pI) of the protein and the protein is therefore positively charged. The protein can form an electrostatic interaction with the negatively charged phytic acid.

The sample may be any substance suspected of comprising an enzymatic activity, for example a protease activity or a phytase activity. The sample may, for example, be a food, a feed, a feed ingredient, a component of a feed, a component of a food an enzyme preparation, a fermentation broth or a cell culture medium containing the enzyme to be assayed.

The sample may be an extract of any one or more of the above examples which may be extracted in water or another solvent, for example a buffer or an organic solvent. The solvent may be compatible with the continuous phase used in the same assay, for example the solvents should be miscible and not undergo reactions with each other that will adversely affect the assay. In one embodiment the solvent may be the same as is used in the continuous phase of the same assay.

The disperse phase may be affected by hydrolysis of one of the components of the disperse phase. For example, hydrolysis of a protein that forms part of the disperse phase or hydrolysis of a phosphate group from phytate and its degradation products that forms part of the disperse phase. In one embodiment the hydrolysis is of one phosphate group from myo-inositol hexakisphosphate (IP6) to form myo-inositol pentakisphosphate (IP5).

The detectable property of the medium may be an optical property, for example, optical density, turbidity or fluorescence. The optical property may be detected by the eye or by using an optical device such as a spectrophotometer, turbidimeter, spectrophotometer, fluorimeter.

The detectable change may be reduction in the amount of turbidity, a change in light absorbance or a change in a fluorescence or phosphorescence property of the medium.

A negative control may be a portion of the medium where the sample is not added or where a control sample, known not to comprise the enzyme activity, is added, or where the sample containing the enzyme(s) has been deactivated, for example by heating or by adding an inhibitor of the enzyme or a denaturing agent to the medium or the gel. In one embodiment the medium is in the form of a gel in a Petri dish. The sample is added to one section of the gel and no sample or a control sample is added to another section of the gel. The section of the gel where no sample or a control sample is added may be compared to the section of the gel where the sample has been added to assess the difference in turbidity. In a liquid assay liquid medium with sample added may be compared to liquid medium where no sample or a control sample has been added.

A positive control may be a portion of the medium or a sample containing a known amount of enzyme activity. In one embodiment a positive control may be made by inactivating enzymes in a portion of the sample to be tested, for example by heating, and then adding a known amount of enzyme activity. This takes into account components of the sample that may affect the reaction rate, for example the possible presence of inhibitors, the type of feed and the type of feed matrix in the sample. In a Petri dish assay with medium in the form of a gel, the positive control sample may be dropped onto the medium and will form a clear area in the turbid medium. The size of the clear area caused by the control sample may be compared to the size of the clear area caused by the sample to be tested.

With regard to positive controls, phytase standards with known amounts of phytase units may be made in 10% NaCl at a pH from 2.5 to 7.5 preferably at pH 4.5 or pH 5.5 in 0.2M glycine-HCl, acetate buffer, 0.1M Mops-NaOH or in solutions containing sugar alcohol, such as sorbitol. The phytase standards may alternatively be in solid form, such as coated form, adsorbed to various carriers, such as cereal by-products or deposited on the inside of a reaction tube.

A negative control plate may be the same as the sample testing plate except that it additionally has sodium fluoride (5-50 mM) which will be able to inhibit phytase activity completely. This means that no halos (clear areas) will be formed on this plate due to phytase activity. If a halo forms then it is most likely due to interfering substances.

The detectable property of the medium may be compared to standard samples with known phytase activity. Standards may be used to construct a standard curve or calibration curve to which the detectable property of the medium may be compared. The kit of the present invention may include one or more standards or standard curves or calibration curves. The calibration curve may have a lower limit of 300 FTU (Phytase activity units)/kg.

The sensitivity of a phytase assay done on an agarose petri-dish or microplate may be modulated according to the phytase dose, one can adjust the reaction speed or halo size by adjusting the IP6 concentration. From 0.1 mM to 0.2, 0.3 etc. The higher IP6 (phytate) concentration the lower the sensitivity. In one embodiment the preferred phytic acid concentration is 0.1 mM.

The optimal ratio in mg/ml (weight) between proteins (beta-casein, soy proteins) and lysozyme is 10-12, so the ratio between protein and phytate should be from 1000 to 0.01.

In one embodiment, for phytase activity assays, protease inhibitors may be added to the feed extract or the sample to be assayed to prevent protease activity from affecting the results of the assay. In another embodiment proteases act on the disperse phase significantly slower than phytases, the assay may therefore be incubated for a short time to prevent protease activity from affecting the results.

In another embodiment, for protease assays, phytase inhibitors may be added to the feed extract or sample to be assayed. In another embodiment, for protease assays, the disperse phase may be a complex of protein with an inositol sulphate, for example myo-inositolhexasulphate (MIHS). This may prevent phytase activity from affecting the results of the protease assay.

As used herein the term "food" is used in a broad sense and covers food and food products for humans as well as food for animals (i.e. a feed). The term "feed" is used with reference to products that are fed to animals in the rearing of livestock. In a preferred aspect, the food or feed is plant-based, for example cereal based. In one embodiment the feed is a soy/wheat or soy/corn based animal feed.

The food or feed may be in the form of a solution or as a solid depending on the use and/or the mode of application and/or the mode of administration.

As used herein the term "food ingredient or feed ingredient" includes a formulation, which is or can be added to foods or feed and includes formulations which can be used at low levels in a wide variety of products. In one embodiment the food or feed ingredient may comprise or consist of a grain, such as corn or wheat, soya and/or a microorganism. Examples of feed ingredients comprising plant products which contain phytate include cornmeal, soybean meal, rapeseed meal, cottonseed meal, maize, wheat, barley and/or sorghum.

The food ingredient or feed ingredient may be in the form of a solution or as a solid—depending on the use and/or the mode of application and/or the mode of administration.

Substances, for example salts, that may interfere with the interaction between protein and phytate or interfere with the activity of phytase or protease may be removed from the sample extract by various separation techniques, for example, gel filtration, ion exchange or use of a desalting membrane.

Advantages

Some advantages have already been presented. Additional advantages are now described.

The present invention provides a phytase activity assay or protease activity assay that can be done without stopping the enzymatic reaction. The assay can also be done using natural proteins.

Advantageously, assays for enzyme activity with the methods, uses or kits of the present invention can be followed in real time. The method does not rely on assaying the end products of a reaction and therefore kinetic studies can be done.

Advantageously, assays for enzyme activity with the methods, uses or kits of the present invention can be done quantitatively, semi-quantitatively or qualitatively.

Advantageously, assays for enzyme activity with the methods, uses or kits of the present invention can be done quickly. In the present invention the first hydrolysis step may be measured, e.g. hydrolysis of IP6 to IP5. This makes the assay faster because there is no requirement for the reaction to go to completion in order to measure enzyme activity. The assay of the present invention may measure reaction rate rather than the products of a completed reaction. In the present invention an indication of enzyme activity may be obtained from the initial reaction rate. This makes the activity assays of the present invention faster because an indication of the enzyme activity may be obtained from the initial rate of hydrolysis. Prior art methods are slower because the reaction has to go to completion so that the products of the reaction may be measured to provide an indication of the enzyme activity.

Advantageously the present invention provides methods for kinetic analysis of enzyme activity.

Advantageously, assays for enzyme activity with the methods, uses or kits of the present invention can be followed by eye. In particular a qualitative or semi-quantitative assay can be done on agar plates by observing changes in turbidity using the eye. This makes the assay simple to perform.

Advantageously, assays for enzyme activity with the methods, uses or kits of the present invention can be done on naturally occurring polypeptides in vitro.

Advantageously, assays for enzyme activity with the methods, uses or kits of the present invention can be done using non-toxic reagents.

Advantageously, assays for enzyme activity with the methods, uses or kits of the present invention can be done on extracts from feed, food or a fermentation broth, for example feed extracts made with water, without further purification steps.

Advantageously, assays for enzyme activity with the methods, uses or kits of the present invention can be done on biological samples, for example extracts from feed, without the assay background being complicated by chemicals, such as inorganic phosphate, that exist naturally in biological samples.

Advantageously, assays for enzyme activity with the methods, uses or kits of the present invention is highly specific as it measures directly the enzyme catalyzed reaction in stead of quantifying the amount enzyme protein present, which can be in both active and inactive forms, as in the case of antibody-based method, such as immunostrip and ELISA can be done on biological samples, for example extracts from feed, without the assay background being complicated by chemicals, such as inorganic phosphate, that exist naturally in biological samples.

Advantageously, assays for enzyme activity with the methods, uses or kits of the present invention can be done without the use of antibodies.

In particular at acidic pH phytate interacts with dietary proteins leading to the formation of phytate-protein aggregates and precipitates that have decreased accessibility to proteases and may result in inefficient protein digestion. Advantageously, assays for enzyme activity with the methods, uses or kits of the present invention can be used to study the influence of phytic acid on protein digestion by protease. In one embodiment of the present invention the substrate that the protease acts on is a disperse phase comprising a complex of protein with phytic acid.

Advantageously, assays for enzyme activity with the methods, uses or kits of the present invention can be used to specifically assay phytase activity and distinguish it from phosphatase activity.

Advantageously, assays for phytase activity with the methods, uses or kits of the present invention can be done very rapidly because hydrolysis of only one phosphate group, for example hydrolysis of IP6 to IP6 provides a detectable property that correlates with phytase activity. It is not required to remove all of the phosphate groups to provide inositol in order to perform the assay.

Advantageously an indication of the enzyme activity may be obtained by the initial reaction rate therefore, not all of the substrate, for example IP6, needs to be hydrolysed in order to give an indication of enzyme activity.

The present invention will now be described by way of example only.

EXAMPLES

Abbreviations

FTU, phytase activity unit; $IP_6$, phytic acid, sodium phytate; $IP_x$, myo-inositol phosphate esters, where x denotes the number of phosphate ester bonds; $P_i$, inorganic phosphate.

Example Section—Part A

1. Preparation of Solutions
1.1. Phytic acid (myo-inositol hexakisphosphate (IP6)), myo-inositol pentakis-, tetrakis-, tris-, bis- and monophosphate solutions, 10 mM prepared in water.
1.2. Inositol sulphates (myo-inositolhexasulphate (MIHS)) solution, 10 mM prepared in water.
1.3. 0.25M glycine-HCl solution (BG, Buffer G) with pH from 1.5 to 4.0.
1.4. Beta casein solution and soy protein solution, were prepared in BG at a concentration of 2 mg/ml. Lysozyme solution was prepared in 0.1M glycine HCl (pH3.0) at 2.5-43 mg/ml.
1.5. Phyzyme XP®, a variant of *E. coli* phytase.
1.6. Protease P-3000, a variant of subtilisin, a protease from *Bacillus subtilis*.
1.7. Feed enzyme extract: 5 g feed was mixed with 45 ml water and filtered afterwards through filter paper or a glass fibre filter, which is much faster than filter paper. The filtrate obtained was used as enzyme extract (also referred to as "filtrate" in these examples). Alternatively, 12.5 g feed was mixed with 37.5 ml water. After standing still for a couple minutes, the supernatant obtained was directly applied to the wells on petri-dishes without filtering. In general, the feed water ratio can be 1:1 to 1:20. Separation of the supernatant from feed slurries can be achieved by gravity or by centrifugation at 4000 rpm for 20 min.

Protease inhibitor cocktails were from Roche, and contained inhibitors to the 4 major protease classes (serine protease, cysteine protease, metalloprotease, and aspartic acid protease).

All other chemicals were obtained from Sigma Fine Chemicals; all enzymes including phytase Phyzyme XP® and Protease P-3000® are commercial products from Danisco A/S (Brabrand, Denmark).

2. Instruments and Laboratory Wares

Scanning Microplate spectrophotometer SpectraMax M5 was obtained from Molecular Devices Corp. (Sunnyvale, USA). Microplates of different formats were obtained from Nunc A/S and Corning.

3. Assay Systems.
3.1. The Test Tube/Cuvette Method:
To a transparent tube or a cuvette were added:
20 μl 10 mM IP6 (called Test tube) or 15 ul MIHS (called Control tube);
1 ml enzyme solution (e.g., feed enzyme extract filtrate);
1 ml 0.25M glycine-HCl so that the final pH of the mixture was around pH 3.0.
After mixing, the OD at 600 nm was read using a spectrophotometer or a turbidmeter, or observed by the naked eye.

The presence of phytase in the enzyme solution causes the turbidity to decrease in the presence of IP6, but not in the presence of MIHS, which can act as a negative control. The presence of protease will have the same effect as phytase not only in the presence of IP6 but also in the presence of MIHS.

Assays for phytase activity may also be done in the presence of protease inhibitor mixtures (for example protease inhibitor cocktail from Roche), EDTA at 10 mM, Tween 20 at 0.02% (w/v), pectin at 0.01 to 0.5% (w/v) and antimicrobials such as benzoic acid at around 0.05-0.5% (w/v). All of these were not found inhibitory for the formation of IP6 or MIHS soy protein complex and phytase. Protease assays were done in the absence of protease inhibitors specific to the assayed protease.

Test tubes and Control tubes containing IP6, MIHS, soy protein and one or more of the above mentioned additives were alternatively freeze-dried. When it came to use, feed extract filtrate was added directly to these tubes containing the dried material and mixed to dissolve the material. After incubation, the clarity of the Test tubes and Control tubes was observed.

3.2. The Microplate Method:
To a microplate with 96 well format were added:
2 μl of 10 mM IP6 or 1.5 μl of 10 mM MIHS;
0.1 ml enzyme solution (e.g., feed enzyme extract filtrate);
0.1 ml 0.25M glycine-HCl containing soy protein, beta-casein or lysozyme
so that the final pH of the mixture was around pH 3.0.
After mixing, the OD at 600 nm was read spectrophotometrically every 1-5 min for 10 min to 16 hours. The presence of phytase in the enzyme solution caused the absorbance to decrease in the presence of IP6, but not in the presence of MIHS, which acted as a control. The presence of protease had the same effect as phytase not only in the presence of IP6 but also in the presence of MIHS.

3.3. The Petri-Dish Method
A soy protein solution at 2 mg/ml in 0.1M glycine-HCl (pH 3.0) containing agarose at 1.5% (w/v) was made and warmed in a water bath to melt the agarose. To 1 ml of this soy protein-agarose solution was add 10-40 μl 10 mM IP6 or 10 ul MIHS, mixed and poured into petri-dishes so that each 9-centimeter in diameter petri-dish contained about 9 ml having a IP6 concentration of 0.1-0.4 mM. The agarose gel plate having MIHS may function as a negative control for the assay of phytase activity. Alternatively an agarose gel plate with 10 mM NaF, which inhibits phytase can be used as a negative control. Both MIHS and NaF are reversible inhibitors of phytase. If a clear halo develops within short time on negative control plates, it could be caused by interfering substances, such as highly soluble positively charged ions, for example $Ca^{2+}$, that compete with positively charged proteins to bind to negatively charged phytic acid leading to clear halo formation.

After gelling by placing the petri-dish at room temperature (preferably below 30° C.), holes (wells) were made on the gels so that each hole could hold 20 μl liquid. To each of the holes was added 20 μl of feed extract with or without filtration. For negative controls 20 μl extraction buffer or water was added to the hole instead of enzyme solution. For positive controls and quantification purposes a known amount of phytase or protease dissolved in the feed extract was added to the hole instead of feed extract.

The petri-dish agarose plates were incubated at 5-35° C. and the appearance and size of halos were observed with the naked eye, measured for diameter with a ruler or using a digital imaging system. Agar and other gel forming polymers could be used in place of agarose. Petri-dishes can be substituted by any containers that have different dimensions and can even be plate (20×20 cm for example).

Soy protein can also be replaced with another protein as long as the protein forms an intermolecular interaction with the polyvalent component to form a disperse phase which provides a detectable property, such as turbidity to the medium or the gel.

Under conditions where the protein is positively charged, IP6 can be substituted by any other negatively charged polyvalent components like MIHS. In assays for protease detection the IP6 can be replaced with other negatively charged polyvalent components such as poly lysine and oligomers and polymers of chitin and chitosan or any proteins that have negative charge under the assay conditions.

4. Assay of Phytase in Feed Samples by Conventional Methods

This was carried out basically essentially as described by Engelen A J, van der Heeft F C, Randsdorp P H, Smit E L. 5 g of feed were extracted with 50 ml 0.25M acetic acid-Na acetate buffer (pH5.5) containing, 0.0147% (w/v) calcium chloride dihydrate, and 0.01% Tween 20. 0.25 ml of the filtrate after filtering of the extract was mixed with 0.75 ml of the extraction buffer, and then mixed with 2 ml of phytic acid substrate solution (250 ml extraction buffer containing 2.1 g of sodium phytate decahydrate). The mixture was incubated at 37° C. and analyzed for the release of inorganic phosphate by a traditional phosphate assay method using the toxic molybdate-vanadate reagents developed in 1920s and 1940s (for example by Fiske (1925) and Lowry (1946)). One unit of phytase (FTU) is defined as the amount of enzyme needed to release 1 micromole inorganic phosphate from 5.1 mM sodium phytate at 37° C.

5. Making Phytase Standards for Making Standard Curves and to be Used as Positive Controls Phytase standards were made by diluting stock solution of Phyzyme XP® of 7150 FTU/ml to 1 FTU/microliter with water. 0-26 microliters were added to each tube (Table 1) and the tubes were placed in the 50 ml falcon tubes in the fume hood to air dry them.

TABLE 1

| Sample or tube no. | FTU/kg | 13 g feed has FTU | Phyzyme XP ® (1 FTU/microliter) added to the tube |
|---|---|---|---|
| 1 | 0 | 0 | 0 |
| 2 | 100 | 1.3 | 1.3 |
| 3 | 200 | 2.6 | 2.6 |
| 4 | 300 | 3.9 | 3.9 |
| 5 | 400 | 5.2 | 5.2 |
| 6 | 500 | 6.5 | 6.5 |
| 7 | 700 | 9.1 | 9.1 |
| 8 | 1000 | 13 | 13 |
| 9 | 1500 | 19.5 | 19.5 |
| 10 | 2000 | 26 | 26 |

2-20 ul Phyzyme XP® stock solution was added to a 50 ml falcon tube and dried at room temperature as shown in table 1 above so that the tubes contained phytase in the range of 0-26 FTU/kg. 13 g of a different feed material containing no phytase or phytase in an amount less than 50 FTU/kg was added to each tube containing dried Phyzyme XP® at 0-26 FTU. Water was added to make the volume to 50 ml and the feed to and the water were mixed. 0.02 ml samples from each tube were put into wells on a petri-dish which contained agarose gel containing 0.1 mM IP6 and 2 mg/ml soy protein. The Petri-dish assay was developed at 22° C. for 7 h, then the diameter or area halo was measured. A curve was drawn of FTU/kg against diameter of halo or halo area.

Alternatively 50 ml water may be added to the 50 ml tubes containing 1.3-26 FTU and mixed. A 20 microliter sample may be added to the petri-dish containing agarose gel containing 0.1 mM IP6 and 2 mg/ml soy protein. The standard phytase solutions should be able to cause clear halos within 16 h. If a clear halo is not formed within this time the feed material or the water used may contain phytase inhibitor(s).

Results

1. Aggregation of Soy Protein, Bovine β-Casein and Chicken Egg White Lysozyme as a Function of Phytic Acid Concentration In FIG. 1a it can be seen that, with the increase of phytic acid concentration in the presence of soy protein or bovine β-casein, the turbidity measured at OD 600 nm increased linearly at the beginning and then levelled off. The reaction mixture consisted of phytic acid (1 mg/ml) 0, 2, 4, 6, 8, 10, 12, 14, 16, 18 or 20 μl, β-casein or soy protein 100 μl in 0.25M glycine-HCl pH 2.5 (Buffer G), and buffer G to a final volume of 120 μl. The final protein concentration was 1.5 mg/ml. The mixture was mixed and OD at 600 nm was measured immediately.

In FIG. 1b, it can be seen that lysozyme and phytic acid can form a complex with reasonable turbidity as indicated by the absorbance at 600 nm from pH 2.73 to pH 6.95 tested in 40 mM of different buffers of glycine-HCl, acetate, Mes-NaOH at temperatures between 21 and 37° C. This indicates that lysozyme (2.5 mg/ml)-phytic acid (0.3 mM) complex can be used as substrate for the assay of phytase or protease activity in a pH range from at least pH 2.73 to pH 6.95 by following the absorbance decrease at 600 nm as a consequence of the enzymatic reaction.

In FIG. 2 it can be seen that turbidity of phytic acid-soy protein complex and MIHS-soy protein complex increased with the pH. The phytic acid-soy protein system is apparently more sensitive to pH at pH higher than pH 2.5. The final poly-negative ion (phytic acid or MIHS) concentration was 0.2 mM, the soy protein concentration was 1.5 mg/ml.

The turbidity of phytic acid-soy protein complex increased linearly to pH 3.8 and then levelled off (data not shown).

2. The Relationships Between Inositol Phosphorylation Degree and their Capability to Aggregate Proteins It was observed that the hydrolysis of a single phosphate residue from phytic acid dramatically decreased its capability to form a complex with proteins like soy protein (which is a mixture of different proteins) and bovine β-casein. Myo-Inositol with 4 or fewer than 4 phosphate groups has little or no capacity to form aggregates with these two proteins.

2.1. Soy Protein Complexing with Phytic Acid and its Degradation Products

The effects of different inositol phosphate esters and IP5 positional isomers on their aggregation of soy protein were tested. The reaction mixture consisted of 5 μl phosphate ester (30 nmole/10 μl), 15 μl Buffer G and 100 μl soy protein in Buffer G. Final IP1-IP6 concentration was 125 μM, final β-casein concentration was 1.5 mg/ml. Turbidity as a measure of the degree of aggregation was monitored at 600 nm. Final concentration of inositol esters were 125 μM of IP1-IP6 and a final soy protein concentration of 1.45 mg/ml. The results of this study are shown in FIG. 3.

2.2 β-Casein Complexing with Phytic Acid and its Degradation Products

The effects of different inositol phosphate esters and IP5 positional isomers on their aggregation of bovine β-casein were tested. The reaction mixture consisted of 5 μl phosphate esters (30 nmole/10 μl), 15 μl Buffer G and 100 μl β-casein in Buffer G. Final IP1-IP6 concentration was 125 μM, final β-casein concentration was 1.5 mg/ml. Turbidity as a measure of the degree of aggregation was monitored at 600 nm. The results of this study are shown in FIG. 4.

2.3 Addition of Phytase

In FIG. 5 it can be seen that addition of phytase enzyme (Phyzyme XP®) clarified the turbid phytic acid-soy protein complex. The reaction conditions were the same as in 2.1 above except the temperature was set at 37° C. instead of 25° C. The time needed for the solution of IP6-soy protein complex to become completely clarified using different concentrations of added phytase was: 5 min for 1 U/ml, 12 min for 250 mU/ml, 20 min for 125 mU/ml, 40 min for 50 mU/ml, 1.6 h for 12.5 mU/ml, and 2 h for 6.25 mU/ml (1U=1 phytase unit or 1 FTU, 1U=1000 mU).

3. Methods Developed for the Assay of Phytase and Protease Using Phytic Acid-Soy Protein Complex as the Substrate 3.1. The Test Tube/Cuvette Method FIG. 6 shows test tube based phytase or protease activity assay kit (top, right panel), which can be complemented with a shaker (Bottom, left panel) and a turbidimeter with round-shaped cuvettes having a volume varying from 1-25 ml (bottom right panel). The top left panel of FIG. 6 shows tubes containing over-night incubation tests of feed extract filtrate with phytic acid and soy protein. From left the tubes in FIG. 6 contain: Feed extract having 0 (control), 186, 442, 1129, 2301 and 210, 368 FTU/kg.

Procedure for the test tube/cuvette method of phytase activity fast assay

1) Add about 45 ml water (can be tap water, bottled still drinking water) to the 50 ml feed tubes containing 5 g feed so that the final volume is about 50 ml or 90 ml water to 100 ml container containing 10 g feed, 180 ml water to container containing 20 g feed.

2) Shake the tubes/containers so that the feed pellet or mashed feed becomes dissolved (about 5-10 min). Let the tubes stand still for a couple of minutes to allow the supernatant to separate from the feed mass.

3) Pour the supernatant into the funnel so that it can be filtered by filter paper or a glass fibre filter. Collect about 3 ml of filtrate.

4) Transfer 1 ml of filtrate using disposable graduated Pasteur pipette into the tube marked with "Control", which may either contain 1 ml of liquid containing MIHS and soy protein or dried MIHS and soy protein material, shake the tubes to mix the two solutions or dissolve the solid material in the tube.

5) Transfer 1 ml of filtrate using the graduated Pasteur pipette into the tubes marked "Test", which may either contain 1 ml liquid containing IP6 and soy protein or dried IP6 and soy protein material. Shake these tubes.

6). Observation. For corn/soy based feed, the turbidity difference between the Control tube and the Test tube containing feed extract can be seen in about:

5 minutes with phytase dose level over 2000 FTU/kg feed;

30 minutes with phytase dose level of 1000 FTU/kg feed;

5 hours with phytase dose level of 500 FTU/kg; and

Over-night with phytase dose level of around 200 FTU/kg.

The reaction between the feed extract filtrate and IP6 soy protein complex is preferably performed by placing the tubes on a shaker as shown in FIG. 6, bottom left panel.

The time need to see the clarity difference between Test tube and Control tubes may vary with different feed matrices. It is usually faster with corn/soy based feed than wheat based feed.

If there is no difference between the Test tube and the Control tube, one can not completely exclude that the feed has no phytase added as the feed may contain unknown or uncharacterized phytase inhibitors, which may in turn affect the phytase performance in vivo after intake of the feed by the animals. A control can be done in which a known quantity of phytase enzyme is added to the feed extract filtrate. If the feed extract with added phytase enzyme can not cause a decrease in turbidity in the expected time then this may be due to the presence of phytase inhibitors.

Alternatively the pH of the reaction mixture can be checked, which should preferably be pH 2.9-pH 3.1 if soy bean protein and phytic acid complex is used as substrate.

If no difference between the Test and Control tubes can be seen the feed extract may contain intrinsic phytase inhibitor(s). In such a case, the phytase in the feed filtrate may be separated from the inhibitor(s) by gel filtration, ion exchange or affinity chromatography before the assay.

The clarity difference between Test tube and Control tube can be read using a spectrophotometer or a turbidity meter or simply observed by naked eye. The difference between the Test tube and the Control tube can also be seen by the amount of precipitation at the bottom of the tubes after letting them standing still for a certain time. Usually the Test tube should have no or less precipitate compared to Control tube.

3.2. The Microplate System

The microplate system is a miniaturization of the test tube system so that many samples can be analyzed on the same plate simultaneously and can be monitored by using an Elisa reader or microplate reader for quantification of phytase or protease at any wavelength between 200 and 800 nm, preferably between 350 and 700 nm, more preferably between 400 and 600 nm. As turbid solutions can absorb light in the visible wavelength region, it is also possible and may even be preferable for microplate readers with filters instead of monochromators to be used. Furthermore, chromophore probes or fluorescence probes like thioflavin T and DCVJ [9-(dicyanovinyl)-julolidine] may be added to the reaction system which will convert the aggregation of proteins and turbidity changes into fluorescence signals, which can be monitored by a fluorimeter (also called a fluorometer) or a fluorescence spectrophotometer.

3.2.1 Phytic Acid-Soy Protein Complex as Substrate for Phytase

FIG. 7 shows that for corn/soy based feed, the pH of the phytic acid soy protein complex should preferably be between pH 2.5 and pH 4.0 where the turbidity difference is the largest. FIG. 7 shows the results of a test where a solution comprising phytic acid-soy protein complex was mixed with an equal volume of corn/soy feed tap water extract and incubated at 25° C. for 5, 30 and 60 min.

FIG. 8, shows that for the corn/soy based feed having 2301 FTU/kg, it took 4 min for the solution to become clear, for the feed having 1129 FTU/kg it took 15 min, for feed having 442 FTU/kg it took 1.5 h. For feed having 233 or 184 FTU/kg, the solution was still not clear after 5 h incubation. All of these tests were done at room temperature (25° C.).

3.2.2 Comparison of Phytase Activity in Different Feed Samples

In the following tests, each of the microwells contained:
2 µl IP6, 10 mM;
water 20 µl;
100 µl feed extract filtrate;
80 µl soy protein.

In the blank, 2 µl IP6 was omitted or the feed had phytase less than 50 FTU/kg, which is the detection limit by the conventional phytase assay method.

In the negative control (Crtl) 2 µl of 10 mM IP6 was replaced with 2 µl of 10 mM MIHS.

After 2 hours incubation at 25° C. the reading at 600 nm was recorded. The readings are shown in the table in FIG. 9.

Tests were done on randomly selected feed samples from different countries.

The table in FIG. 9 shows the phytase assay using feed samples randomly selected from feed mills from 4 different countries. One can see that after 2 hours at 25° C. the absorbance of the wells in rows A, B, C, E, F and G, corresponding to 6 feed samples from Costa Rica (CR), 3 from Australia (AU), and 4 from France (F) with Phyzyme XP®, have decreased to the value of the blanks, which had an OD at 600 nm of around 0.060.

Control samples corresponding to each feed sample but with no Phyzyme XP® added are shown in row D. Their absorbance was similar to that of negative controls.

After 2 hours incubation at 25° C., 3 samples randomly selected from China (CN), shown in wells A8-D9, A11-D11, showed OD 600 nm that had also decreased but not as significantly as samples from the other countries. It took overnight incubation (ca 16 hours) for the Chinese samples before their OD values decreased to the value of the blank.

The photograph in FIG. 9 was taken after 2 hours incubation of the microplate at 25° C. and represents the results in the table of FIG. 9 visually.

FIG. 10 shows the changes in turbidity over time of phytic acid-soy protein complex in 0.25M glycine solution at different pHs. Feed extract filtrate was added to the complex and the turbidity of the solution was followed over time. The feed samples used were two randomly selected feed samples from Canadian feed mills having 641 FTU/kg and 988 FTU/kg, respectively. The reactions were performed at 25° C.

It can be seen that after 4 hours incubation the turbidity of the feed extract filtrates incubated with soy protein solution in 0.25M glycine having a pH of 3.0 in the presence of IP6 (phytic acid) did not decrease substantially.

In contrast, the turbidity decreased faster for the soy protein solution in 0.25M glycine-HCl with pH 2.5 and even faster at pH 1.9.

These results indicate that the pH of the reaction mixture can be essential for the phytase catalyzed hydrolysis of phytic acid complexed with soy proteins. This is because the feed extract filtrate prepared in water has a certain amount of buffer capacity. The feed extract of different feeds can vary in their buffer capacity. Usually corn/soy based feed has higher buffer capacity than wheat based feed. The closer the final pH of the mixture comprising filtrate, the soy protein solution and IP6, is to pH 3 the faster the reaction.

FIG. 11a and FIG. 11b show the relationship between turbidity change and phytase dose contained in 12 different Canadian feed samples selected randomly from Canadian feed mills. As can be seen, two of the 12 samples, which were found by traditional phytase assay methods to have phytase activity of 276 and 561 FTU/kg, respectively, did not change their solution turbidity after a 2.5 hour incubation.

It is possible that the feed sample measured by traditional phytase assay methods as having 561 FTU/kg contains a strong phytase inhibitor. Alternatively the amount of phytase activity measured may be affected by the feed matrix. The reaction rate is faster when this assay is used with corn/soy based feed than with wheat/soy based feed. This may be due to the type of polysaccharides in the feed matrix. In order to account for differences in reaction rates due to the feed matrix or to the presence of protease inhibitors suitable controls may be used.

3.2.2. Phytic Acid-Soy Protein Complex as Substrate for Protease P-3000®

FIG. 12 shows phytic acid-soy protein complex as substrate for protease P-3000® monitored by absorbance at 600 nm as a function of reaction time and at different pH values. The reaction mixture contained IP6, feed extract containing protease P-3000 and soy protein solution in 0.25M glycine-HCl pH 1.9, 2.5 and 3.0, respectively. The conditions were the same as above except that each well contained 114 units of protease P-3000. One can see that at pH3.0 the turbidity decreased with time while at pH 1.9 and 2.5 no significant changes in turbidity could be seen indicating that P-3000 as an alkaline protease had no activity at too low pH.

4. The Petri-Dish Method:

4.1 Advantages of the Petri-Dish Method

The petri-dish method is an important alternative to the test tube or the cuvette method and the microplate method.

Some advantages of the petri-dish method are:
1) there is not always a need to prepare a negative control containing MIHS as water instead of feed extract can function as a negative control;
2) only small volumes of sample are required, for example, this technique can be to performed with only 0.02 ml of sample;
3) the filtration step may be avoided since feed slurries can be also used as the samples may be directly applied to the sample well in the petri-dish;
4) many samples can be assayed in parallel on a single plate;
5) the diameter or the area of the halo provides an indication of the how many phytase units there are in the sample;
6) comparing the halo-diameters between different samples is more straight forward than comparing the turbidity of different tubes;
7) all of the materials used for the petri-dish method are non-hazardous and disposable.

The degree of turbidity or the diameter of the halos in relation to the amount of phytase present is only proportionally related if the feed matrix or feed composition is the same. If there is the same amount of phytase but the feed matrix is different then the halo size can be different. For example the wheat based feed at 836 FTU/kg has a similar halo size to the corn/soy based feed at 442 FTU/kg (FIG. 14).

The feed matrix is the same as the feed composition. Farmers can always formulate their own feed composition based on the cost of different raw materials, and if they want to add additional additives, all of these may have certain effect (big or small) on the reaction rate of phytase in degrading phytic acid present in the phytic acid-soy protein complex. For example, the feed water extract of wheat based feed is much more viscous than corn/soy based feed. Such high viscosity may contribute to the fact that at the same phytase dose the halo size is smaller if the feed matrix is wheat based compared to corn/soy based feed matrix. Therefore, control samples may be used to quantify the amount of enzyme activity in a particular sample.

Materials used for the petri-dish method (FIG. 13):
1. Petri-dish: The petri-dish may have black gridlines and numbering. The dishes may be stored in closed plastic bags preferably at 8° C. or below but not frozen.
2. Pipette: pipette for sucking 20 ul feed extract. It can be disposable plastic Pasteur pipette.
3. Plastic tubes or containers for feed extraction
4. Standard ruler.
5. A mini-incubator set at 35° C. can be advantageous for incubating the petri-dishes so that the halo can appear faster.

FIG. 14 shows the results of an assay done by the petri-dish method as follows. 9 ml of soy protein solution in 0.25M glycine HCl pH 3.01 was mixed with 0.095 g agarose, heated, to dissolve the agarose, then 0.27 ml or 0.36 ml of 10 mM phytic acid was added so that the final concentration was 0.3 and 0.4 mM, respectively. The solutions were mixed and the mixture was poured into a petri-dish to make a plate. After the plate had cooled holes were made in the gel.

5 g of corn/soy based feed containing phytase 0, 186, 233, 442, 1129 and 2301 FTU/kg or 5 g wheat based feed containing 836 and 1586 FTU/kg, respectively, was added to 45 ml of tap water and shaken for 5-10 min to dissolve. The mixture was left to stand for 1-2 min and then 20 µl of the supernatant was added to each well of the petri-dishes. The lid of the petri-dish was replaced and the dish was allowed to stand at room temperature for several hours until development of a halo (transparent area in the opaque gel) could be seen. The diameter of the halo should be proportional to the amount of phytase present in the extract. For higher phytase doses, for example 1000-2000 FTU, the transparent ring could be seen in 10-20 min.

In FIG. 14 the plate was incubated at 35° C. for 4 h and then 23° C. for 15 h. This made the plate "overreact" as the halos became very large and some of them merged with each other at the higher phytase doses, i.e., 1129 and 2301 FTU/kg.

FIG. 14 also shows that the results do not differ very much when the final phytic acid concentration is 0.3 or 0.4 mM.

In FIG. 14 the wells are marked 0, 186, 233, 442, 1129 and 2301, which denotes the number of phytase units per kg corn/soy based feed. The wells marked 836 and 1586 relate to 836 and 1586 units per kg of wheat based feed, respectively.

The halo size for samples from wheat based feed is generally smaller than those for samples from corn/soy based feed as wheat 836 FTU/kg has a similar halo size with corn/soy at 442 FTU/kg. This might be related to the differences in the feed matrices of these two feeds. Addition of xlyanase and pectinase to the wheat extract did not improve the phytase activity.

FIG. 15 shows the effect of buffer concentration on halo size in the petri-dish assay.

The tests whose results are shown in FIG. 15 were designed to see if the buffer concentration used to make the gel would have any effect on the halo size. The phytic acid concentration was 0.4 mM, agarose was 1.5% (w/v). Soy protein was 2 mg/ml. The results indicate that halo size (related to Phyzyme XP® activity) was similar for all the 4 buffer concentrations. The background of the gel becomes clearer with the increase in buffer concentrations. A low buffer concentration, for example 0.10M glycine-HCl may be used to provide good contrast between the cleared halo areas and the background.

The average halo diameter (cm) and the halo area (cm$^2$) measured for the 4 p-dishes from the photos in the bottom panels of FIG. 15 are apparently proportional to the amount of phytase activity in the feed at 0 (control), 193, 233, 442, 1129, and 2301 FTU/kg (FIG. 15-16).

FIG. 17 shows the effect of phytic acid concentration (0.1-0.4 mM) and feed water dilution factor on the halo size of agarose gel containing 0.1M glycine-HCl pH 3.0 and soy protein 2 mg/ml.

Tests shown in FIG. 14 show that a final IP6 concentration of 0.3 or 0.4 mM gave more or less the same results in 0.25M glycine-HCl buffer. FIG. 17 shows further data for final IP6 concentrations of 0.1 and 0.2 mM in 0.1 M glycine-HCl pH pH3.0, and also the effect of feed dilutions (water volume (ml) to feed (g) ratio).

The feed used were 3 wheat pelleted samples at 386 FTU/kg (well 1-3), 537 FTU/kg (well 1'-3'), 836 FTU/kg (well 1"-3"), in 1:5, 1:4, 1:3 dilutions, respectively, i.e., to 2 g pulverized feed was added 10, 8 and 6 ml tap water, respectively; one corn/soy based feed at 401 FTU/kg in 1:9, 1:6 and 1:3 dilutions at well CW1, CW2 and CW3, i.e., to 10 g feed was 90, 60 and 30 ml tap water, respectively. The 4 petri-dishes (Plate 1-4) were incubated at 35° C.

Contents of the wells in FIG. 17 are described below.

Plate 1 (bottom left, 0.1 mM IP6): counterclockwise: 386 FTU/kg for W1(1:5), W2(1:4) and W3(1:3); 537 FTU/kg for W1' (1:5), W2'(1:4), W3'(1:3); 836 FTU/kg for W1" (1:5), W2" (1:4), W3"(1:3). Middle wells 401 FTU/kg, CW1(1:9), CW(1:6), CW(1:3).

Plate 2 (bottom right, 0.2 mM IP6): counterclockwise: 386 FTU/kg for: W1(1:5), W2(1:4) and W3(1:3); 537 FTU/kg for W1'(1:5), W2'(1:4), W3'(1:3); 836 FTU/kg for W1" (1:5), W2"(1:4), W3"(1:3). Middle wells 401 FTU/kg for CW1(1:9), CW2(1:6), CW3(1:3).

Plate 3 (top right, 0.3 mM IP6): counterclockwise: 386 FTU/kg for W1(1:5), W2(1:4), W3(1:3). 537 FTU/kg for W1'(1:5), W2'(1:4), W3'(1:3). 836 FTU/kg for W1"(1:5), W2"(1:4), W3"(1:3). Middle wells 401 FTU/kg for CW1(1:9), CW(1:6), CW(1:3).

Plate 4 (top left, 0.4 mM IP6): counterclockwise: 386 FTU/kg for W1(1:5), W2(1:4), W3(1:3). 537 FTU/kg for W1'(1:5), W2'(1:4), W3'(1:3). 836 FTU for W1"(1:5), W2" (1:4), W3"(1:3). Middle wells 401 FTU/kg for CW1(1:9), CW2(1:6), CW3(1:3).

Observations (see FIG. 17):
1). Background opaqueness in relation to IP6 concentrations: the agarose gel of Plate 1 with 0.1 mM IP6 has a lighter background while the agarose gels in Plates 2-4 having 0.2-0.4 mM IP6) show very similar background opaqueness.

2). Halo size in relation to IP6 concentration: After 1 hour at 35° C., the halo started to appear. Halo size increased in general the decrease in IP6 concentration from 0.4 to 0.1 mM, especially at lower phytase dose levels. This could be explained by the time take to digest the IP6 at 0.1 mM in the halo area.

3). Halo size in relation to feed dilution factor: In general lower dilution gave larger halo size in all the feed samples tested.

4.3 Protease Assay

The petri-dish method can also be used for protease assays. Soy protein agarose gels were made with both phytic acid (0.4 mM) and with MIHS (0.2 mM) following the method described in 4.2 above. The amount of protease P-3000 added to each gel was: 0 (control), 114, 570, 1140, 2280, 3420 or 4560 units. The incubation conditions were 15 h at 23° C. From the photos in FIG. 18, one can see the halos on the gel containing phytic acid 0.4 mM (left hand photo in FIG. 18) has two white ring structures compared to the gel containing MIHS (shown on the right in FIG. 18), both of which are dramatically different in appearance from the halos formed with phytase, which can therefore be used to distinguish if a halo is produced by the action of phytase or protease. The rings may be formed by insoluble soy protein hydrolysis products.

TABLE 2

The composition of corn/soy based feed used

| Corn soy based feed composition | Percent (%) |
|---|---|
| Corn | 60.01 |
| Soybean meal | 31.52 |
| Soy oil | 4.00 |
| Salt | 0.40 |
| DL Methionine | 0.20 |
| Limestone | 1.16 |
| Dicalcium phoshpate | 1.46 |
| Vitamines and minerals | 1.25 |
| Total | 100.00 |

The composition of corn/soy based feed and wheat/soy based feed are set out respectively in Table 2 above and Table 3 below.

TABLE 3

The composition of wheat/soy based feed used

| Ingredient | % |
|---|---|
| Wheat | 72.33 |
| Soybean Meal | 22.60 |
| Soyabean Oil | 2.21 |
| Dical (20% Ca; 18.5% P) | 1.07 |
| Limestone (36% Ca) | 0.30 |
| Salt | 0.30 |
| Lysine•HCl | 0.33 |
| DL-Methionine | 0.04 |
| L-Threonine | 0.13 |
| V/TM Premix | 0.70 |
| TOTAL | 100 |

Effect of pH and Temperature on the Stability of Phytic Acid-Lysozyme Complex

It is advantageous if the phytic acid-protein substrate is stable enough so that it can be used a substrate for phytase assay. From Table 4 below, one can see that the half life ($t_{1/2}$) of the turbidity reduction of the $IP_6$-lysozyme complex is 75 min at 37° C. and 1.5 hr at 30° C. These stabilities are more than that is needed for the assay of phytase, which is in the range of 10-60 min.

TABLE 4

Stability of the $IP_6$-lysozyme complex at various pH and temperatures

| Temperature | 2.5 ≤ pH < 3.5 | 3.5 ≤ pH < 5.5 | ≥pH 5.5 |
|---|---|---|---|
| 45° C. | 10 min | >50 min | 6-12 min |
| 37° C. | 75 min | 110-170 min | 10-70 min |
| 30° C. | >1.5 h | Stable for 60 min | >90 min |
| Room temperature (20-25° C.) | 16 days | 40-45 days | 12-13 days |
| Refrigeration (5-8° C.) | 84 days | No change in 2 months | >2 months |

The $IP_6$-lysozyme complex (0.3 mM:0.23 mM) was prepared in a total volume of 120 µl in 50 mM glycine-HCl (pH 2.5-3.5), 50 mM sodium acetate (pH 3.5-5.5) and 50 mM Tris-maleate (pH 5.5-8.5) containing 0.3 mM $IP_6$ and 0.23 mM lysozyme. The $IP_6$-lysozyme complexes at different pH values were incubated at different temperatures and their turbidity was followed. Data were reported as half life ($t_{1/2}$) of the turbidity reduction of the $IP_6$-lysozyme complex.

Effect of Phytase Concentration on the Phytase-Catalyzed Reaction Using $Ip_6$-Lysozyme Complex as Substrate From FIG. 22, one can see that using lysozyme-phytic acid (IP6) as substrate at pH3.5 and 30° C., the reaction rate is linear in the phytase dose of 0.05 to 0.85 FTU/ml reaction mixture for *E. coli* phytase and 0.05 to 1.3 FTU/ml *A. niger* phytase.

The reaction mixture contained lysozyme 12 µl (0.23 mM), 12 µl $IP_6$ (3 mM), 60 µl glycine-HCl (50 mM, pH 3.5), water and *E. coli* phytase variant 1 (Phyzyme XP®)(a) or *A. niger* phytase (b). The reaction mixture was pre-incubated at 30° C. and mixed quickly for 2 min at 1400 rpm on an ependorf thermomixer. The reaction was started by the addition of phytase at various amounts. Turbidity change was recorded every 30 seconds during the time course of reaction. Reaction rate was expressed as milli OD (mOD) decrease at 600 nm per min.

Use of Phytic Acid-Lysozyme as Substrate for Evaluating the Commercial Phytases

It is known that phytic acid is complexed with mineral salts (which is called phytin) and proteins in plant material as globoids. It is important commercially that a phytase can efficiently hydrolyze phytic acid in the presence of proteins. Table 5 shows that Phyzyme XP is the most efficient enzyme among the 4 phytases tested. Under the assay conditions the turbidity can be converted to µmole Pi release per unit time (e.g., per min). The ratio is 1:3, i.e., the OD600 nm decreases by a factor of 3 equates 1 µmole Pi released.

TABLE 5

Activity of different commercial phytases on $IP_6$-lysozyme and $IP_6$-soy protein complex as compared to $IP_6$ as substrate.

| | Relative activity (%) | | |
|---|---|---|---|
| Phytases | $IP_6$-soy protein | $IP_6$-lysozyme | $IP_6$-Na |
| *Escherichia coli* phytase Phyzyme XP | 164.3 | 229.0 | 100.0 |

TABLE 5-continued

Activity of different commercial phytases on $IP_6$-lysozyme and $IP_6$-soy protein complex as compared to $IP_6$ as substrate.

| Phytases | Relative activity (%) | | |
|---|---|---|---|
| | $IP_6$-soy protein | $IP_6$-lysozyme | $IP_6$-Na |
| *Escherichia coli* phytase Optiphos | 137.8 | 151.8 | 102.7 |
| *Aspergillus niger* phytase Natuphos | 31.8 | 23.1 | 37.0 |
| *Peniophora lycii* phytase Ronozyme P-(CT) | 24.5 | 13.0 | 9.8 |

The assay was carried out in a total volume of 120 μl in 50 mM glycine-HCl pH 3.0 at 37° C. for the 5 different phytases added at a dose of 0.1 FTU/ml. The reaction rates in terms of $P_i$ release (μmol $P_i$/ml/min) was measured by stopping the reaction at different time intervals and analyzing $P_i$ on Konelab. Activity of *E. coli* phytase variant 1 (0.096 μmol $P_i$/ml/min) on $IP_6$-Na was set as 100%. Activities of the phytases on the other substrates are reported relative to the activity of *E. coli* phytase variant 1 on $IP_6$-Na.

TABLE 6

Use of the current method for studying the pH profile of the beta-propeller alkaline phytase from *Bacillus* sp in the presence or absence of 0.1 mM $CaCl_2$.

| | Glycine-HCl buffer | | Acetate buffer | | | Tris-maleate buffer | | | |
|---|---|---|---|---|---|---|---|---|---|
| pH | 2.5 | 3.5 | 3.5 | 4.5 | 5.5 | 5.5 | 6.5 | 7.5 | 8.5 |
| Without CaCl2 | 7.33 | 3.99 | 4.40 | 3.46 | 4.11 | 8.01 | 6.62 | 50.97 | 15.10 |
| mOD/min | 0.43 | 0.16 | 0.05 | 0.02 | 0.07 | 0.39 | 0.070 | 4.57 | 1.17 |
| with 1 mM CaCl2 | 7.69 | 5.71 | 6.47 | 20.66 | 86.40 | 100.10 | 10.50 | 3.25 | 2.47 |
| mOD/min | 0.74 | 0.11 | 0.17 | 0.77 | 6.16 | 7.55 | 1.249 | 0.09 | 0.06 |

Reactions were carried out in 50 mM glycine-HCl (pH 2.5-3.5), 50 mM sodium acetate (pH 3.5-5.5) and 50 mM Tris-maleate (pH 5.5-8.5), respectively, containing 0.3 mM $IP_6$ and 0.23 mM lysozyme in a total volume of 120 μl at 37° C. The enzyme dose was 0.1 FTU/ml based on $P_i$ released from $IP_6$ in conventional phytase activity assay.

Example Section—Part B

A Simple and Fast Kinetic Assay for Phytases Using Phytic Acid-Protein Complex as Substrate
Materials and Methods
Enzymes and Chemicals The bacterial phytases (EC 3.1.3.26) used in this study included: *E. coli* phytase at 10 000 FTU/g (Phyzyme XP, Danisco, Brabrand, Denmark), which is here referred as *E. coli* phytase variant 1, *E. coli* phytase at 2000 FTU/g (Optiphos, JBS United, Indiana, USA), which is here referred to as *E. coli* phytase variant 2, and *Bacillus* sp. MD2 phytase at 163.5 FTU/ml, which was cloned and expressed in our laboratory [33]. The fungal phytases used in this study included: *Aspergillus niger* phytase (EC 3.1.3.8) at 5000 FTU/g (Natuphos, BASF Animal Nutrition, Germany) and *Peniophora lycii* phytase (EC 3.1.3.26) at 10 000 FTU/g (Ronozyme P-(CT), DSM Nutritional Products Europe Ltd, Switzerland). Sodium phytate ($IP_6$) and chicken egg white lysozyme (EC 3.2.1.17) were purchased from Sigma-Aldrich and other chemicals of analytical grade were obtained from Merck.

Phytase Extraction and Activity Determination

All the four commercial phytases were obtained in granulated form and were extracted as described below except the *Peniophora* phytase, which was first ground in a mortar-pestle to improve the extraction. The granulated enzymes or the ground powder of *Peniophora* phytase (200-500 mg) were dispersed in 50 ml of MilliQ water in 100 ml beakers and stirred using a magnetic stirrer at room temperature (22° C.) for 30 min. The suspensions were then left standing overnight (16-18 h) at 5° C. to allow the particles to settle down. The supernatant was then withdrawn gently using Pasteur pipettes, and diluted with MilliQ water to a final enzyme concentration of 20 FTU/ml based on the FTU values provided by the manufacturers. The standard phytase solutions were stored as stock enzyme solutions at −20° C. for subsequent experiments. Phytase from animal feed (12.5 g) was extracted with MilliQ water (37.5 ml), supernatant was obtained by centrifugation and assayed for phytase activity by using $IP_6$ and $IP_6$-lysozyme complex as substrate, respectively.

The activity of the different commercial bacterial and fungal phytases was determined based on the amount of $P_i$ released from $IP_6$ in 0.25 M acetate buffer pH 5.5 at 37° C. [24, 25]. The activity of *Bacillus* sp. MD2 phytase was assayed in 0.1 M Tris-HCl (pH 7.0). The enzyme stock solutions were diluted to approximately 0.03 FTU/ml in 0.25 M acetate buffer (pH 5.5) for histidine acid phytases or in 0.1 M Tris-HCl buffer (pH 7.0) containing 1 mM $CaCl_2$ and 0.01% (v/v) Tween 20 for *Bacillus* sp. MD2 phytase. Two milliliters of 7.5 mM $IP_6$ in 0.25 M acetate buffer (pH 5.5) was added to 1 ml of the enzyme solution pre-incubated at 37° C. for 5 min. The reaction was performed for 60 min followed by the addition of 2 ml of freshly prepared stop reagent containing 1.5:1.5:1 mixture of 10% ammonium heptamolybdate, 0.24% ammonium vanadate and 65% nitric acid. Subsequently, the reaction mixtures were centrifuged at 8000 g at room temperature for 10 min before the absorbance of the supernatant at 415 nm was recorded. A $P_i$ calibration curve was made by treating standard $P_i$ solutions of 0-4.0 mM $KH_2PO_4$ without added phytase under the same conditions as described above. All samples were assayed in triplicates. The phytase activity was calculated from the calibration curve of absorbance ($OD_{415}$) versus $P_i$ concentration (mM). One unit of phytase activity (FTU) was defined as the amount of phytase that releases 1 μmole of $P_i$ per minute under the assay conditions. The activity values obtained for the five phytases were used to design all subsequent enzymatic reactions.

Preparation of Phytate Substrate Complex

Phytate-protein substrate complexes were prepared in 96-well flat-bottomed plates in a total volume of 120 μl. Sixty microliter of a specific buffer, 12 μl of 25 mg/ml lysozyme, 12 μl of 3 mM $IP_6$ and 36 μl of MilliQ water were added to each well, and mixed at 1400 rpm on an Eppendorf thermomixer (model: Comfort MTP) for 2 min at room temperature to form a homogeneous $IP_6$-lysozyme complex.

Other substrate complexes ($IP_6$-soy protein, $IP_6$-lysine and $IP_6$-Ca complex, respectively) were prepared in the same way as $IP_6$-lysozyme by varying the final concentration of $IP_6$ and the corresponding ligands (soy protein, lysine or calcium) to get the desired turbidity.

Kinetic Measurement of the Turbidity Reduction of the Substrate Complex Catalyzed by Phytases The substrate complexes prepared as described above were pre-heated at 37° C. with vigorous shaking (1400 rpm) for 2 min prior to the addition of 1-12 µl phytase to reach the desired final enzyme concentration in FTU. The reaction was carried out at 37° C. for 20-60 min using a microplate reader (PowerWave$_x$, BioTek Instruments, Vermont, USA). The reaction was monitored at 600 nm and data were collected every 30 seconds. Before each reading the microplate was shaken at full scale for 5 seconds. Reactions with MilliQ water instead of phytase samples were used as controls for each enzymatic reaction. All samples were assayed in triplicates. Activity of each phytase sample was calculated as the rate of turbidity reduction of the substrate complex in milli optical density at 600 nm ($mOD_{600}$) per minute.

Inorganic Phosphate Analysis by Konelab

In order to measure Pi released from the substrate complex in the reactions described above, the reactions were stopped at different time intervals by the addition of 30 µl of 2.5 N HCl. Microplates having the reactants were centrifuged at 8000 g for 10 min, and 100 µl of the clear supernatants were transferred manually to 0.5 ml sample cups for Pi analysis by Konelab™ Analyser (Thermo Scientific, Ulm, Germany) according to the instructions from the manufacturer. All samples were measured in triplicates.

HPLC Analysis of Inositol Phosphate Esters

The substrate $IP_6$ and its degradation products ($IP_{1-5}$) from the phytase catalyzed reactions were analyzed on a Dionex DX-500 ion chromatograph system (Sunnyvale, Calif., USA) with a Dionex CarboPac PA-100 column (4×250 mm) and a Dionex knitted coil (75 µl) for post column reaction. The reactions were stopped by the addition of 30 µl of 2.5 N HCl at a specific time and the solutions were filtered through 96-well filter membranes (Pall life sciences, Deland, Fla., USA) with 0.45 µm pore size before being injected into the HPLC column with an injection volume of 100 µl. Separation was performed by a linear gradient of 1-92% 1 N HCl at a flow rate of 1 ml/min. The eluant was mixed in the post column mixing chamber with 0.1% $Fe(NO_3)_3 \cdot 9H_2O$ in 2% $HClO_4$ [23] for detection of the inositol phosphate esters. Samples were analyzed in triplicates.

Results and Discussion

Effect of Phytic Acid and Lysozyme Concentration on Turbidity of Phytic Acid-Lysozyme Complex Most proteins of plant origin, such as those derived from soybean, peanut, cottonseed and rapeseed, have their isoelectric points (pI) in the acidic range (around pH 4). Hence the solution of the $IP_6$ complex with these proteins develops turbidity when the pH is lower than their pI [34, 35]. For example, the solution of $IP_6$-soy protein complex is turbid only when the pH of the solution is decreased below pH 4. On the other hand, chicken egg white lysozyme has a pI of around 11 [36] and is considerably stable in the acidic pH range. $IP_6$-lysozyme complex was found to show turbidity and stability in a wide pH range from pH 2.5 to pH 8.5.

FIG. 23 shows that the turbidity of the $IP_6$-lysozyme complex increases with increase in the concentrations of $IP_6$ and lysozyme at pH 4.0. At around 0.5 mM $IP_6$ and 0.35 mM of lysozyme, the turbidity levels off. Highest turbidity of the solution is seen at an $IP_6$: lysozyme molar ratio>1.5:1. The ratio of 0.3 mM $IP_6$:0.23 mM lysozyme (approximately 2.5 mg lysozyme per ml) was subsequently chosen to prepare an $IP_6$-lysozyme complex for use as substrate for various phytase assays since it showed high turbidity ($OD_{600}$>1) and the reduction in turbidity of the complex was linearly related to the hydrolysis of the $IP_6$ in the complex. Changes in pH, temperature, and salt concentration were subsequently examined for their impact on the turbidity and stability of $IP_6$-lysozyme complex as shown below.

Factors Affecting Turbidity and Stability of Phytic Acid-Lysozyme Complex

Table 7 shows the half life of the $IP_6$-lysozyme complex based on its turbidity at different temperatures and pH. Between pH 2.5 and 5.5, the complex was stable for more than 10 days at room temperature (22-25° C.) and for two months at 5-8° C. without any significant reduction in turbidity. However, at higher temperatures (>30° C.), the stability of the complex was dramatically reduced, particularly at pH 5.5 and above due to the instability of lysozyme under these conditions. It was observed that denatured proteins including lysozyme did not form stable complexes with $IP_6$ partly because the proteins themselves precipitate upon denaturation.

The pH dependence of the turbidity of $IP_6$-lysozyme complex is further shown in FIG. 24. As expected, the turbidity was high ($OD_{600}$ of 1-1.2) in the acidic region (pH 3.5-5.5), and started to decrease around neutral pH and became constant at the lowest level between pH 7.0-8.5, corresponding to about 30% of the highest turbidity value.

TABLE 7

Stability of the $IP_6$-lysozyme complex at various pH and temperatures.

| Temperature | 2.5 ≤ pH < 3.5 | 3.5 ≤ pH < 5.5 | ≥pH 5.5 |
|---|---|---|---|
| 45° C. | 10 min | >50 min | 6-12 min |
| 37° C. | 75 min | 110-170 min | 10-70 min |
| 30° C. | >1.5 h | Stable for 60 min | >90 min |
| Room temperature (20-25° C.) | 16 days | 40-45 days | 12-13 days |
| Refrigeration (5-8° C.) | 84 days | No change in 2 months | >2 months |

The $IP_6$-lysozyme complex (0.3 mM:0.23 mM) was prepared in a total volume of 120 µl in 50 mM glycine-HCl (pH 2.5-3.5), 50 mM sodium acetate (pH 3.5-5.5) and 50 mM Tris-maleate (pH 5.5-8.5) containing 0.3 mM $IP_6$ and 0.23 mM lysozyme. The $IP_6$-lysozyme complexes at different pH values were incubated at different temperatures and their turbidity was followed. Data were reported as half life ($t_{1/2}$) of the turbidity reduction of the $IP_6$-lysozyme complex.

From FIG. 24 one can further see the effect of some common salts, NaCl and $CaCl_2$, which may be present in assay buffers and bio-material extracts, on the turbidity of the $IP_6$-lysozyme complex. It can be seen that the turbidity of $IP_6$-lysozyme complex was quite stable at NaCl concentrations below 15 mM in the acidic region (pH 3-5.5) (FIG. 24a). Increase in NaCl concentration at 30 and 45 mM resulted in significant decrease in turbidity except at pH 3.5. The solution of $IP_6$-lysozyme complex became clear in the presence of 100 mM of NaCl at all pH values in the range of 3.5-8.5.

Investigation of the effect of increasing concentrations of calcium salt at varying pH showed that the turbidity of $IP_6$-lysozyme complex was stable at pH 3-4 at <3 mM $CaCl_2$, but it decreased dramatically at higher $CaCl_2$ concentration, especially at pH>4.5 (FIG. 24b). It is well known that divalent and trivalent metal ions such as $Zn^{2+}$, $Ca^{2+}$, $Fe^{3+}$ have strong interactions with $IP_6$ [10]. FIG. 25 shows that EDTA (in the form of sodium salt), the commonly used chelator in buffers, was not able to restore the high turbidity in the presence of $Ca^{2+}$ and at concentrations higher than 10 mM, EDTA itself also contributed to reducing the turbidity of the solution. Due to the higher affinity to calcium or iron, $IP_6$ has been used as an alternative chelating agent in therapy for calcium urolithiasis [37] and for inhibiting *Vibrio vulnificus* on septicemia-induced mice [38, 39].

Inorganic phosphate is the main product of the phytase-catalyzed reaction, and it can potentially compete with phytate to bind to the positive charged lysozyme. In the standard kinetic assay of phytase having phytate at a concentration of 0.3 mM, the final Pi can be 1.5 mM when all phytate molecules are converted to Pi and myo-inositol monophosphate. It was found that at pH 3.5 in 50 mM glycine-HCl the turbidity of $IP_6$-lysozyme complex was not affected at a $P_i$ concentration up to 50 mM and the turbidity disappeared at 80 mM $P_i$ (FIG. 26). At pH 3.5 to 8.5, $P_i$ up to 5 mM did not interfere with the turbidity of $IP_6$-lysozyme complex (data not shown).

The above results suggest that in spite of the variation in the turbidity with varying testing conditions, the $IP_6$-lysozyme complex can be an ideal substrate for determining phytase activity by following the decrease in turbidity provided that negative controls (without phytase or with denatured phytase) for each enzymatic reaction are run simultaneously. Under the assay conditions neither the bacterial nor the fungal phytases themselves in the range of 0.1 to 2.8 FTU/ml reaction mixture caused detectable turbidity with $IP_6$.

A Comparison of 5 Microbial Phytases for their Activity Toward $IP_6$ and Various $IP_6$ Ligand Complexes Table 8 shows that all the five phytases of bacterial or fungal origin were able to hydrolyze the $IP_6$ in the $IP_6$-protein complexes as indicated by $P_i$ release determined by Konelab analysis. It is noted that the *E. coli* phytases (*E. coli* phytase variant 1 and 2) hydrolyzed $IP_6$ as well as $IP_6$-lysozyme and $IP_6$-soy protein several fold faster than the two fungal phytases (Table 8), which is in line with literature data showing that *E. coli* phytase has higher activity at pH 3 than its fungal counterparts [40]. The activity of a phytase at pH around 3 is an important criterion for its efficiency as a feed enzyme for animal nutrition. Phytases from *Peniophora lycii* and *Bacillus* sp. MD2 showed the least hydrolysis of the three substrates under these assay conditions. In contrast to the *A. niger* phytase, all the four phytases showed 1.3 to 2.3 fold higher activity toward $IP_6$-lysozyme and $IP_6$-soy protein than $IP_6$ based on the Pi released. The difference in the substrate preference of these five phytases could not be related to the ester bonds that are first hydrolyzed since phytases from *E. coli* and *Peniophora lycii* initiate their hydrolysis reaction by attacking the ester bond at the $6^{th}$ position in the phytate molecule [41, 42], while *A. niger* phytase hydrolyzes initially at position 3 [43]. *Bacillus* phytase is a hybrid 3/6-phytase, which initially attacks the phosphate groups at $3^{rd}$ and/or $6^{th}$ position [43] or any position of phosphate [44] in phytate molecules. The observations with the *E. coli* phytase shown in Table 8 were further supported by analysis of the reaction products by HPLC which separated $IP_6$ and its degradation products $IP_5$, $IP_4$, $IP_3$, and $IP_2$ [22]. It was confirmed that the *E. coli* phytases showed higher activity in degrading $IP_6$ in the $IP_6$-lysozyme complex than $IP_6$ in the form of sodium phytate (data not shown). The exact reason why $IP_6$-protein may be a much better substrate for the *E. coli* phytases remains an enigma and needs to be examined by $^{31}$P-NMR. On the other hand, as $IP_6$ can be bound with seed proteins in plant seeds and with food and feed proteins in the upper parts of the digestive tracts of monogastric animals having an acidic environment, the efficient hydrolysis of $IP_6$ in the $IP_6$-protein complex under conditions close to in vivo is a prerequisite for a good feed phytase.

TABLE 8

Activity of different commercial phytases on $IP_6$-lysozyme and $IP_6$-soy protein complex as compared to $IP_6$ as substrate.

| Phytases | Relative activity (%) | | |
| --- | --- | --- | --- |
| | $IP_6$-soy protein | $IP_6$-lysozyme | $IP_6$-Na |
| *Escherichia coli* phytase Phyzyme XP | 164.3 | 229.0 | 100.0 |
| *Escherichia coli* phytase Optiphos | 137.8 | 151.8 | 102.7 |
| *Aspergillus niger* phytase Natuphos | 31.8 | 23.1 | 37.0 |
| *Peniophora lycii* phytase Ronozyme P-(CT) | 24.5 | 13.0 | 9.8 |

The assay was carried out in a total volume of 120 μl in 50 mM glycine-HCl pH 3.0 at 37° C. for the 5 different phytases added at a dose of 0.1 FTU/ml. The reaction rates in terms of $P_i$ release (μmol $P_i$/ml/min) was measured by stopping the reaction at different time intervals and analyzing $P_i$ on Konelab. Activity of *E. coli* phytase variant 1 (0.096 μmol $P_i$/ml/min) on $IP_6$-Na was set as 100%. Activities of the phytases on the other substrates are reported relative to the activity of *E. coli* phytase variant 1 on $IP_6$-Na.

The *E. coli* phytase variant 1 and *A. niger* phytase as representatives of bacterial and fungal, 6-, and 3-phytases, respectively, were chosen to further examine their activity toward $IP_6$-lysine complex. Lysine as a positively charged amino acid and a food and feed additive was chosen as it can potentially complex with $IP_6$ in vivo in the digestive tract. $IP_6$-lysine complex, unlike $IP_6$-lysozyme complex, was not turbid at all pH values between 3.5 and 8.5. Hence, its role as a substrate complex with $IP_6$ for phytase had to be evaluated by the release of Pi. FIG. 27a shows that while hydrolysis of $IP_6$-lysozyme complex by *E. coli* phytase variant 1 was faster compared to $IP_6$, in line with the results shown in Table 8, hydrolysis of $IP_6$-lysine complex was slower. In contrast, *A. niger* phytase did not show much difference in its initial reaction rates with the two substrates $IP_6$-lysine complex and $IP_6$ (FIG. 27b). It should be noted in FIG. 27a and FIG. 27b that the *A. niger* phytase was dosed 5 times higher than the *E. coli* phytase considering its lower activity at pH 3.5.

Beside $IP_6$-protein complexes, $IP_6$-$Ca^{2+}$ complex can also develop turbidity and can therefore be used for the assay of phytases by following the decrease in turbidity. However, the turbidity of $IP_6$-$Ca^{2+}$ complex was low ($OD_{600}$<0.2), especially at pH values lower than pH 5.5. $IP_6$-$Ca^{2+}$ complex could, however, be used as an alternative substrate to $IP_6$-lysozyme for the assay of neutral and alkaline phytases. The Relationships Between Turbidity Decrease and Phosphate Release If the phytase activity assay based on the turbidity reduction of IP$_6$-lysozyme complex catalyzed by 3- and 6-phytases can reflect the hydrolysis of IP$_6$, it is essential that it is validated by the well established method measuring Pi release. FIG. 28 shows that turbidity reduction (OD$_{600}$) of IP$_6$-lysozyme in the kinetic assay developed here correlated well to P$_i$ released from the same enzymatic reaction using both E. coli (FIG. 28a and FIG. 28b) and A. niger phytases (FIG. 28d and FIG. 28e). Phytase activity in these assays could thus be measured as mOD/min, which is equal to the slope of turbidity reduction in the linear range (OD$_{600}$=0.1-0.9). The reaction rate in mOD/min could be converted to the common unit of phytase activity (FTU/ml) by correlating it to the P$_i$ released (FIG. 28c and FIG. 28f). In FIG. 28c and FIG. 28f, it is estimated that every 1 µmole Pi released per min based on the results from Konelab analysis is related to a 3.03±0.27 unit OD decrease at 600 nm per min.

Effect of Substrate and Phytase Concentration

The optimal substrate concentration was found to be 0.3 mM IP$_6$ and 0.23 mM of lysozyme, which was used in all assays in this study. With lower substrate concentration, the turbidity was low which made the linear range of the reaction shorter while with high substrate concentration, the turbidity decrease was not linear with the substrate concentration. It should be noted that the kinetic assay of phytase developed here is based on the monitoring of substrate hydrolysis instead of product formation as in most enzyme assays. This is also one of the reasons one can not use high substrate concentration. Due to these this kinetic method was found not useful for the estimation of K$_m$ and V$_{max}$ of phytases just like the conventional colorimetric assay of phytases. The suitable method of estimation of K$_m$ and V$_{max}$ is by HPLC [22-23].

At an assay of pH 3 to 3.5, assay temperature of 30° C. and a reaction time of 20 to 60 min, the suitable phytase concentration for E. coli and A. niger phytases was in the range of 0.1 to 0.8 FTU/ml reaction mixture. The phytase activity of some cereals, such as rye, triticale, wheat and barley, is in the range of 500 to 5000 FTU/kg [45], while microbes of Aspergilli, E. coli and Bacillus sp. are reported to have a phytase activity of 0.1 to 1.8 FTU/ml broth [33, 41, 46]. In the current study, feed samples containing corn and soy flour and E. coli phytase variant 1 at 400 to 2300 FTU/kg could be assayed by the kinetic method, whereas with phytase level at 200 FTU/kg or lower in the feed the kinetic method was not suitable as the incubation had be overnight long.

The pH Profiles of Five Microbial Phytases Using Phytic Acid-Lysozyme Complex as Substrate In order to evaluate the usefulness of the kinetic method developed, it is also important to test this method in a wide pH range that is relevant for phytases. FIG. 29 shows the activities of the five different microbial phytases as a function of pH in the range of pH 2-8.5 using IP$_6$-lysozyme complex as the substrate. In general the pH profiles obtained by the kinetic method (FIG. 29a-29e) agree well with those reported in the literature using IP$_6$ as substrate [31, 32, 37, 41, 42, 40, 47]. From FIG. 29a and FIG. 29b, one can see that the two E. coli phytases showed similar pH profiles with IP$_6$-lysozyme complex as with IP$_6$ alone [41, 47] except for an extended pH optimum to the acidic region (pH 2-5.5). This could mean that IP$_6$-lysozyme complex as a substrate makes the phytase more stable and therefore active in the acidic region. In FIG. 29a and FIG. 29b, it can be noted that even at the same pH the activity measured varied greatly due to the different buffers used that have different ionic strengths which in turn affect the turbidity of the system.

Using IP$_6$-lysozyme complex as substrate, it was observed that Bacillus sp. MD2 phytase, a calcium dependent enzyme [31, 32], showed a shift of 2 pH units in its pH optimum toward the acidic region in the presence of 1 mM CaCl$_2$ (FIG. 29c). Aspergillus niger phytase showed two optimal peaks of activity at pH 5.5 and pH 2 (FIG. 29d) as with IP$_6$ except that the second pH optimal peak shifted 0.5 unit toward the acidic region (pH 2 instead of pH 2.5) compared to IP$_6$ alone as substrate [37]. The pH profile of Peniophora phytase showed one optimum around pH 4-5, which is in accordance with that reported earlier for the enzyme with IP$_6$ [42]. The broadening of pH optimum in the case of E. coli phytases and the A. niger phytase, and also the shift of pH optimum in the case of Bacillus phytase are obviously advantageous considering the pH of the digestive tract in monogastric animals which is generally in the range of pH 2.5-6.0.

Conclusions

IP$_6$ and lysozyme complex at a concentration of 0.3 and 0.23 mM, respectively, forms a turbid solution and can be used for the kinetic assay of the activity of phytases by monitoring the decrease in absorbance. The decease in turbidity correlates well with the release of Pi. The method is useful for assaying histidine acid phytases, represented by all commercial phytases, and β-propeller phytase tested in this study. Other IP$_6$-ligand complexes including IP$_6$-soy protein, IP$_6$-lysine and IP$_6$-Ca$^{2+}$ were also investigated as substrates, but they were less suitable than the IP$_6$-lysozyme complex. Compared to the conventional end-point colorimetric method based on P$_i$ measurement, the kinetic assay described here is simple, fast, safe, adaptable to high through-put screening, and also more close to the in vivo physiological conditions, making it more suitable for use in phytase protein engineering, in feed mills and industrial analysis laboratories to estimate the phytase activity before use in feed and food applications.

The usefulness of this method has been further demonstrated in studying the pH profiles of five different phytases. The main limitation of this method is that the enzymatic reaction needs to be mixed well before measurements to avoid precipitation of the IP$_6$-lysozyme complex, which can lead to greater deviation in measurement. The linear range for turbidity at OD$_{600}$ (0.1-0.9) is quite narrow compared to the linear range for the colorimetric assay of P$_i$ release. As this kinetic method is based on the monitoring of substrate consumption instead of product formation as in most enzyme assay, it is not suitable for the estimation of K$_m$ and V$_{max}$ of phytases.

Summary

Histidine acid phytases constitute an important group of enzymes for feed and grain processing industries due to their high specific activity and wide pH optima for activity [1]. Phytase catalyzes the sequential hydrolysis of phytate (myo-inositol 1, 2, 3, 4, 5, 6-hexakisphosphate; IP$_6$), a principal storage form of phosphorous in cereals and legumes, to less phosphorylated myo-inositol derivatives with concomitant release of inorganic phosphate (P$_i$) [1]. Hydrolysis of phytate overcomes a number of its negative effects on human and animal nutrition [2-7] and on the environment [8, 9]. It is well established that phytic acid binds positively charged metal ions [10] and bio-molecules [11] making them unavailable as nutrients. In grain processing it is important to add phytase in order to make Ca$^{2+}$ available for α-amylase [12]. Interaction with positively charged dietary proteins leads to the formation of phytate-protein aggregates and precipitates, which decreases their accessibility to proteases, thus resulting in inefficient protein digestion [13-18].

The decrease in protein solubility results from masking of positive charges on the protein molecules by phytic acid, which changes the isoelectric points of the proteins [16, 11].

In vitro studies with phytase reported in literature have been performed with $IP_6$ as the substrate and either the degradation of $IP_6$ or the amount of Pi released has been followed. This method for assaying phytase may not provide a true picture of the enzyme activity since the phytic acid in vivo may not exist in its free acid or sodium salt form. Furthermore, quantitative determination of the $IP_6$ degradation is tedious and time consuming [19-21]. It requires the use of chromatographic techniques with multiple devices as neither $IP_6$. $IP_{1-5}$ nor Pi can be detected directly by absorbance or fluorescence, which put limitations on developing this technique for a high through-put screening [21-23]. Measurement of $P_i$ released from $IP_6$ by phytase is an end point assay that provides color development proportional to the amount of Pi released, but it requires a suitable choice of enzyme dose and assay time beside the tediousness and carefulness in handling the toxic vanadate and molybdate reagents [24-27]. The color development may vary with the reaction conditions such as pH. Attempts have been made to assay phytase kinetically using p-nitrophenyl phosphate or p-nitrophenyl pyrophosphate as substrate. However, it is difficult to differentiate whether the yellow color produced upon substrate hydrolysis is due to phytase or the action of phosphatases that occur widely in biological materials [28-29]. Moreover, not all phytases show good activity toward these two artificial substrates [30-32].

Due to the importance in animal nutrition, phytase becomes one of the most assayed enzymes in feed research and feed industrial analysis laboratories as well as in feed mills. Research laboratories need to screen protein engineered phytase variants with improved performances, especially heat-stability and pepsin resistance while breeders need a phytase assay in order to be sure if the phytase added to their feed is still active so that they can save the addition of calcium phosphate. However, due to the toxic chemicals or the specific equipments needed for the phytase assay, routine phytase assay has not been done outside a well-equipped laboratory. Thus it is clear that there is a need for a simple and faster alternative method for assaying phytases. Our preliminary tests have shown that phytases catalyze the hydrolysis of the protein/peptide-phytate complexes and, to a less extent, complexes with calcium ion, releasing $P_i$ and simultaneously reducing the turbidity of the substrate solution. In the present study, the use of $IP_6$-lysozyme complex as substrate to determine phytase activity kinetically by monitoring the turbidity reduction was established and compared with that of the traditional method. The developed method was used for the determination of activities of different bacterial and fungal phytases over a wide range of pH.

Phytase (EC 3.1.3.-) hydrolyzes phytate ($IP_6$) present in cereals and grains to release inorganic phosphate (Pi), thereby making it bioavailable. The most commonly used method to assay phytase, developed nearly a century ago, measures the $P_i$ liberated from $IP_6$. This traditional end point assay is time consuming and well known for its cumbersomeness in addition to requiring extra caution for handling the toxic regents used. This paper reports a simple, fast and nontoxic kinetic method adaptable for high through-put for assaying phytase using $IP_6$-lysozyme as a substrate. The assay is based on the principle that $IP_6$ forms stable turbid complexes with positively charged lysozyme in a wide pH range and hydrolysis of the IP6 in the complex is accompanied with a decrease in turbidity monitored at 600 nm. The turbidity decrease correlates well to the released $P_i$ from $IP_6$. This kinetic method was found useful in assaying histidine acid phytases, including 3- and 6-phytases, a class representing all commercial phytases, and alkaline β-propeller phytase from *Bacillus* sp. The influences of temperature, pH, phosphate and other salts on the kinetic assay were examined. Salts including NaCl, $CaCl_2$, and phosphate all showed a concentration-dependent interference.

The present invention is now in the following numbered summary paragraphs.

1. A method for detecting an enzymatic activity comprising the steps of:
(a) providing a medium comprising a continuous and a disperse phase, wherein the disperse phase comprises:
  i) a first component which is a polyvalent component, and
  ii) a second component which is an ionic component,
wherein the polyvalent component and the ionic component are held together by one or more intermolecular interactions to form the disperse phase,
wherein the disperse phase provides a detectable property to the medium;
(b) providing a sample that comprises or is suspected of comprising the enzymatic activity, wherein the enzymatic activity is capable of affecting the disperse phase to cause a detectable change in the detectable property of the medium;
(c) contacting the medium with the sample;
(d) determining if there is a change in the detectable property of the medium.
2. The method according to paragraph 1, wherein the enzymatic activity is capable of hydrolysing the first polyvalent component and/or the second ionic component intramolecularly.
3. The method according to any one of the preceding paragraphs wherein the enzymatic activity is a protease activity.
4. The method according to any one of the preceding paragraphs wherein the protease activity is an endoprotease activity.
5. The method according to paragraph 1 or 2 wherein the enzymatic activity is a phosphohydrolase activity, a phosphomonoesterase activity or a phytase activity.
6. The method according to paragraph 5, wherein the enzymatic activity is a phytase activity.
7. The method according to any one of the preceding paragraphs wherein the ionic component is a protein.
8. The method according to paragraph 7 wherein the protein is selected from the group consisting of: caseins, soy proteins, porcine haemoglobins, N,N-dimethylated casein, bovine beta-lactoglobulin, bovine or swine serum albumin, lysozyme, a protein modified with a chromophore, and any combination(s) thereof.
9. The method according to any one of the preceding paragraphs wherein, the polyvalent component is selected from the group consisting of: phytic acid, a component of a phytate salt and inositol covalently linked with 1 to 6 phosphate groups or sulphate groups.
10. The method according to any one of the preceding paragraphs wherein the disperse phase provides a detectable property to the medium that correlates with the amount of disperse phase.
11. The method according to any one of the preceding paragraphs wherein the method comprises correlating the change in the detectable property of the medium to the presence or amount of the enzyme activity.
12. The method according to any one of the preceding paragraphs wherein the method comprises comparing the change in the detectable property of the medium to a control.

13. The method according to any one of the preceding paragraphs wherein the detectable property of the medium is an optical property or viscosity.

14. The method according to paragraph 13 wherein the optical property is turbidity, absorbance of light or emission of fluorescence or phosphorescence.

15. The method according to any one of the preceding paragraphs wherein the detectable property is measured by eye or by using a ruler, turbidimeter, viscometer, spectrophotometer, fluorimeter or fluorescence spectrophotometer.

16. The method according to paragraph 15 wherein the detectable property is measured using a ruler.

17. The method according to any one of the preceding paragraphs wherein the disperse phase further comprises monovalent cations, divalent cations or trivalent cations.

18. The method according to any one of the preceding paragraphs wherein the medium is at a pH below the pI of the protein.

19. The method according to any one of the preceding paragraphs wherein the medium is at between pH 1.8 and pH 8.5

20. The method according to any one of the preceding paragraphs wherein the sample is a sample of food, feed, feed premix, a food ingredient, a feed ingredient, an enzyme preparation or a fermentation broth.

21. A method according to any one of the preceding paragraphs for detecting an enzymatic activity which is a protease activity or a phytase activity comprising the steps of:
(a) providing a medium comprising a continuous and a disperse phase, wherein the disperse phase comprises: i) phytic acid, and ii) a protein,
wherein the protein has at least one positively charged group, or wherein the medium is below the pI of the protein and the protein and the phytic acid are held together by one or more intermolecular interactions to form the disperse phase,
wherein the disperse phase provides turbidity, viscosity or fluorescence to the medium;
(b) providing a sample that comprises or is suspected of comprising the enzymatic activity,
wherein the enzymatic activity is capable of affecting the disperse phase to cause a detectable change in the turbidity, viscosity or the fluorescence of the medium;
(c) contacting the medium with the sample;
(d) determining if there is a detectable change in the turbidity, absorbance, viscosity or the fluorescence of the medium.

22. A method for detecting an enzymatic activity which is a protease activity or a phytase activity comprising the steps of:
(a) providing a medium comprising a continuous and a disperse phase, wherein the disperse phase comprises: i) phytic acid, and ii) a protein,
wherein the protein has at least one positively charged group, or wherein the medium is below the pI of the protein and the protein and the phytic acid are held together by one or more intermolecular interactions to form the disperse phase,
wherein the disperse phase provides turbidity, viscosity or fluorescence to the medium;
(b) providing a sample that comprises or is suspected of comprising the enzymatic activity, wherein the enzymatic activity is capable of affecting the disperse phase to cause a detectable change in the turbidity, viscosity or the fluorescence of the medium;
(c) contacting the medium with the sample;
(d) determining if there is a detectable change in the turbidity, absorbance, viscosity or the fluorescence of the medium.

23. A method according to paragraph 21 or 22 wherein the enzymatic activity is a protease activity and the protease activity hydrolyses the protein in the disperse phase thereby causing a detectable change in the turbidity or the fluorescence of the medium.

24. A method according to paragraph 21 or 22 wherein the enzymatic activity is a phytase activity and the phytase activity hydrolyses at least one phosphate group from the phytic acid molecule in the disperse phase thereby causing a detectable change in the turbidity, viscosity or the fluorescence of the medium.

25. A method according to any one of paragraphs 21 to 24 wherein the ratio of the phytic acid to the protein in the disperse phase is 1:6-1:100, preferably 1:20-1:70, more preferably 1:45-1:55, more preferably 1:50.

26. A quantitative, semi-quantitative or qualitative assay method for enzyme activity comprising the method according to any one of the preceding paragraphs.

27. A kit for detecting protease or phytase activity using the method according to any one of paragraphs 1 to 25.

28. A kit for detecting protease activity using the method according to paragraph 3 or any paragraph dependent thereon comprising a turbid liquid medium or a turbid gel medium, wherein the turbidity may be reduced by protease activity.

29. A kit for detecting phytase activity using the method according to paragraph 5 or any paragraph dependent thereon comprising a turbid liquid medium or a turbid gel medium, wherein the turbidity may be reduced by phytase activity.

30. Use of a method according to any one of paragraphs 1 to 26 or a kit according to any one of paragraphs 27 to 29 for testing enzyme activity in an enzyme preparation, a fermentation broth, a food, a feed, a food ingredient, a feed ingredient, a processed food product or a processed feed product or in an extract of any one thereof.

31. Use of a method according to any one of paragraphs 1 to 26 or a kit according to any one of paragraphs 27 to 29 for testing enzyme activity in a food, a feed, a food ingredient, a feed ingredient, a processed food product or a processed feed product or in an extract of any one thereof.

32. Use of a method according to any one of paragraphs 1 to 28 or a kit according to any one of paragraphs 27 to 29 for screening for enzyme activities of new enzyme molecules.

33. A method, kit or use as described herein with reference to the figures and examples.

The invention is further described in the following numbered summary paragraphs:

1a. A method for detecting an enzymatic activity which is a protease activity or a phytase activity comprising the steps of:
(a) providing a medium comprising a continuous and a disperse phase, wherein the disperse phase comprises: i) phytic acid, and ii) a protein,
wherein the protein has at least one positively charged group, or wherein the medium is below the pI of the protein and the protein and the phytic acid are held together by one or more intermolecular interactions to form the disperse phase,
wherein the disperse phase provides turbidity, viscosity or fluorescence to the medium;
(b) providing a sample that comprises or is suspected of comprising the enzymatic activity, wherein the enzymatic activity is capable of affecting the disperse phase to cause a detectable change in the turbidity, viscosity or the fluorescence of the medium;

(c) contacting the medium with the sample;

(d) determining if there is a detectable change in the turbidity, absorbance, viscosity or the fluorescence of the medium.

2a. A method according to paragraph 1a wherein the enzymatic activity is a protease activity and the protease activity hydrolyses the protein in the disperse phase thereby causing a detectable change in the turbidity or the fluorescence of the medium.

3a. A method according to paragraph 1a wherein the enzymatic activity is a phytase activity and the phytase activity hydrolyses at least one phosphate group from the phytic acid molecule in the disperse phase thereby causing a detectable change in the turbidity, viscosity or the fluorescence of the medium.

4a. A method according to any one of the preceding paragraphs wherein the protein is selected from the group consisting of: caseins, soy proteins, rapeseed protein, mustard protein, porcine haemoglobins, N,N-dimethylated casein, bovine beta-lactoglobulin, bovine or swine serum albumin, lysozyme, a protein modified with a chromophore, and any combination(s) thereof.

5a. A method according to any one of the preceding paragraphs wherein the ratio of the phytic acid to the protein in the disperse phase is 1:6-1:100, preferably 1:20-1:70, more preferably 1:45-1:55, more preferably 1:50.

6a. The method according to any one of the preceding paragraphs wherein the medium is at between pH 1.8 and pH 8.5.

7a. The method according to any one of the preceding paragraphs wherein the method comprises comparing the change in the detectable property of the medium to a control.

8a. A quantitative, semi-quantitative or qualitative assay method for enzyme activity comprising the method according to any one of the preceding paragraphs.

9a. A kit for detecting phytase or protease activity using the method according to any one of the preceding paragraphs.

10a. A kit for detecting protease activity using the method according to any one of paragraphs 1a to 8a comprising a turbid liquid medium or a turbid gel medium, wherein the turbidity may be reduced by protease activity.

11a. A kit for detecting phytase activity using the method according to any one of paragraphs 1a to 8a comprising a turbid liquid medium or a turbid gel medium, wherein the turbidity may be reduced by phytase activity.

12a. Use of a method according to any one of paragraphs 1a to 8a or a kit according to any one of paragraphs 9a to 11a for testing enzyme activity in an enzyme preparation, a fermentation broth, a food, a feed, a food ingredient, a feed ingredient, a processed food product or a processed feed product or in an extract of any one thereof.

13a. Use of a method according to any one of paragraphs 1a to 8a or a kit according to any one of paragraphs 9a to 12a for testing enzyme activity in a food, a feed, a food ingredient, a feed ingredient, a processed food product or a processed feed product or in an extract of any one thereof.

14a. Use of a method according to any one of paragraphs 1a to 8a or a kit according to any one of paragraphs 9a to 13a for screening for enzyme activities of new enzyme molecules.

15a. A method for detecting an enzymatic activity comprising the steps of:

(a) providing a medium comprising a continuous and a disperse phase, wherein the disperse phase comprises: i) a first component which is a polyvalent component, and ii) a second component which is an ionic component, wherein the polyvalent component and the ionic component are held together by one or more intermolecular interactions to form the disperse phase, wherein the disperse phase provides a detectable property to the medium;

(b) providing a sample that comprises or is suspected of comprising the enzymatic activity, wherein the enzymatic activity is capable of affecting the disperse phase to cause a detectable change in the detectable property of the medium;

(c) contacting the medium with the sample;

(d) determining if there is a change in the detectable property of the medium.

All publications mentioned in the above specification are herein incorporated by reference. Various modifications and variations of the described methods and system of the present invention will be apparent to those skilled in the art without departing from the scope and spirit of the present invention. Although the present invention has been described in connection with specific preferred embodiments, it should be understood that the invention as claimed should not be unduly limited to such specific embodiments. Indeed, various modifications of the described modes for carrying out the invention which are obvious to those skilled in biochemistry or related fields are intended to be within the scope of the following claims.

REFERENCES

[i.] Fiske, C. H. & Subbarow, Y. (1925). The Colorimetric Determination of Phosphorus. J. Biol. Chem. 66, 375-400.

[ii.] Lowry, O. H. & Lopez, J. A. (1946). The Determination of Inorganic Phosphate in the Presence of Labile Phosphate Esters. J. Biol. Chem. 162, 421-428.

[iii.] Prestwich, S. O. and Bolton, T. B., Measurement of picomole amounts of any inositol phosphate isomer separable by h.p.l.c. by means of a bioluminescence assay, Biochem. J. (1991) 274, 663-672.

[iv.] Wodzinski R. J., Ullah A. H. (1996), Adv Appl Microbiol. 42, 263-302.

[v.] Michele Susan Yarnell and Lilian Zeitouni. Reagents, methods and kits for detecting feed enzymes. United State Patent application Publication, US2005/0009116A. Pub. Date: Jan. 13, 2005.

[vi.] Howson and Davis, Production of phytate-hydrolyzing enzyme by some fungi. Enzyme Microb. Technol. 5 (1983): 377-382. H. D. Bae et al., A novel staining method for detecting phytase activity, Journal of Microbiological Methods 39 (1999) 17-22

[vii.] Blaabjerg, K; Carlson, D.; Hansen-Møller, J.; Tauson, A.-H.; Poulsen, H. D. In vitro degradation of phytate and lower inositol phosphates in soaked diets and feedstuffs, Livestock Sci. 2007, 109, 240-243

[viii.] Engelen A J, van der Heeft F C, Randsdorp P H, Smit E L. Simple and rapid determination of phytase activity. J AOAC Int. 1994 May-June; 77(3):760-4

[1] B. C. Oh, W. C. Choi, S. Park, Y. O. Kim, T. K. Oh, Biochemical properties and substrate specificities of alkaline and histidine acid phytase, Appl. Microbiol. Biotechnol. 63 (2004) 362-372.

[2] H. W. Lopez, F. Leenhardt, C. Coudray, C. Remesy, Mineral and phytic acid interactions: is it a real problem for human nutrition, Int. J. Food Sci. Technol. 37 (2002) 727-739.

[3] V. T. Maddaiah, A. A. Kurnick, B. L. Reid, Phytic acid studies, Proc. Soc. Exp. Biol. Med. 115 (1964) 391-393.

[4] K. B. Nolan, P. A. Duffin, D. J. Mc Weeny, Effect of phytate on mineral bioavalability. In vitro studies on $Mg^{2+}$, $Ca^{2+}$, $Fe^{3+}$, $Cu^{2+}$ and $Zn^{2+}$ (also $Cd^{2+}$) solubilities in the presence of phytate, J. Sci. Food Agr. 40 (1987) 79-85.

[5] P. Vats, U. C. Banerjee, Production studies and catalytic properties of phytases (myo-inositolhexakisphosphate phosphohydrolase): an overview, Enzyme Microb. Technol. 35 (2004) 3-4.

[6] M. Cheryan, Phytic acid interaction in food systems, CRC Crit. Rev. Food Sci. Nutri. 13 (1980) 297-335.

[7] D. H. Kim, B. C. Oh, W. C. Choi, J. K. Lee, T. K. Oh, Enzymatic evaluation of *Bacillus amyloliquefaciens* phytase as a feed additive, Biotechnol. Lett. 21 (1999) 925-927.

[8] M. A. Mallin, Impact of industrial animal production on river and estuaries, American Sci. 88 (2000) 26-73.

[9] A. Vohra, T. Satyanarayana, A cost-effective cane molasses medium for enhanced cell-bound phytase production by *Pichia anomala*, J. Appl. Microbiol. 97 (2004) 471-476.

[10] C. M. Weaver, S. Kannan, Phytate and mineral availability, in: N. R. Reddy (Eds.), Food Phytates, CRC Press, Boca Raton, Fla., 2002, pp. 211-223.

[11] N. R. Reddy, M. D. Pierson, S. K. Sathe, D. K. Salunkhe, Interactions of phytate with proteins and minerals, in: Phytate in Legumes and Cereals, CRC press, Boca Raton, Fla., 1989, pp. 57-70.

[12] T. Jacobsen, D. E. Slotfeldt, Phytic acid and metal availability: a study of Ca and Cu binding. Cereal Chem. 60 (1983) 392-395.

[13] B. E. Knuckles, Effect of phytate and partially hydrolyzed phytate on in vitro protein digestibility, J. Food Sci. 50 (1985) 1080-1082.

[14] E. Carnovale, E. Lugaro, G. Lombardiboccia, Phytic acid in faba bean and pea-effect on protein availability, Cereal Chem. 65 (1988) 114-117.

[15] I. A. Vaintraub, V. P. Bulmaga, Effect of phytate on the in vitro activity of digestive proteinases, J. Agr. Food Chem. 39 (1991) 859-861.

[16] U. Konietzny, R. Greiner (Eds.), Phytic acid and Nutritional Impact, 2 ed., Elsevier Science, Amsterdam, 2003.

[17] A. K. Kies, L. H. De Jonge, P. A. Kemme, A. W. Jongbloed, Interaction between protein, phytate, and microbial phytase. In vitro studies, J. Agr. Food Chem. 54 (2006) 1753-1758.

[18] A. J. Cowieson, P. H. Selle, V. Ravindran, Influence of dietary phytic acid and source of microbial phytase on ileal endogenous amino acid flows in broiler chickens, Poultry Sci. 87 (2008) 64-64.

[19] R. U. Makower, Extraction and dertermination of phytic acid in beans (*Phaseolus-vulgaris*), Cereal Chem. 47 (1970) 288-295.

[20] D. B. Thompson, J. W. Erdman, Phytic acid determination in soybeans, J. Food Sci. 47 (1982) 513-517.

[21] T. Ishiguro, T. Ono, K. Nakasato, C. Tsukamoto, S. Shimada, Rapid measurement of phytate in raw soymilk by mid-infrared spectroscopy, Biosci. Biotech. Biochem. 67 (2003) 752-757.

[22] E. Skoglund, N. G. Carlsson, A. S. Sandberg, High-performance chromatographic separation of inositol phosphate isomers on strong anion exchange columns, J. Agr. Food Chem. 46 (1998) 1877-1882.

[23] Q. C. Chen, B. W. Li, Separation of phytic acid and other related inositol phosphates by high-performance ion chromatography and its applications, J. Chromatogr. A 1018 (2003) 41-52.

[24] G. Gizzi, P. Thyregod, C. von Hoist, G. Bertin, K. Vogel, M. Faurschou-Isaksen, R. Betz, R. Murphy, B. B. Andersen, Determination of phytase activity in feed: Interlaboratory study, J. AOAC Int. 91 (2008) 259-267.

[25] A. J. Engelen, F. C. Vanderheeft, P. H. G. Randsdorp, E. L. C. Smit, Simple and rapid determination of phytase activity, J. AOAC Int. 77 (1994) 760-764.

[26] M. Shimizu, Purification and characterization of phytase from *Bacillus* subtillis (nato) N-77, Biosci. Biotechnol. Biochem. 56 (1992) 1266-1269.

[27] S. J. Yoon, Y. J. Choi, H. K. Mint, K. K. Cho, J. W. Kim, S. C. Lee, Y. H. Jung, Isolation and identification of phytase producing bacterium, *Enterobacterium* sp. 4, and enzymatic properties of phytase enzyme, Enzyme Microb. Technol. 18 (1996) 449-454.

[28] R. M. Berka, M. W. Rey, K. M. Brown, T. Byun, A. V. Klotz, Molecular characterization and expression of a phytase gene from the thermophilic fungus *Thermomyces lanuginosus*, Appl. Environ. Microbiol. 64 (1998) 4423-4427.

[29] J. K. Heinonen, R. J. Lahti, A new and convenient colorimetric determination of inorganic orthophosphate and its application to the assay of inorganic pyrophosphatase, Anal. Biochem. 113 (1981) 313-317.

[30] Y. O. Kim, H. K. Kim, K. S. Bae, J. H. Yu, T. K. Oh, Purification and properties of a thermostable phytase from *Bacillus* sp. DS11, Enzyme Microb. Technol. 22 (1998) 2-7.

[31] Y. M. Choi, H. J. Suh, J. M. Kim, Purification and properties of extracellular phytase from *Bacillus* sp. KHU-10, J. Protein Chem. 20 (2001) 287-292.

[32] J. Kerovuo, M. Lauraeus, P. Nurminen, N. Kalkkinen, J. Apajalahti, Isolation, characterization, molecular gene cloning, and sequencing of a novel phytase from *Bacillus subtilis*, Appl. Environ. Microbiol. 64 (1998) 2079-2085.

[33] T. T. Tran, G. Mamo, B. Mattiasson, H.-K. R., A thermostable phytase from *Bacillus* sp. MD2: cloning, expression and high-level production in *Escherichia coli*, J. Ind. Microbiol. Biotechnol. 37 (2010) 279-287.

[34] K. Okubo, D. V. Myers, G. A. Iacobucci, Binding of phytic acid to glycinin, Cereal Chem. 53 (1976) 513-524.

[35] T. D. Fontaine, W. A. Pons, G. W. Irving, Protein-phytic acid relationship in peanuts and cottonseed, J. Biol. Chem. 164 (1946) 487-507.

[36] G. Alderton, W. H. Ward, H. L. Fevold, Isolation of lysozyme from egg white J. Biol. Chem. 157 (1945) 43-58.

[37] S. Ebisuno, S. Moimoto, T. Yoshida, T. Fukatani, Y. S., T. Ohkawa, Studies of phytin therapy for calcium urolithiasis with hypercalciuria. 1. Basal experiments, Nippon Hinyokika Gakkai Zasshi 71 (1986) 5-11.

[38] Y. H. Chung, C. H. Chun, S. H. Lee, C. H. Lim, Influence of septic in *Vibrio Vulnificus* from phytic acid, J. Agri. Sci. 32 (2005) 71-80.

[39] Y. H. Chung, W. W. Park, S. Y. Lee, S. W. Lee, C. H. Lim, M. H. Yoon, Effect of phytic acid on viability of *Vibrio vulnificus* and on septicemia-induced mice, J. Korean Soc. Appl. Biol. Chem. 49 (2006) 15-20.

[40] A. H. J. Ullah, K. Sethumadhavan, E. J. Mullaney, Salt effect on the pH profile and kinetic parameters of microbial phytases, J. Agr. Food Chem. 56 (2008) 3398-3402.

[41] R. Greiner, U. Konietzny, K. D. Jany, Purification and characterization of two phytases from *Escherichia coli*, Arch. Biochem. Biophys. 303 (1993) 107-113.

[42] A. H. J. Ullah, K. Sethumadhavan, PhyA gene product of *Aspergillus ficuum* and *Peniophora lycii* produces dissimilar phytases, Biochem. Biophys. Res. Comm. 303 (2003) 463-468.

[43] J. Kerovuo, J. Rouvinen, F. Hatzack, Analysis of myo-inositol hexakiphosphate hydrolysis by *Bacillus* phytase: indication of a novel reaction mechanism, Biochem. J. 352 (2000) 623-628.

[44] S. Shin, N. C. Ha, B. C. Oh, T. K. Oh, B. H. Oh, Enzyme mechanism and catalytic property of beta propeller phytase, Structure 9 (2001) 851-858.

[45] W. Eeckhout, M. De Paepe, Total phosphorus, phytase phosphorus and phytase activity in plant feedstuffs. An. Feed Sci. Technol. 47 (1994) 19-29.

[46] T. R. Shieh, J. H. Ware, Survey of microorganism for the production of extracellular phytase. Appl. Microbiol. 16 (1968) 1348-1351.

[47] C. H. Stahl, D. B. Wilson, X. G. Lei, Comparision of extracellular *Escherichia coli* AppA phytases expressed in *Streptomyces lividans* and *Pichia pastoris*, Biotechnol. Lett. 25 (2003) 827-831.

The invention claimed is:

1. A method of detecting a phytase activity or a protease activity comprising the steps of:
    providing a medium comprising a continuous phase and a disperse phase, wherein the disperse phase comprises:
    (1) a first component, the first component being a phytate or a phytic acid, and
    (2) a second component, the second component being a protein,
    wherein the first component and the second component are held together by one or more intermolecular interactions, wherein the phase provides a detectable property of turbidity to the medium;
    providing a sample that comprises one or more of the phytase activity or the protease activity, wherein the one or more of the phytase activity or the protease activity are capable of affecting the disperse phase to cause a change in the turbidity of the medium;
    contacting the medium with the sample; and
    determining that there is a detectable change in the turbidity of the medium to determine an amount of the phytase activity or the protease activity in the sample.

2. The method of claim 1, wherein the protein in the disperse phase of the medium is selected from a group comprising caseins, soy proteins, rapeseed proteins, mustard proteins, porcine haemoglobins, N,N-dimethylated caseins, bovine beta-lactoglobulins, bovine serum albumins, swine serum albumins, lysozymes, or proteins modified with a chromophore.

3. The method of claim 1, wherein the medium is between a pH of 1.8 and a pH of 8.5.

4. The method of claim 1, wherein the method comprises comparing the change in the detectable property of the medium to a control.

5. The method of claim 1, wherein the sample is a biological sample.

6. The method of claim 5, wherein the biological sample is an enzyme preparation comprised of a fermentation broth, a feed or in an extract of the fermentation broth or the feed.

7. The method of claim 1, wherein determining if there is a detectable change in the detectable property of the medium comprises one or more of a quantitative assay, a semi-quantitative assay or a qualitative assay.

8. A method of detecting a phytase activity comprising the steps of:
    providing a medium comprising a continuous phase and a disperse phase, wherein the disperse phase comprises:
    (1) a first component, the first component being a phytate or a phytic acid, and
    (2) a second component, the second component being a protein, wherein the first component and the second component are held together by one or more intermolecular interactions, wherein the disperse phase provides a detectable property of turbidity to the medium;
    providing a sample that comprises the phytase activity, wherein the phytase activity is capable of affecting the disperse phase to cause a change in the turbidity of the medium;
    contacting the medium with the sample, wherein one or more protease inhibitors are added to the sample in a sufficient amount as to inhibit any protease activity; and
    determining that there is a detectable change in the turbidity of the medium to determine an amount of the phytase activity in the sample.

9. The method of claim 8, wherein the protein in the disperse phase of the medium is selected from a group comprising caseins, soy proteins, rapeseed proteins, mustard proteins, porcine haemoglobins, N,N-dimethylated caseins, bovine beta-lactoglobulins, bovine serum albumins, swine serum albumins, lysozymes, or proteins modified with a chromophore.

10. The method of claim 8, wherein the sample is a biological sample.

11. The method of claim 10, wherein the biological sample is an enzyme preparation comprised of a fermentation broth, a feed or in an extract of the fermentation broth or the feed.

12. The method of claim 8, wherein determining if there is a detectable change in the detectable property of the medium comprises one or more of a quantitative assay, a semi-quantitative assay or a qualitative assay.

* * * * *